United States Patent
Gawad et al.

(10) Patent No.: US 11,905,553 B2
(45) Date of Patent: Feb. 20, 2024

(54) METHOD FOR NUCLEIC ACID AMPLIFICATION

(71) Applicant: ST. JUDE CHILDREN'S RESEARCH HOSPITAL, INC., Memphis, TN (US)

(72) Inventors: Charles Gawad, Germantown, TN (US); John Easton, Memphis, TN (US); Veronica Gonzalez-Pena, Memphis, TN (US)

(73) Assignee: ST. JUDE CHILDREN'S RESEARCH HOSPITAL, INC., Memphis, TN (US)

(*) Notice: Subject to any disclaimer, the term of this patent is extended or adjusted under 35 U.S.C. 154(b) by 538 days.

(21) Appl. No.: 16/965,796

(22) PCT Filed: Jan. 28, 2019

(86) PCT No.: PCT/US2019/015452
§ 371 (c)(1),
(2) Date: Jul. 29, 2020

(87) PCT Pub. No.: WO2019/148119
PCT Pub. Date: Aug. 1, 2019

(65) Prior Publication Data
US 2020/0362394 A1  Nov. 19, 2020

Related U.S. Application Data
(60) Provisional application No. 62/623,471, filed on Jan. 29, 2018.

(51) Int. Cl.
| C12Q 1/686 | (2018.01) |
| C12N 15/10 | (2006.01) |
| C12Q 1/6869 | (2018.01) |
| C12Q 1/6883 | (2018.01) |

(52) U.S. Cl.
CPC ......... *C12Q 1/686* (2013.01); *C12N 15/1093* (2013.01); *C12Q 1/6869* (2013.01); *C12Q 1/6883* (2013.01); *C12Q 2600/156* (2013.01)

(58) Field of Classification Search
CPC .... C12Q 1/686; C12Q 1/6869; C12Q 1/6883; C12Q 2600/156; C12Q 1/6806; C12N 15/1093; C40B 40/06
See application file for complete search history.

(56) References Cited

U.S. PATENT DOCUMENTS

| 5,001,050 A | 3/1991 | Blanco et al. |
| 5,198,543 A | 3/1993 | Blanco et al. |
| 6,432,360 B1 | 8/2002 | Church |
| 6,485,944 B1 | 11/2002 | Church et al. |
| 6,511,803 B1 | 1/2003 | Church et al. |
| 6,565,727 B1 | 5/2003 | Shenderov |
| 6,773,566 B2 | 8/2004 | Shenderov |
| 6,911,132 B2 | 6/2005 | Pamula et al. |
| 6,977,033 B2 | 12/2005 | Becker et al. |
| 6,977,148 B2 | 12/2005 | Dean et al. |
| 7,052,244 B2 | 5/2006 | Fouillet et al. |
| 7,163,612 B2 | 1/2007 | Sterling et al. |
| 7,328,979 B2 | 2/2008 | Decre et al. |
| 7,425,431 B2 | 9/2008 | Church et al. |
| 7,547,380 B2 | 6/2009 | Velev |
| 7,641,779 B2 | 1/2010 | Becker et al. |
| 8,053,192 B2 | 11/2011 | Bignell et al. |
| 8,835,358 B2 | 9/2014 | Fodor et al. |
| 8,895,249 B2 | 11/2014 | Shen et al. |
| 9,624,538 B2 | 4/2017 | Church et al. |
| 9,797,841 B2 | 10/2017 | Schumm et al. |
| 9,968,901 B2 | 5/2018 | Head et al. |
| 10,450,562 B2 | 10/2019 | Brown |
| 11,643,682 B2 | 5/2023 | Gawad et al. |
| 2003/0132538 A1 | 7/2003 | Chandler |
| 2003/0205632 A1 | 11/2003 | Kim et al. |
| 2005/0118574 A1 | 6/2005 | Chandler et al. |
| 2005/0179746 A1 | 8/2005 | Roux et al. |
| 2005/0260686 A1 | 11/2005 | Watkins et al. |
| 2005/0277197 A1 | 12/2005 | Chandler et al. |
| 2006/0039823 A1 | 2/2006 | Yamakawa et al. |
| 2006/0159962 A1 | 7/2006 | Chandler et al. |
| 2006/0164490 A1 | 7/2006 | Kim et al. |
| 2006/0194331 A1 | 8/2006 | Pamula et al. |
| 2007/0023292 A1 | 2/2007 | Kim et al. |
| 2007/0064990 A1 | 3/2007 | Roth |
| 2007/0207513 A1 | 9/2007 | Sorensen et al. |

(Continued)

FOREIGN PATENT DOCUMENTS

| EP | 3514243 A1 | 7/2019 |
| WO | WO-02061428 A2 | 8/2002 |

(Continued)

OTHER PUBLICATIONS

Aliotta et al.: Thermostable Bst DNA polymerase I lacks a 3'-->5' proofreading exonuclease activity.Genet Anal. (Netherlands) 12: 185-195 (1996).
Boehmer et al.: Herpes simplex virus type 1 ICP8: helix-destabilizing properties. J Virol.67(2): 711-715 (1993).
Boeva, et al. Control-FREEC: a tool for assessing copy number and allelic content using next-generation sequencing data. Bioinformatics. Feb. 1, 2012;28(3):423-5. doi: 10.1093/bioinformatics/btr670. Epub Dec. 6, 2011.
Chatterjee, et al. Cloning and overexpression of the gene encoding bacteriophage T5 DNA polymerase. Gene. Jan. 2, 1991;97(1):13-9.
Chen, et al. "Single-cell whole-genome analyses by Linear Amplification via Transposon Insertion (LIANTI)." Science 356.6334 (2017): 189-194.
Daher et al: Recombinase Polymerase Amplification for Diagnostic Applications. Clin Chem.62(7): 947-958 (2016).
De Bourcy et al.: A quantitative comparison of single-cell whole genome amplification methods. PLoS One.Aug. 19, 2014; 9(8): e105585.

(Continued)

*Primary Examiner* — Cynthia B Wilder
(74) *Attorney, Agent, or Firm* — Wilson Sonsini Goodrich & Rosati

(57) ABSTRACT

Provided herein are compositions and methods for accurate and scalable Primary Template-Directed Amplification (PTA) nucleic acid amplification and sequencing methods, and their applications for research, diagnostics, and treatment.

20 Claims, 38 Drawing Sheets

(56) References Cited

U.S. PATENT DOCUMENTS

| | | |
|---|---|---|
| 2008/0053205 A1 | 3/2008 | Pollack et al. |
| 2008/0124252 A1 | 5/2008 | Marchand et al. |
| 2008/0151240 A1 | 6/2008 | Roth |
| 2008/0242560 A1 | 10/2008 | Gunderson et al. |
| 2008/0269068 A1 | 10/2008 | Church et al. |
| 2008/0305481 A1 | 12/2008 | Whitman et al. |
| 2009/0192044 A1 | 7/2009 | Fouillet |
| 2009/0283407 A1 | 11/2009 | Shah et al. |
| 2009/0321262 A1 | 12/2009 | Adachi et al. |
| 2010/0096266 A1 | 4/2010 | Kim et al. |
| 2010/0330556 A1 | 12/2010 | Peter et al. |
| 2011/0048951 A1 | 3/2011 | Wu |
| 2012/0045797 A1 | 2/2012 | Kurn et al. |
| 2013/0274117 A1 | 10/2013 | Church et al. |
| 2013/0338042 A1* | 12/2013 | Shen .................. C12Q 1/6844 506/26 |
| 2013/0344492 A1 | 12/2013 | Ma |
| 2016/0376663 A1 | 12/2016 | Brown |
| 2017/0344866 A1 | 11/2017 | Fan et al. |
| 2019/0076813 A1 | 3/2019 | Head et al. |
| 2019/0390192 A1 | 12/2019 | Brown |

FOREIGN PATENT DOCUMENTS

| | | |
|---|---|---|
| WO | WO-03002736 A2 | 1/2003 |
| WO | WO-2004034013 A2 | 4/2004 |
| WO | WO-2005068656 A1 | 7/2005 |
| WO | WO-2005082098 A2 | 9/2005 |
| WO | WO-2006073504 A2 | 7/2006 |
| WO | WO-2007120241 A2 | 10/2007 |
| WO | WO-2008098236 A2 | 8/2008 |
| WO | WO-2008116221 A1 | 9/2008 |
| WO | WO-2008134153 A1 | 11/2008 |
| WO | WO-2012140224 A1 | 10/2012 |
| WO | WO-2012142213 A2 | 10/2012 |
| WO | WO-2013177220 A1 | 11/2013 |
| WO | WO-2013188582 A1 | 12/2013 |
| WO | WO-2015026853 A2 | 2/2015 |
| WO | WO-2015189588 A1 | 12/2015 |
| WO | WO-2016090273 A1 | 6/2016 |
| WO | WO-2019148119 A1 | 8/2019 |

OTHER PUBLICATIONS

Dean, et al. Comprehensive human genome amplification using multiple displacement amplification. Proc Natl Acad Sci U S A. Apr. 16, 2002;99(8):5261-6.

Dong et al.: Accurate identification of single-nucleotide variants in whole-genome-amplified single cells. Nat Methods. 14(5): 491-493 (2017).

Gawad et al.: Dissecting the clonal origins of childhood acute lymphoblastic leukemia by single-cell genomics. Proc Natl Acad Sci U S A. 111(50): 17947-17952 (2014).

Gole et al.: Massively parallel polymerase cloning and genome sequencing of single cells using nanoliter microwells. Nat Biotechnol. 31(12): 1126-1132 (2013).

Islam, et al. Quantitative single-cell RNA-seq with unique molecular identifiers. Nat Methods. Feb. 2014; 11(2):163-6.

Jacobsen, et al. The N-terminal amino-acid sequences of DNA polymerase I from *Escherichia coli* and of the large and the small fragments obtained by a limited proteolysis. Eur J Biochem. Jun. 15, 1974;45(2):623-7.

Jung, et al. Bacteriophage PRD1 DNA polymerase: evolution of DNA polymerases. Proc Natl Acad Sci U S A. Dec. 1987;84(23):8287-91.

Kaboord et al.: Accessory proteins function as matchmakers in the assembly of the T4 DNA polymerase holoenzyme. Curr Biol. 5: 149-157 (1995).

Kivioja, et al. Counting absolute numbers of molecules using unique molecular identifiers. Nat Methods. Nov. 20, 2011;9(1):72-4.

Kong et al.: Characterization of a DNA polymerase from the hyperthermophile archaea *Thermococcus litoralis*. Vent DNA polymerase, steady state kinetics, thermal stability, processivity, strand displacement, and exonuclease activities. J Biol. Chem. 268: 1965-1975 (1993).

Kwok, P.Y.: High-throughput genotyping assay approaches. Pharmacogenomics.1(1): 5 pages (2001).

Kwon et al.: Rational engineering of a DNA glycosylase specific for an unnatural cytosine:pyrene base pair. Chem Biol. 10(4): 351-359 (2003).

Lan et al.: Single-cell genome sequencing at ultra-high-throughput with microfluidic droplet barcoding. Nat Biotechnol.35(7): 640-646 (2017).

Landegren et al. Reading bits of genetic information: methods for single-nucleotide polymorphism analysis. Genome research 8.8 (1998): 769-776.

Langmore, J.P.: Rubicon Genomics, Inc. Pharmacogenomics.3(4): 557-560 (2002).

Ma et al.: Pan-cancer genome and transcriptome analyses of 1,699 paediatric leukaemias and solid tumours. Nature.555(7696): 371-376 (2018).

Matsumoto, et al. Primary structure of bacteriophage M2 DNA polymerase: conserved segments within protein-priming DNA polymerases and DNA polymerase I of *Escherichia coli*. Gene. Dec. 14, 1989;84(2):247-55.

Paris et al., Diagnostic accuracy of a loop-mediated isothermal PCR assay for detection of Orientia tsutsugamushi during acute Scrub Typhus infection. PLoS Neglected Tropical Diseases 5(9):e1307. doi: 10.1371/journal.pntd.0001307 (2011).

PCT/US2019/015452 International Search Report and Written Opinion dated Mar. 21, 2019.

Porreca, et al., Multiplex amplification of large sets of human exons. Nature Methods. 2007. 4: 931-6.

Rigler, et al. Differences in the mechanism of stimulation of T7 DNA polymerase by two binding modes of *Escherichia coli* single-stranded DNA-binding protein. J. Biol. Chem. 1995;;270(15):8910-9.

Schmitt et al., Detection of ultra-rare mutations by next-generation sequencing. PNAS. 109(36):14508-14523 (2012).

Shendure, et al., Accurate Multiplex Polony Sequencing of an Evolved Bacterial Genome. Science 309.5741 (Sep. 2005): 1728-1732. XP002427180, ISSN: 0036-8075, DOI: 10.1126/Science.1117839.

Shi et al.: Enabling large-scale pharmacogenetic studies by high-throughput mutation detection and genotyping technologies. Clin Chem.47(2): 164-172 (2001).

Siegal et al.: A novel DNA helicase from calf thymus. J Biol Chem.267(19): 13629-13635 (1992).

Skaliter, et al. Rolling circle DNA replication in vitro by a complex of herpes simplex virus type 1-encoded enzymes. Proc. Natl, Acad. Sci. USA. 1994;91(22):10665-9.

Tsurumi, et al. Functional interaction between Epstein-Barr virus DNA polymerase catalytic subunit and its accessory subunit in vitro. J. Virology. 1993;67(12):7648-53.

Villemain et al.: The N-terminal B-domain of T4 gene 32 protein modulates the lifetime of cooperatively bound Gp32-ss nucleic acid complexes. Biochemistry.35(45): 14395-14404 (1996).

Walker et al.: Detection of *Mycobacterium tuberculosis* DNA with thermophilic strand displacement amplification and fluorescence polarization. Clinical Chemistry 42: 1604-1608 (1996).

Wang et al.: CREST maps somatic structural variation in cancer genomes with base-pair resolution. Nat Methods.8(8): 652-654 (2011).

Yang et al.: Helicase-Dependent Isothermal Amplification of DNA and RNA by Using Self-Avoiding Molecular Recognition Systems. Chembiochem. 16(9): 1365-1370 (2015).

Zafar et al.: Monovar: single-nucleotide variant detection in single cells. Nat Methods. 13(6): 505-507 (2016).

Zhang et al.: Whole genome amplification from a single cell: implications for genetic analysis. Proc Natl Acad Sci U S A.89(13): 5847-5851 (1992).

Zhu, et al. Purification and characterization of PRD1 DNA polymerase. Biochim Biophys Acta. Oct. 18, 1994;1219(2):267-76.

(56) References Cited

OTHER PUBLICATIONS

Zijderveld, et al. Helix-destabilizing properties of the adenovirus DNA-binding protein. J. Virology. 1994;68(2):1158-64.

Zong et al. Genome-Wide Detection of Single Nucleotide and Copy Number Variations of a Single Human Cell. Science 338(6114):1622-1626 (2012).

European Application No. 19743724.7 Search Report dated Sep. 28, 2021.

Ramunas et al., Improved genome recovery and integrated cell-size analyses of individual uncultured microbial cells and viral particles. Nat Commun 8(1):84 (2017).

Leontis NB, et al. The non-Watson-Crick base pairs and their associated isostericity matrices. Nucleic Acids Res. Aug. 15, 2002;30(16):3497-531.

Ortigäo et al. Antisense effect of oligodeoxynucleotides with inverted terminal internucleotidic linkages: a minimal modification protecting against nucleolytic degradation. Antisense Res Dev2(2):129-146 (1992).

* cited by examiner

METHOD FOR NUCLEIC ACID AMPLIFICATION

CROSS-REFERENCE

This application is a National Stage Entry of application No. PCT/US2019/015452, filed on Jan. 28, 2019, which claims the benefit of U.S. provisional patent application No. 62/623,471 filed on Jan. 29, 2018, which is incorporated herein by reference in its entirety.

BACKGROUND

Research methods that utilize nucleic amplification, e.g., Next Generation Sequencing, provide large amounts of information on complex samples, genomes, and other nucleic acid sources. However there is a need for highly accurate, scalable, and efficient nucleic acid amplification and sequencing methods for research, diagnostics, and treatment involving small samples.

BRIEF SUMMARY

Provided herein are compositions comprising: at least one target nucleic acid molecule and an amplicon library, wherein the amplicon library comprises a plurality of polynucleotides obtained from amplification of the at least one target nucleic acid molecule, wherein at least some of the polynucleotides comprise a terminator nucleotide, wherein at least 5% of the polynucleotides are direct copies of the at least one target nucleic acid molecule. Further provided herein are compositions wherein at least 10% of the polynucleotides are direct copies of the at least one target nucleic acid molecule. Further provided herein are compositions wherein at least 15% of the polynucleotides are direct copies of the at least one target nucleic acid molecule. Further provided herein are compositions wherein at least 25% of the polynucleotides are direct copies of the at least one target nucleic acid molecule. Further provided herein are compositions wherein at least 50% of the polynucleotides are direct copies of the at least one target nucleic acid molecule. Further provided herein are compositions wherein 5-50% of the polynucleotides are direct copies of the at least one target nucleic acid molecule. Further provided herein are compositions wherein 5-25% of the polynucleotides are direct copies of the at least one target nucleic acid molecule. Further provided herein are compositions wherein no more than 50% of a cumulative fraction of polynucleotides comprises sequences of at least 80% of a cumulative fraction of sequences of the at least one target nucleic acid molecule. Further provided herein are compositions wherein no more than 50% of the cumulative fraction of the plurality of polynucleotides comprises sequences of the at least 85% of the cumulative fraction of target nucleic acid sequences. Further provided herein are compositions wherein no more than 50% of the cumulative fraction the plurality of polynucleotides comprises sequences of the at least 90% of the cumulative fraction of target nucleic acid sequences. Further provided herein are compositions wherein the amplicon library has a Gini index of no more than 0.5. Further provided herein are compositions wherein the amplicon library has a Gini index of no more than 0.4. Further provided herein are compositions wherein the plurality of polynucleotides is between about 50 and about 2000 nucleotides in length. Further provided herein are compositions wherein polynucleotides are between about 400 and about 600 nucleotides in length. Further provided herein are compositions wherein the number of polynucleotides is 100-5000. Further provided herein are compositions wherein the number of polynucleotides is 250-1250. Further provided herein are compositions wherein the number of polynucleotides is at least 100. Further provided herein are compositions wherein the number of polynucleotides is at least 500. Further provided herein are compositions wherein the number of polynucleotides is at least 1000. Further provided herein are compositions wherein at least some of the polynucleotides comprise a barcode. Further provided herein are compositions wherein the barcode comprises a cell barcode. Further provided herein are compositions wherein the barcode comprises a sample barcode. Further provided herein are compositions wherein at least some of the polynucleotides comprise a unique molecular identifier. Further provided herein are compositions wherein the plurality of polynucleotides comprises sequences at least partially representative of a genome. Further provided herein are compositions wherein the plurality of polynucleotides comprises sequences at least partially representative of at least two genomes. Further provided herein are compositions wherein the plurality of polynucleotides comprises sequences from cDNA. Further provided herein are compositions wherein at least 90% of the polynucleotides comprise a terminator nucleotide. Further provided herein are compositions wherein at least 98% of the polynucleotides comprise a terminator nucleotide. Further provided herein are compositions wherein the terminator nucleotide is attached to the 3' terminus of the at least some polynucleotides. Further provided herein are compositions wherein the terminator nucleotide is selected from the group consisting of nucleotides with modification to the alpha group, C3 spacer nucleotides, locked nucleic acids (LNA), inverted nucleic acids, 2' fluoro nucleotides, 3' phosphorylated nucleotides, 2'-O-Methyl modified nucleotides, and trans nucleic acids. Further provided herein are compositions wherein the nucleotides with modification to the alpha group are alpha-thio dideoxynucleotides. Further provided herein are compositions wherein the terminator nucleotide comprises modifications of the r group of the 3' carbon of the deoxyribose. Further provided herein are compositions wherein the terminator nucleotide is selected from the group consisting of 3' blocked reversible terminator containing nucleotides, 3' unblocked reversible terminator containing nucleotides, terminators containing 2' modifications of deoxynucleotides, terminators containing modifications to the nitrogenous base of deoxynucleotides, and combinations thereof. Further provided herein are compositions wherein the terminator nucleotides is selected from the group consisting of dideoxynucleotides, inverted dideoxynucleotides, 3' biotinylated nucleotides, 3' amino nucleotides, 3'-phosphorylated nucleotides, 3'-O-methyl nucleotides, 3' carbon spacer nucleotides including 3' C3 spacer nucleotides, 3' C18 nucleotides, 3' Hexanediol spacer nucleotides, acyclonucleotides, and combinations thereof. Further provided herein are compositions wherein the composition is contained in a droplet.

Provided herein are compositions comprising: at least one target nucleic acid molecule and an amplicon library, wherein the amplicon library comprises a plurality of polynucleotides obtained from amplification of the at least one target nucleic acid molecule, wherein at least some of the polynucleotides comprise a terminator nucleotide, wherein no more than 50% of a cumulative fraction of polynucleotides comprises sequences of at least 80% of a cumulative fraction of sequences of the at least one target nucleic acid molecule. Further provided herein are compositions wherein no more than 50% of the cumulative fraction of the plurality of polynucleotides comprises sequences of the at least 85% of the cumulative fraction of target nucleic acid sequences. Further provided herein are compositions wherein no more than 50% of the cumulative fraction the plurality of polynucleotides comprises sequences of the at least 90% of the cumulative fraction of target nucleic acid sequences. Further provided herein are compositions wherein the plurality of polynucleotides is between about 50 and about 2000 nucleotides in length. Further provided herein are compositions wherein polynucleotides are between about 400 and about 600 nucleotides in length. Further provided herein are compositions wherein the number of polynucleotides is 100-5000. Further provided herein are compositions wherein the number of polynucleotides is 250-1250. Further provided herein are compositions wherein the number of polynucleotides is at least 100. Further provided herein are compositions wherein the number of polynucleotides is at least 500. Further provided herein are compositions wherein the number of polynucleotides is at least 1000. Further provided herein are compositions wherein at least some of the polynucleotides comprise a barcode. Further provided herein are compositions wherein the barcode comprises a cell barcode. Further provided herein are compositions wherein the barcode comprises a sample barcode. Further provided herein are compositions wherein at least some of the polynucleotides comprise a unique molecular identifier. Further provided herein are compositions wherein the plurality of polynucleotides comprises sequences at least partially representative of a genome. Further provided herein are compositions wherein the plurality of polynucleotides comprises sequences at least partially representative of at least two genomes. Further provided herein are compositions wherein the plurality of polynucleotides comprises sequences from cDNA. Further provided herein are compositions wherein at least 90% of the polynucleotides comprise a terminator nucleotide. Further provided herein are compositions wherein at least 98% of the polynucleotides comprise a terminator nucleotide. Further provided herein are compositions wherein the terminator nucleotide is attached to the 3' terminus of the at least some polynucleotides. Further provided herein are compositions wherein the terminator nucleotide is selected from the group consisting of nucleotides with modification to the alpha group, C3 spacer nucleotides, locked nucleic acids (LNA), inverted nucleic acids, 2' fluoro nucleotides, 3' phosphorylated nucleotides, 2'-O-Methyl modified nucleotides, and trans nucleic acids. Further provided herein are compositions wherein the nucleotides with modification to the alpha group are alpha-thio dideoxynucleotides. Further provided herein are compositions wherein the terminator nucleotide comprises modifications of the r group of the 3' carbon of the deoxyribose. Further provided herein are compositions wherein the terminator nucleotide is selected from the group consisting of 3' blocked reversible terminator containing nucleotides, 3' unblocked reversible terminator containing nucleotides, terminators containing 2' modifications of deoxynucleotides, terminators containing modifications to the nitrogenous base of deoxynucleotides, and combinations thereof. Further provided herein are compositions wherein the terminator nucleotides is selected from the group consisting of dideoxynucleotides, inverted dideoxynucleotides, 3' biotinylated nucleotides, 3' amino nucleotides, 3'-phosphorylated nucleotides, 3'-O-methyl nucleotides, 3' carbon spacer nucleotides including 3' C3 spacer nucleotides, 3' C18 nucleotides, 3' Hexanediol spacer nucleotides, acyclonucleotides, and combinations thereof. Further provided herein are compositions wherein the composition is contained in a droplet.

Provided herein are methods of amplifying a target nucleic acid molecule, the method comprising: contacting a sample comprising the target nucleic acid molecule, at least one amplification primer, at least one nucleic acid polymerase, and a mixture of nucleotides, wherein the mixture of nucleotides comprises at least one terminator nucleotide which terminates nucleic acid replication by the polymerase, and amplifying the target nucleic acid molecule to generate a plurality of terminated amplification products, wherein the replication proceeds by strand displacement replication. Further provided herein are methods wherein the amplification is performed under substantially isothermic conditions. Further provided herein are methods wherein the amplification is performed under conditions wherein the temperature varies by no more than 10 degrees C. Further provided herein are methods wherein the amplification is performed under conditions wherein the temperature varies by no more than 5 degrees C. Further provided herein are methods wherein the nucleic acid polymerase is a DNA polymerase. Further provided herein are methods wherein the DNA polymerase is a strand displacing DNA polymerase. Further provided herein are methods wherein the nucleic acid polymerase is bacteriophage phi29 (Φ29) polymerase, genetically modified phi29 (Φ29) DNA polymerase, Klenow Fragment of DNA polymerase I, phage M2 DNA polymerase, phage phiPRD1 DNA polymerase, Bst DNA polymerase, Bst large fragment DNA polymerase, exo(-) Bst polymerase, exo(-)Bca DNA polymerase, Bsu DNA polymerase, a DNA polymerase sold under the trademark VENT®, an (exo-) DNA polymerase sold under the trademark VENT®, a DNA polymerase sold under the trademark DEEP VENT®, an (exo-) DNA polymerase sold under the trademark DEEP VENT®, a DNA polymerase sold under the trademark ISOPOL™, DNA polymerase I, a DNA polymerase sold under trademark THERMINATOR™, a T5 DNA polymerase sold under trademark SEQUENASE™, T7 DNA polymerase, a T7 DNA polymerase sold under trademark SEQUENASE™, or T4 DNA polymerase. Further provided herein are methods wherein the nucleic acid polymerase comprises 3'->5' exonuclease activity and the at least one terminator nucleotide inhibits the 3'->5' exonuclease activity. Further provided herein are methods wherein the nucleic acid polymerase does not comprise 3'->5' exonuclease activity. Further provided herein are methods wherein the polymerase is Bst DNA polymerase, exo(-) Bst polymerase, exo(-) Bca DNA polymerase, Bsu DNA polymerase, a DNA polymerase sold under the trademark VENT®, Klenow Fragment (exo-) DNA polymerase, or Therminator DNA polymerase. Further provided herein are methods wherein the least one terminator nucleotide comprises modifications of the r group of the 3' carbon of the deoxyribose. Further provided herein are methods wherein the at least one terminator nucleotide is selected from the group consisting of 3' blocked reversible terminator containing nucleotides, 3' unblocked reversible terminator containing nucleotides, terminators containing 2' modifications of deoxynucleotides, terminators containing modifications to the nitrogenous base of deoxynucleotides, and combinations thereof. Further provided herein are methods wherein the at least one terminator nucleotide is selected from the group consisting of dideoxynucleotides, inverted dideoxynucleotides, 3' biotinylated nucleotides, 3' amino nucleotides, 3'-phosphorylated nucleotides, 3'-O-methyl nucleotides, 3' carbon spacer nucleotides including 3' C3 spacer nucleotides, 3' C18 nucleotides, 3' Hexanediol spacer nucleotides, acyclonucleotides, and combinations thereof. Further provided herein are methods wherein the at least one terminator nucleotide are selected from the group consisting of nucleotides with modification to the alpha group, C3 spacer nucleotides, locked nucleic acids (LNA), inverted nucleic acids, 2' fluoro nucleotides, 3' phosphorylated nucleotides, 2'-O-Methyl modified nucleotides, and trans nucleic acids. Further provided herein are methods wherein the nucleotides with modification to the alpha group are alpha-thio dideoxynucleotides. Further provided herein are methods wherein the amplification primers are 4 to 70 nucleotides in length. Further provided herein are methods wherein the at least one amplification primer is 4 to 20 nucleotides in length. Further provided herein are methods wherein the method further comprising an additional amplification step using PCR. Further provided herein are methods wherein the at least one amplification primer comprises a randomized region. Further provided herein are methods wherein the randomized region is 4 to 20 nucleotides in length. Further provided herein are methods wherein the randomized region is 8 to 15 nucleotides in length. Further provided herein are methods wherein the amplification products are between about 50 and about 2000 nucleotides in length. Further provided herein are methods wherein the amplification products are between about 200 and about 1000 nucleotides in length. Further provided herein are methods wherein for identifying low frequency sequence variants. Further provided herein are methods wherein the low frequency sequence variants constitute ≥0.01% of the total sequences. Further provided herein are methods wherein the low frequency sequence variants constitute ≥0.05% of the total sequences. Further provided herein are methods wherein the low frequency sequence variants constitute ≥0.10% of the total sequences.

Provided herein are methods of sequencing a target nucleic acid molecule, the method comprising: contacting a sample comprising the target nucleic acid molecule, at least one amplification primer, at least one nucleic acid polymerase, and a mixture of nucleotides, wherein the mixture of nucleotides comprises at least one terminator nucleotide which terminates nucleic acid replication by the polymerase, and amplifying the target nucleic acid molecule to generate a plurality of terminated amplification products, wherein the replication proceeds by strand displacement replication; removing at least one terminator nucleotide from the terminated amplification products; ligating the molecules obtained in method to adaptors, thereby generating a library of amplification products; and sequencing the library of amplification products. Further provided herein are methods further comprising repairing ends and A-tailing. Further provided herein are methods wherein the target nucleic acid is DNA. Further provided herein are methods wherein the DNA is a cDNA. Further provided herein are methods wherein the DNA is a genomic DNA. Further provided herein are methods wherein the at least one amplification primer comprises two or more primers. Further provided herein are methods wherein the at least one amplification primer is a random primer. Further provided herein are methods wherein the at least one amplification primer comprise a barcode. Further provided herein are methods wherein the barcode comprises a cell barcode. Further provided herein are methods wherein the barcode comprises a sample barcode. Further provided herein are methods wherein the amplification primers comprise a unique molecular identifier (UMI). Further provided herein are methods wherein the method further comprises denaturing the target nucleic acid or genomic DNA before the initial primer annealing. Further provided herein are methods wherein denaturation is conducted under alkaline conditions followed by neutralization. Further provided herein are methods wherein the sample, the amplification primers, the nucleic acid polymerase, and the mixture of nucleotides are contained in a microfluidic device. Further provided herein are methods wherein the sample, the amplification primers, the nucleic acid polymerase, and the mixture of nucleotides are contained in a droplet. Further provided herein are methods wherein the sample is selected from tissue(s) samples, cells, biological fluid samples, bone marrow samples, semen samples, biopsy samples, cancer samples, tumor samples, cell lysate samples, forensic samples, archaeological samples, paleontological samples, infection samples, production samples, whole plants, plant parts, microbiota samples, viral preparations, soil samples, marine samples, freshwater samples, household or industrial samples, and combinations and isolates thereof. Further provided herein are methods wherein the biological fluids are selected from blood, urine, saliva, lymphatic fluid, cerebrospinal fluid (CSF), amniotic fluid, pleural fluid, pericardial fluid, ascites, and aqueous humor. Further provided herein are methods wherein the method further comprising an additional amplification step using PCR.

Provided herein are methods of sequencing a single cell, the method comprising: providing a cell lysate from the single cell; contacting the cell lysate with at least one amplification primer, at least one nucleic acid polymerase, and a mixture of nucleotides, wherein the mixture of nucleotides comprises at least one terminator nucleotide which terminates nucleic acid replication by the polymerase, and amplifying the target nucleic acid molecule to generate a plurality of terminated amplification products, wherein the replication proceeds by strand displacement replication; removing at least one terminator nucleotide from the terminated amplification products; ligating the molecules obtained in the method to adaptors, thereby generating a library of amplification products; and sequencing the library of amplification products. Further provided herein are methods wherein cell lysis is accompanied by proteolysis. Further provided herein are methods wherein the sample, at least one amplification primer, the nucleic acid polymerase, and the mixture of nucleotides are contained in a microfluidic device. Further provided herein are methods wherein the sample, the at least one amplification primer, the nucleic acid polymerase, and the mixture of nucleotides are contained in a droplet. Further provided herein are methods wherein the at least one amplification primer is attached to a solid support. Further provided herein are methods wherein the solid support is a bead. Further provided herein are methods wherein the at least one amplification primer is attached to a solid support via a cleavable linker. Further provided herein are methods wherein the at least one amplification primer comprises a barcode. Further provided herein are methods wherein the method further comprises cleaving the cleavable linker prior to amplification. Further provided herein are methods wherein the cell is selected from an animal cell, a plant cell, a fungal cell, a bacterial cell, and a protozoal cell. Further provided herein are methods wherein the animal cell is a human cell. Further provided herein are methods wherein the cell is selected from a cell from a preimplantation embryo, a stem cell, a fetal cell, a tumor cell, a suspected cancer cell, a cancer cell, a cell subjected to a gene editing procedure, a cell from a pathogenic organism, a cell obtained from a forensic sample, a cell obtained from an archeological sample, and a cell obtained from a paleontological sample. Further provided herein are methods wherein the preimplantation embryo cell is a blastomere. Further provided herein are methods wherein the blastomere is obtained from an eight-cell stage embryo produced by in vitro fertilization. Further provided herein are methods further comprising determining the presence of disease predisposing germline or somatic variants in the embryo cell. Further provided herein are methods wherein the pathogenic organism is a bacterium, a fungus or a protozoan. Further provided herein are methods wherein the cell obtained from a pathogenic organism is obtained from fluid taken from a patient, microbiota sample or an indwelling medical device. Further provided herein are methods further comprising the step of determining the identity of the pathogenic organism. Further provided herein are methods further comprising determining the presence of genetic variants responsible for resistance of the pathogenic organism to a treatment. Further provided herein are methods wherein the cell is a tumor cell, a suspected cancer cell, or a cancer cell. Further provided herein are methods further comprising determining the presence of one or more diagnostic or prognostic mutations. Further provided herein are methods further comprising determining the presence of germline or somatic variants responsible for resistance to a treatment. Further provided herein are methods wherein the cell is a cell subjected to a gene editing procedure. Further provided herein are methods further comprising determining the presence of unplanned mutations caused by the gene editing process. Further provided herein are methods further comprising determining the history of a cell lineage. Further provided herein are methods wherein for identifying low frequency sequence variants. Further provided herein are methods wherein the low frequency sequence variants constitute ≥0.01% of the total sequences. Further provided herein are methods wherein the low frequency sequence variants constitute ≥0.05% of the total sequences. Further provided herein are methods wherein the low frequency sequence variants constitute ≥0.10% of the total sequences. Further provided herein are methods wherein the method further comprising an additional amplification step using PCR.

Provided herein are methods of determining the mutagenicity of an environmental condition, the method comprising: exposing cells to the environmental condition; isolating single cells from the population; providing a cell lysate from a single cell; contacting the cell lysate with at least one amplification primer, at least one nucleic acid polymerase, and a mixture of nucleotides, wherein the mixture of nucleotides comprises at least one terminator nucleotide which terminates nucleic acid replication by the polymerase, and amplifying the target nucleic acid molecule to generate a plurality of terminated amplification products, wherein the replication proceeds by strand displacement replication; removing at least one terminator nucleotide from the terminated amplification products; ligating the molecules obtained in the in the method to adaptors, thereby generating a library of amplification products; and sequencing the library of amplification products, and comparing the sequences of amplification products to at least one reference sequence to identify mutations. Further provided herein are methods wherein the single cell is a human cell. Further provided herein are methods wherein environmental condition comprises a chemical substance. Further provided herein are methods wherein the environmental condition comprises radiation. Further provided herein are methods wherein the environmental condition comprises ultraviolet light. Further provided herein are methods wherein the single cells originate from liver, skin, kidney, blood, or lung. Further provided herein are methods wherein at least some of the amplification products comprise a barcode. Further provided herein are methods wherein the barcode comprises a cell barcode. Further provided herein are methods wherein the barcode comprises a sample barcode. Further provided herein are methods wherein at least some of the amplification primers comprise a unique molecular identifier (UMI). Further provided herein are methods wherein the method further comprising an additional amplification step using PCR.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1A:
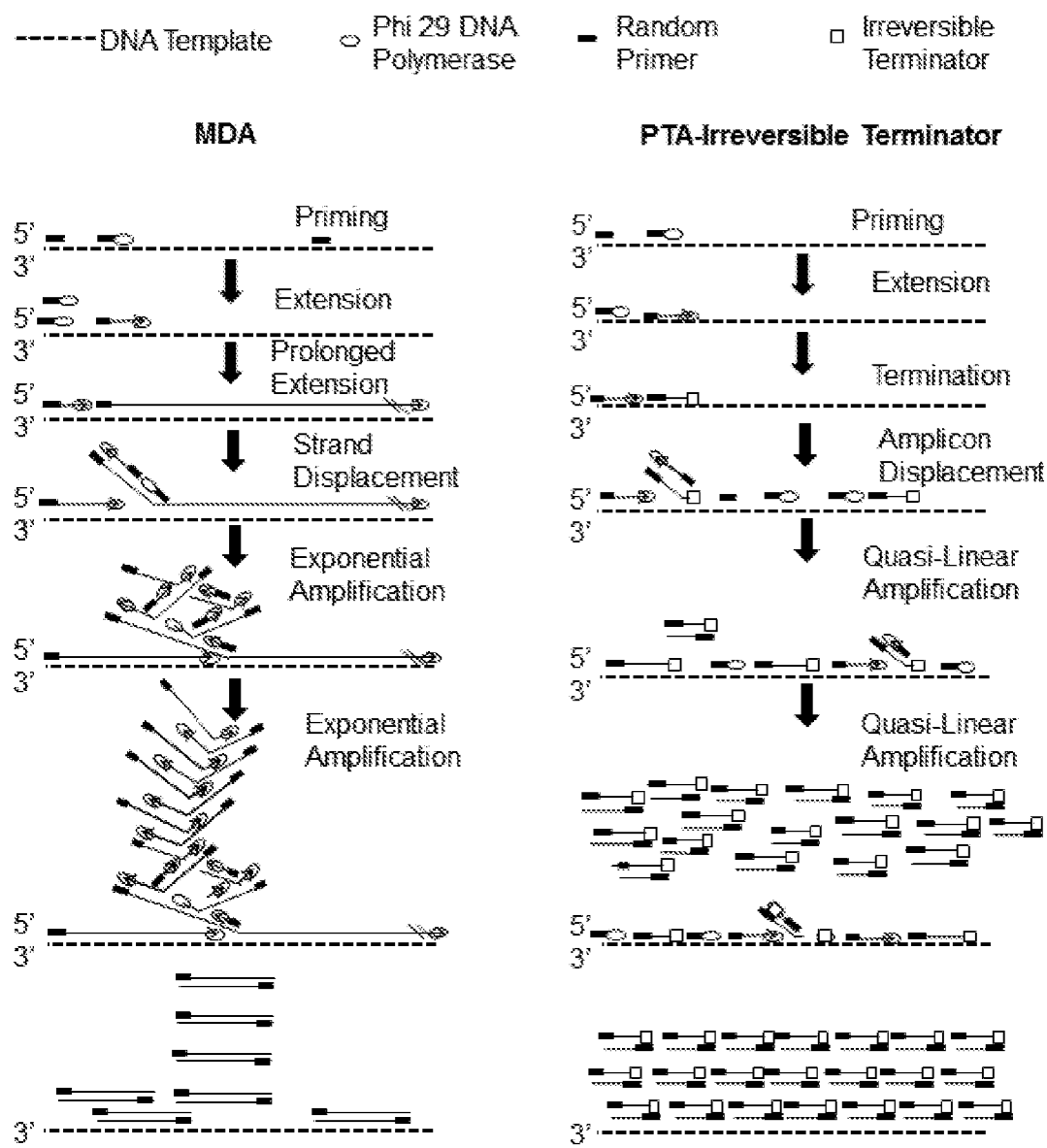
FIG. 1A illustrates a comparison of a prior multiple displacement amplification (MDA) method with one of the embodiments of the Primary Template-Directed Amplification (PTA) method, namely the PTA-Irreversible Terminator method.

There is a need to develop new scalable, accurate and efficient methods for nucleic acid amplification (including single-cell and multi-cell genome amplification) and sequencing which would overcome limitations in the current methods by increasing sequence representation, uniformity and accuracy in a reproducible manner. Provided herein are compositions and methods for providing accurate and scalable Primary Template-Directed Amplification (PTA) and sequencing. Further provided herein are methods of single nucleotide variant determination, copy number variation, clonotyping, and measurement of environmental mutagenicity. Such methods and compositions facilitate highly accurate amplification of target (or "template") nucleic acids, which increases accuracy and sensitivity of downstream applications, such as Next Generation Sequencing.

Definitions

Unless defined otherwise, all technical and scientific terms used herein have the same meaning as is commonly understood by one of ordinary skill in the art to which these inventions belong.

Throughout this disclosure, numerical features are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

The terms "subject" or "patient" or "individual", as used herein, refer to animals, including mammals, such as, e.g., humans, veterinary animals (e.g., cats, dogs, cows, horses, sheep, pigs, etc.) and experimental animal models of diseases (e.g., mice, rats). In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A practical Approach*, Volumes I and II (D. N. Glover ed. 1985); *Oligonucleotide Synthesis* (MJ. Gait ed. 1984); *Nucleic Acid Hybridization* (B. D. Hames & S. J. Higgins eds. (1985»; *Transcription and Translation* (B. D. Hames & S. J. Higgins, eds. (1984»; *Animal Cell Culture* (R. I. Freshney, ed. (1986»; *Immobilized Cells and Enzymes* (IRL Press, (1986»; B. Perbal, *A practical Guide To Molecular Cloning* (1984); F. M. Ausubel et al. (eds.), *Current Protocols in Molecular Biology*, John Wiley & Sons, Inc. (1994); among others.

The term "nucleic acid" encompasses multi-stranded, as well as single-stranded molecules. In double- or triple-stranded nucleic acids, the nucleic acid strands need not be coextensive (i.e., a double-stranded nucleic acid need not be double-stranded along the entire length of both strands). Nucleic acid templates described herein may be any size depending on the sample (from small cell-free DNA fragments to entire genomes), including but not limited to 50-300 bases, 100-2000 bases, 100-750 bases, 170-500 bases, 100-5000 bases, 50-10,000 bases, or 50-2000 bases in length. In some instances, templates are at least 50, 100, 200, 500, 1000, 2000, 5000, 10,000, 20,000 50,000, 100,000, 200,000, 500,000, 1,000,000 or more than 1,000,000 bases in length. Methods described herein provide for the amplification of nucleic acid acids, such as nucleic acid templates. Methods described herein additionally provide for the generation of isolated and at least partially purified nucleic acids and libraries of nucleic acids. Nucleic acids include but are not limited to those comprising DNA, RNA, circular RNA, cfDNA (cell free DNA), cfRNA (cell free RNA), siRNA (small interfering RNA), cffDNA (cell free fetal DNA), mRNA, tRNA, rRNA, miRNA (microRNA), synthetic polynucleotides, polynucleotide analogues, any other nucleic acid consistent with the specification, or any combinations thereof. The length of polynucleotides, when provided, are described as the number of bases and abbreviated, such as nt (nucleotides), bp (bases), kb (kilobases), or Gb (gigabases).

The term "droplet" as used herein refers to a volume of liquid on a droplet actuator. Droplets in some instances, for example, be aqueous or non-aqueous or may be mixtures or emulsions including aqueous and non-aqueous components. For non-limiting examples of droplet fluids that may be subjected to droplet operations, see, e.g., Int. Pat. Appl. Pub. No. WO2007/120241. Any suitable system for forming and manipulating droplets can be used in the embodiments presented herein. For example, in some instances a droplet actuator is used. For non-limiting examples of droplet actuators which can be used, see, e.g., U.S. Pat. Nos. 6,911,132, 6,977,033, 6,773,566, 6,565,727, 7,163,612, 7,052,244, 7,328,979, 7,547,380, 7,641,779, U.S. Pat. Appl. Pub. Nos. US20060194331, US20030205632, US20060164490, US20070023292, US20060039823, US20080124252, US20090283407, US20090192044, US20050179746, US20090321262, US20100096266, US20110048951, Int. Pat. Appl. Pub. No. WO2007/120241. In some instances, beads are provided in a droplet, in a droplet operations gap, or on a droplet operations surface. In some instances, beads are provided in a reservoir that is external to a droplet operations gap or situated apart from a droplet operations surface, and the reservoir may be associated with a flow path that permits a droplet including the beads to be brought into a droplet operations gap or into contact with a droplet operations surface. Non-limiting examples of droplet actuator techniques for immobilizing magnetically responsive beads and/or non-magnetically responsive beads and/or conducting droplet operations protocols using beads are described in U.S. Pat. Appl. Pub. No. US20080053205, Int. Pat. Appl. Pub. No. WO2008/098236, WO2008/134153, WO2008/116221, WO2007/120241. Bead characteristics may be employed in the multiplexing embodiments of the methods described herein. Examples of beads having characteristics suitable for multiplexing, as well as methods of detecting and analyzing signals emitted from such beads, may be found in U.S. Pat. Appl. Pub. No. US20080305481, US20080151240, US20070207513, US20070064990, US20060159962, US20050277197, US20050118574.

As used herein, the term "unique molecular identifier (UMI)" refers to a unique nucleic acid sequence that is attached to each of a plurality of nucleic acid molecules. When incorporated into a nucleic acid molecule, an UMI in some instances is used to correct for subsequent amplification bias by directly counting UMIs that are sequenced after amplification. The design, incorporation and application of UMIs is described, for example, in Int. Pat. Appl. Pub. No. WO 2012/142213, Islam et al. Nat. Methods (2014) 11:163-166, and Kivioja, T. et al. Nat. Methods (2012) 9: 72-74.

As used herein, the term "barcode" refers to a nucleic acid tag that can be used to identify a sample or source of the nucleic acid material. Thus, where nucleic acid samples are derived from multiple sources, the nucleic acids in each nucleic acid sample are in some instances tagged with different nucleic acid tags such that the source of the sample can be identified. Barcodes, also commonly referred to indexes, tags, and the like, are well known to those of skill in the art. Any suitable barcode or set of barcodes can be used. See, e.g., non-limiting examples provided in U.S. Pat. No. 8,053,192 and Int. Pat. Appl. Pub. No. WO2005/068656. Barcoding of single cells can be performed as described, for example, in U.S. Pat. Appl. Pub. No. 2013/0274117.

The terms "solid surface," "solid support" and other grammatical equivalents herein refer to any material that is appropriate for or can be modified to be appropriate for the attachment of the primers, barcodes and sequences described herein. Exemplary substrates include, but are not limited to, glass and modified or functionalized glass, plastics (including acrylics, polystyrene and copolymers of styrene and other materials, polypropylene, polyethylene, polybutylene, polyurethanes, Teflon™, etc.), polysaccharides, nylon, nitrocellulose, ceramics, resins, silica, silica-based materials (e.g., silicon or modified silicon), carbon, metals, inorganic glasses, plastics, optical fiber bundles, and a variety of other polymers. In some embodiments, the solid support comprises a patterned surface suitable for immobilization of primers, barcodes and sequences in an ordered pattern.

As used herein, the term "biological sample" includes, but is not limited to, tissues, cells, biological fluids and isolates thereof. Cells or other samples used in the methods described herein are in some instances isolated from human patients, animals, plants, soil or other samples comprising microbes such as bacteria, fungi, protozoa, etc. In some instances, the biological sample is of human origin. In some instances, the biological is of non-human origin. The cells in some instances undergo PTA methods described herein and sequencing. Variants detected throughout the genome or at specific locations can be compared with all other cells isolated from that subject to trace the history of a cell lineage for research or diagnostic purposes.

Primary Template-Directed Amplification

Figure 1B:
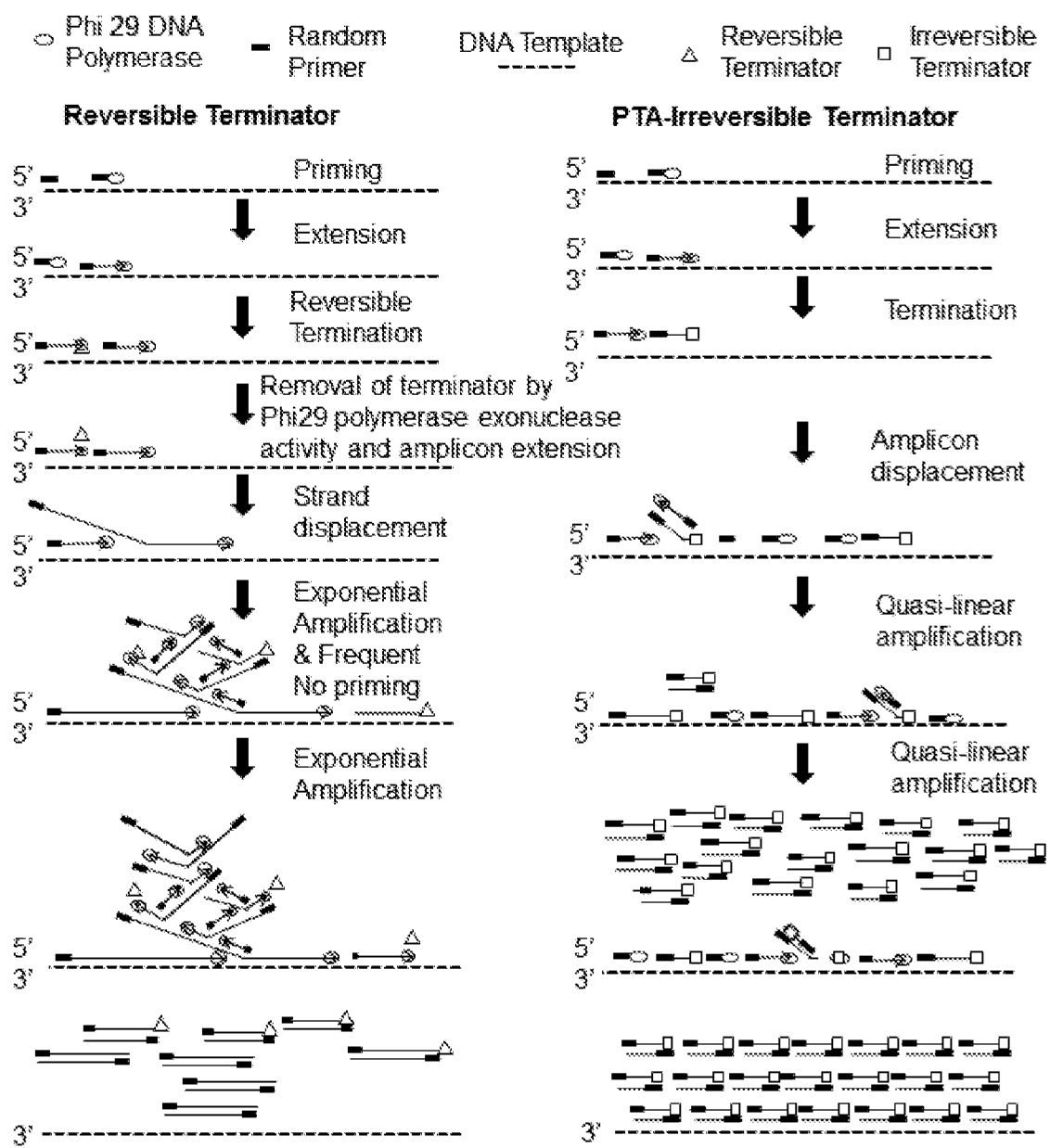
FIG. 1B illustrates a comparison of the PTA-Irreversible Terminator method with a different embodiment, namely the PTA-Reversible Terminator method.

Described herein are nucleic acid amplification methods, such as "Primary Template-Directed Amplification (PTA)." For example, the PTA methods described herein are schematically represented in FIGS. 1A-1D. With the PTA method, amplicons are preferentially generated from the primary template ("direct copies") using a polymerase (e.g., a strand displacing polymerase). Consequently, errors are propagated at a lower rate from daughter amplicons during subsequent amplifications compared to MDA. The result is an easily executed method that, unlike existing WGA protocols, can amplify low DNA input including the genomes of single cells with high coverage breadth and uniformity in an accurate and reproducible manner. Moreover, the terminated amplification products can undergo direction ligation after removal of the terminators, allowing for the attachment of a cell barcode to the amplification primers so that products from all cells can be pooled after undergoing parallel amplification reactions (FIG. 1B).

Described herein are methods employing nucleic acid polymerases with strand displacement activity for amplification. In some instances, such polymerases comprise strand displacement activity and low error rate. In some instances, such polymerases comprise strand displacement activity and proofreading exonuclease activity, such as 3'->5' proofreading activity. In some instances, nucleic acid polymerases are used in conjunction with other components such as reversible or irreversible terminators, or additional strand displacement factors. In some instances, the polymerase has strand displacement activity, but does not have exonuclease proofreading activity. For example, in some instances such polymerases include bacteriophage phi29 (Φ29) polymerase, which also has very low error rate that is the result of the 3'->5' proofreading exonuclease activity (see, e.g., U.S. Pat. Nos. 5,198,543 and 5,001,050). In some instances, non-limiting examples of strand displacing nucleic acid polymerases include, e.g., genetically modified phi29 (Φ29) DNA polymerase, Klenow Fragment of DNA polymerase I (Jacobsen et al., Eur. J. Biochem. 45:623-627 (1974)), phage M2 DNA polymerase (Matsumoto et al., Gene 84:247 (1989)), phage phiPRD1 DNA polymerase (Jung et al., Proc. Natl. Acad. Sci. USA 84:8287 (1987); Zhu and Ito, Biochim. Biophys. Acta. 1219:267-276 (1994)), Bst DNA polymerase (e.g., Bst large fragment DNA polymerase (Exo(-) Bst; Aliotta et al., Genet. Anal. (Netherlands) 12:185-195 (1996)), exo(-)Bca DNA polymerase (Walker and Linn, Clinical Chemistry 42:1604-1608 (1996)), Bsu DNA polymerase, a DNA polymerase sold under the trademark VENT® including an exo-DNA polymerase sold under trademark VENT®(Kong et al., J. Biol. Chem. 268:1965-1975 (1993)), polymerases sold under trademark DEEP VENT® including an exo-DNA polymerase sold under trademark DEEP VENT®, a DNA polymerase sold under trademark ISOPOL™, DNA polymerase I, a DNA polymerase sold under trademark THERMINATOR™, T5 DNA polymerase (Chatterjee et al., Gene 97:13-19 (1991)), Sequenase (U.S. Biochemicals), T7 DNA polymerase, T7-Sequenase, T7 gp5 DNA polymerase, PRD1 DNA polymerase, T4 DNA polymerase (Kaboord and Benkovic, Curr. Biol. 5:149-157 (1995)). Additional strand displacing nucleic acid polymerases are also compatible with the methods described herein. The ability of a given polymerase to carry out strand displacement replication can be determined, for example, by using the polymerase in a strand displacement replication assay (e.g., as disclosed in U.S. Pat. No. 6,977,148). Such assays in some instances are performed at a temperature suitable for optimal activity for the enzyme being used, for example, 32° C. for phi29 DNA polymerase, from 46° C. to 64° C. for exo(-) Bst DNA polymerase, or from about 60° C. to 70° C. for an enzyme from a hyperthermophylic organism. Another useful assay for selecting a polymerase is the primer-block assay described in Kong et al., J. Biol. Chem. 268:1965-1975 (1993). The assay consists of a primer extension assay using an M13 ssDNA template in the presence or absence of an oligonucleotide that is hybridized upstream of the extending primer to block its progress. Other enzymes capable of displacement the blocking primer in this assay are in some instances useful for the disclosed method. In some instances, polymerases incorporate dNTPs and terminators at approximately equal rates. In some instances, the ratio of rates of incorporation for dNTPs and terminators for a polymerase described herein are about 1:1, about 1.5:1, about 2:1, about 3:1 about 4:1 about 5:1, about 10:1, about 20:1 about 50:1, about 100:1, about 200:1, about 500:1, or about 1000:1. In some instances, the ratio of rates of incorporation for dNTPs and terminators for a polymerase described herein are 1:1 to 1000:1, 2:1 to 500:1, 5:1 to 100:1, 10:1 to 1000:1, 100:1 to 1000:1, 500:1 to 2000:1, 50:1 to 1500:1, or 25:1 to 1000:1.

Described herein are methods of amplification wherein strand displacement can be facilitated through the use of a strand displacement factor, such as, e.g., helicase. Such factors are in some instances used in conjunction with additional amplification components, such as polymerases, terminators, or other component. In some instances, a strand displacement factor is used with a polymerase that does not have strand displacement activity. In some instances, a strand displacement factor is used with a polymerase having strand displacement activity. Without being bound by theory, strand displacement factors may increase the rate that smaller, double stranded amplicons are reprimed. In some instances, any DNA polymerase that can perform strand displacement replication in the presence of a strand displacement factor is suitable for use in the PTA method, even if the DNA polymerase does not perform strand displacement replication in the absence of such a factor. Strand displacement factors useful in strand displacement replication in some instances include (but are not limited to) BMRF1 polymerase accessory subunit (Tsurumi et al., J. Virology 67(12):7648-7653 (1993)), adenovirus DNA-binding protein (Zijderveld and van der Vliet, J. Virology 68(2): 1158-1164 (1994)), herpes simplex viral protein ICP8 (Boehmer and Lehman, J. Virology 67(2):711-715 (1993); Skaliter and Lehman, Proc. Natl. Acad. Sci. USA 91(22):10665-10669 (1994)); single-stranded DNA binding proteins (SSB; Rigler and Romano, J. Biol. Chem. 270:8910-8919 (1995)); phage T4 gene 32 protein (Villemain and Giedroc, Biochemistry 35:14395-14404 (1996); T7 helicase-primase; T7 gp2.5 SSB protein; Tte-UvrD (from *Thermoanaerobacter tengcongensis*), calf thymus helicase (Siegel et al., J. Biol. Chem. 267:13629-13635 (1992)); bacterial SSB (e.g., *E. coli* SSB), Replication Protein A (RPA) in eukaryotes, human mitochondrial SSB (mtSSB), and recombinases, (e.g., Recombinase A (RecA) family proteins, T4 UvsX, Sak4 of Phage HK620, Rad51, Dmc1, or Radb). Combinations of factors that facilitate strand displacement and priming are also consistent with the methods described herein. For example, a helicase is used in conjunction with a polymerase. In some instances, the PTA method comprises use of a single-strand DNA binding protein (SSB, T4 gp32, or other single stranded DNA binding protein), a helicase, and a polymerase (e.g., SauDNA polymerase, Bsu polymerase, Bst2.0, GspM, GspM2.0, GspSSD, or other suitable polymerase). In some instances, reverse transcriptases are used in conjunction with the strand displacement factors described herein.

Described herein are amplification methods comprising use of terminator nucleotides, polymerases, and additional factors or conditions. For example, such factors are used in some instances to fragment the nucleic acid template(s) or amplicons during amplification. In some instances, such factors comprise endonucleases. In some instances, factors comprise transposases. In some instances, mechanical shearing is used to fragment nucleic acids during amplification. In some instances, nucleotides are added during amplification that may be fragmented through the addition of additional proteins or conditions. For example, uracil is incorporated into amplicons; treatment with uracil D-glycosylase fragments nucleic acids at uracil-containing positions. Additional systems for selective nucleic acid fragmentation are also in some instances employed, for example an engineered DNA glycosylase that cleaves modified cytosine-pyrene base pairs. (Kwon, et al. Chem Biol. 2003, 10(4), 351)

Described herein are amplification methods comprising use of terminator nucleotides, which terminate nucleic acid replication thus decreasing the size of the amplification products. Such terminators are in some instances used in conjunction with polymerases, strand displacement factors, or other amplification components described herein. In some instances, terminator nucleotides reduce or lower the efficiency of nucleic acid replication. Such terminators in some instances reduce extension rates by at least 99.9%, 99%, 98%, 95%, 90%, 85%, 80%, 75%, 70%, or at least 65%. Such terminators in some instances reduce extension rates by 50%-90%, 60%-80%, 65%-90%, 70%-85%, 60%-90%, 70%-99%, 80%-99%, or 50%-80%. In some instances terminators reduce the average amplicon product length by at least 99.9%, 99%, 98%, 95%, 90%, 85%, 80%, 75%, 70%, or at least 65%. Terminators in some instances reduce the average amplicon length by 50%-90%, 60%-80%, 65%-90%, 70%-85%, 60%-90%, 70%-99%, 80%-99%, or 50%-80%. In some instances, amplicons comprising terminator nucleotides form loops or hairpins which reduce a polymerase's ability to use such amplicons as templates. Use of terminators in some instances slows the rate of amplification at initial amplification sites through the incorporation of terminator nucleotides (e.g., dideoxynucleotides that have been modified to make them exonuclease-resistant to terminate DNA extension), resulting in smaller amplification products. By producing smaller amplification products than the currently used methods (e.g., average length of 50-2000 nucleotides in length for PTA methods as compared to an average product length of >10,000 nucleotides for MDA methods) PTA amplification products in some instances undergo direct ligation of adapters without the need for fragmentation, allowing for efficient incorporation of cell barcodes and unique molecular identifiers (UMI) (see FIGS. 1D, 2B-3E, 9, 10A, and 10B).

Terminator nucleotides are present at various concentrations depending on factors such as polymerase, template, or other factors. For example, the amount of terminator nucleotides in some instances is expressed as a ratio of non-terminator nucleotides to terminator nucleotides in a method described herein. Such concentrations in some instances allow control of amplicon lengths. In some instances, the ratio of non-terminator to terminator nucleotides is about 2:1, 5:1, 7:1, 10:1, 20:1, 50:1, 100:1, 200:1, 500:1, 1000:1, 2000:1, or 5000:1. In some instances the ratio of non-terminator to terminator nucleotides is 2:1-10:1, 5:1-20:1, 10:1-100:1, 20:1-200:1, 50:1-1000:1, 50:1-500:1, 75:1-150:1, or 100:1-500:1. In some instances, at least one of the nucleotides present during amplification using a method described herein is a terminator nucleotide. Each terminator need not be present at approximately the same concentration; in some instances, ratios of each terminator present in a method described herein are optimized for a particular set of reaction conditions, sample type, or polymerase. Without being bound by theory, each terminator may possess a different efficiency for incorporation into the growing polynucleotide chain of an amplicon, in response to pairing with the corresponding nucleotide on the template strand. For example, in some instances a terminator pairing with cytosine is present at about 3%, 5%, 10%, 15%, 20%, 25%, or 50% higher concentration than the average terminator concentration. In some instances a terminator pairing with thymine is present at about 3%, 5%, 10%, 15%, 20%, 25%, or 50% higher concentration than the average terminator concentration. In some instances a terminator pairing with guanine is present at about 3%, 5%, 10%, 15%, 20%, 25%, or 50% higher concentration than the average terminator concentration. In some instances a terminator pairing with adenine is present at about 3%, 5%, 10%, 15%, 20%, 25%, or 50% higher concentration than the average terminator concentration. In some instances a terminator pairing with uracil is present at about 3%, 5%, 10%, 15%, 20%, 25%, or 50% higher concentration than the average terminator concentration. Any nucleotide capable of terminating nucleic acid extension by a nucleic acid polymerase in some instances is used as a terminator nucleotide in the methods described herein. In some instances, a reversible terminator is used to terminate nucleic acid replication. In some instances, a non-reversible terminator is used to terminate nucleic acid replication. In some instances, non-limited examples of terminators include reversible and non-reversible nucleic acids and nucleic acid analogs, such as, e.g., 3' blocked reversible terminator comprising nucleotides, 3' unblocked reversible terminator comprising nucleotides, terminators comprising 2' modifications of deoxynucleotides, terminators comprising modifications to the nitrogenous base of deoxynucleotides, or any combination thereof. In one embodiment, terminator nucleotides are dideoxynucleotides. Other nucleotide modifications that terminate nucleic acid replication and may be suitable for practicing the invention include, without limitation, any modifications of the r group of the 3' carbon of the deoxyribose such as inverted dideoxynucleotides, 3' biotinylated nucleotides, 3' amino nucleotides, 3'-phosphorylated nucleotides, 3'-O-methyl nucleotides, 3' carbon spacer nucleotides including 3' C3 spacer nucleotides, 3' C18 nucleotides, 3' Hexanediol spacer nucleotides, acyclonucleotides, and combinations thereof. In some instances, terminators are polynucleotides comprising 1, 2, 3, 4, or more bases in length. In some instances, terminators do not comprise a detectable moiety or tag (e.g., mass tag, fluorescent tag, dye, radioactive atom, or other detectable moiety). In some instances, terminators do not comprise a chemical moiety allowing for attachment of a detectable moiety or tag (e.g., "click" azide/alkyne, conjugate addition partner, or other chemical handle for attachment of a tag). In some instances, all terminator nucleotides comprise the same modification that reduces amplification to at region (e.g., the sugar moiety, base moiety, or phosphate moiety) of the nucleotide. In some instances, at least one terminator has a different modification that reduces amplification. In some instances, all terminators have a substantially similar fluorescent excitation or emission wavelengths. In some instances, terminators without modification to the phosphate group are used with polymerases that do not have exonuclease proofreading activity. Terminators, when used with polymerases which have 3'->5' proofreading exonuclease activity (such as, e.g., phi29) that can remove the terminator nucleotide, are in some instances further modified to make them exonuclease-resistant. For example, dideoxynucleotides are modified with an alpha-thio group that creates a phosphorothioate linkage which makes these nucleotides resistant to the 3'->5' proofreading exonuclease activity of nucleic acid polymerases. Such modifications in some instances reduce the exonuclease proofreading activity of polymerases by at least 99.5%, 99%, 98%, 95%, 90%, or at least 85%. Non-limiting examples of other terminator nucleotide modifications providing resistance to the 3'->5' exonuclease activity include in some instances: nucleotides with modification to the alpha group, such as alpha-thio dideoxynucleotides creating a phosphorothioate bond, C3 spacer nucleotides, locked nucleic acids (LNA), inverted nucleic acids, 2' Fluoro bases, 3' phosphorylation, 2'-O-Methyl modifications (or other 2'-O-alkyl modification), propyne-modified bases (e.g., deoxycytosine, deoxyuridine), L-DNA nucleotides, L-RNA nucleotides, nucleotides with inverted linkages (e.g., 5'-5' or 3'-3'), 5' inverted bases (e.g., 5' inverted 2',3'-dideoxy dT), methylphosphonate backbones, and trans nucleic acids. In some instances, nucleotides with modification include base-modified nucleic acids comprising free 3' OH groups (e.g., 2-nitrobenzyl alkylated HOMedU triphosphates, bases comprising modification with large chemical groups, such as solid supports or other large moiety). In some instances, a polymerase with strand displacement activity but without 3'->5'exonuclease proofreading activity is used with terminator nucleotides with or without modifications to make them exonuclease resistant. Such nucleic acid polymerases include, without limitation, Bst DNA polymerase, Bsu DNA polymerase, an (exo-) DNA polymerase sold under trademark DEEP VENT®, Klenow Fragment (exo-) DNA polymerase, a DNA polymerase sold under trademark THERMINATOR , and an (exo-) DNA polymerase sold under trademark VENT®.

Primers and Amplicon Libraries

Described herein are amplicon libraries resulting from amplification of at least one target nucleic acid molecule. Such libraries are in some instances generated using the methods described herein, such as those using terminators. Such methods comprise use of strand displacement polymerases or factors, terminator nucleotides (reversible or irreversible), or other features and embodiments described herein. In some instances, amplicon libraries generated by use of terminators described herein are further amplified in a subsequent amplification reaction (e.g., PCR). In some instances, subsequent amplification reactions do not comprise terminators. In some instances, amplicon libraries comprise polynucleotides, wherein at least 50%, 60%, 70%, 80%, 90%, 95%, or at least 98% of the polynucleotides comprise at least one terminator nucleotide. In some instances, the amplicon library comprises the target nucleic acid molecule from which the amplicon library was derived. The amplicon library comprises a plurality of polynucleotides, wherein at least some of the polynucleotides are direct copies (e.g., replicated directly from a target nucleic acid molecule, such as genomic DNA, RNA, or other target nucleic acid). For example, at least 5%, 10%, 20%, 30%, 40%, 50%, 60%, 70%, 80%, 90%, 95% or more than 95% of the amplicon polynucleotides are direct copies of the at least one target nucleic acid molecule. In some instances, at least 5% of the amplicon polynucleotides are direct copies of the at least one target nucleic acid molecule. In some instances, at least 10% of the amplicon polynucleotides are direct copies of the at least one target nucleic acid molecule. In some instances, at least 15% of the amplicon polynucleotides are direct copies of the at least one target nucleic acid molecule. In some instances, at least 20% of the amplicon polynucleotides are direct copies of the at least one target nucleic acid molecule. In some instances, at least 50% of the amplicon polynucleotides are direct copies of the at least one target nucleic acid molecule. In some instances, 3%-5%, 3-10%, 5%-10%, 10%-20%, 20%-30%, 30%-40%, 5%-30%, 10%-50%, or 15%-75% of the amplicon polynucleotides are direct copies of the at least one target nucleic acid molecule. In some instances, at least some of the polynucleotides are direct copies of the target nucleic acid molecule, or daughter (a first copy of the target nucleic acid) progeny. For example, at least 5%, 10%, 20%, 30%, 40%, 50%, 60%, 70%, 80%, 90%, 95% or more than 95% of the amplicon polynucleotides are direct copies of the at least one target nucleic acid molecule or daughter progeny. In some instances, at least 5% of the amplicon polynucleotides are direct copies of the at least one target nucleic acid molecule or daughter progeny. In some instances, at least 10% of the amplicon polynucleotides are direct copies of the at least one target nucleic acid molecule or daughter progeny. In some instances, at least 20% of the amplicon polynucleotides are direct copies of the at least one target nucleic acid molecule or daughter progeny. In some instances, at least 30% of the amplicon polynucleotides are direct copies of the at least one target nucleic acid molecule or daughter progeny. In some instances, 3%-5%, 3%-10%, 5%-10%, 10%-20%, 20%-30%, 30%-40%, 5%-30%, 10%-50%, or 15%-75% of the amplicon polynucleotides are direct copies of the at least one target nucleic acid molecule or daughter progeny. In some instances, direct copies of the target nucleic acid are 50-2500, 75-2000, 50-2000, 25-1000, 50-1000, 500-2000, or 50-2000 bases in length. In some instances, daughter progeny are 1000-5000, 2000-5000, 1000-10,000, 2000-5000, 1500-5000, 3000-7000, or 2000-7000 bases in length. In some instances, the average length of PTA amplification products is 25-3000 nucleotides in length, 50-2500, 75-2000, 50-2000, 25-1000, 50-1000, 500-2000, or 50-2000 bases in length. In some instance, amplicons generated from PTA are no more than 5000, 4000, 3000, 2000, 1700, 1500, 1200, 1000, 700, 500, or no more than 300 bases in length. In some instance, amplicons generated from PTA are 1000-5000, 1000-3000, 200-2000, 200-4000, 500-2000, 750-2500, or 1000-2000 bases in length. Amplicon libraries generated using the methods described herein in some instances comprise at least 1000, 2000, 5000, 10,000, 100,000, 200,000, 500,000 or more than 500,000 amplicons comprising unique sequences. In some instances, the library comprises at least 100, 200, 300, 400, 500, 600, 700, 800, 900, 1000, 1100, 1200, 1300, 1400, 1500, 2000, 2500, 3000, or at least 3500 amplicons. In some instances, at least 5%, 10%, 15%, 20%, 25%, 30% or more than 30% of amplicon polynucleotides having a length of less than 1000 bases are direct copies of the at least one target nucleic acid molecule. In some instances, at least 5%, 10%, 15%, 20%, 25%, 30% or more than 30% of amplicon polynucleotides having a length of no more than 2000 bases are direct copies of the at least one target nucleic acid molecule. In some instances, at least 5%, 10%, 15%, 20%, 25%, 30% or more than 30% of amplicon polynucleotides having a length of 3000-5000 bases are direct copies of the at least one target nucleic acid molecule. In some instances, the ratio of direct copy amplicons to target nucleic acid molecules is at least 10:1, 100:1, 1000:1, 10,000:1, 100,000:1, 1,000,000:1, 10,000,000:1, or more than 10,000,000:1. In some instances, the ratio of direct copy amplicons to target nucleic acid molecules is at least 10:1, 100:1, 1000:1, 10,000:1, 100,000:1, 1,000,000:1, 10,000,000:1, or more than 10,000,000:1, wherein the direct copy amplicons are no more than 700-1200 bases in length. In some instances, the ratio of direct copy amplicons and daughter amplicons to target nucleic acid molecules is at least 10:1, 100:1, 1000:1, 10,000:1, 100,000:1, 1,000,000:1, 10,000,000:1, or more than 10,000,000:1. In some instances, the ratio of direct copy amplicons and daughter amplicons to target nucleic acid molecules is at least 10:1, 100:1, 1000:1, 10,000:1, 100,000:1, 1,000,000:1, 10,000,000:1, or more than 10,000,000:1, wherein the direct copy amplicons are 700-1200 bases in length, and the daughter amplicons are 2500-6000 bases in length. In some instances, the library comprises about 50-10,000, about 50-5,000, about 50-2500, about 50-1000, about 150-2000, about 250-3000, about 50-2000, about 500-2000, or about 500-1500 amplicons which are direct copies of the target nucleic acid molecule. In some instances, the library comprises about 50-10,000, about 50-5,000, about 50-2500, about 50-1000, about 150-2000, about 250-3000, about 50-2000, about 500-2000, or about 500-1500 amplicons which are direct copies of the target nucleic acid molecule or daughter amplicons. Amplicon libraries generated using the methods described herein are in some instances subjected to additional steps, such as adapter ligation and further PCR amplification. In some instances, such additional steps precede a sequencing step.

Amplicon libraries of polynucleotides generated from the PTA methods and compositions (terminators, polymerases, etc.) described herein in some instances have increased uniformity. Uniformity, in some instances, is described using a Lorenz curve (e.g., FIG. 5C), or other such method. Such increases in some instances lead to lower sequencing reads needed for the desired coverage of a target nucleic acid molecule (e.g., genomic DNA, RNA, or other target nucleic acid molecule). For example, no more than 50% of a cumulative fraction of polynucleotides comprises sequences of at least 80% of a cumulative fraction of sequences of the target nucleic acid molecule. In some instances, no more than 50% of a cumulative fraction of polynucleotides comprises sequences of at least 60% of a cumulative fraction of sequences of the target nucleic acid molecule. In some instances, no more than 50% of a cumulative fraction of polynucleotides comprises sequences of at least 70% of a cumulative fraction of sequences of the target nucleic acid molecule. In some instances, no more than 50% of a cumulative fraction of polynucleotides comprises sequences of at least 90% of a cumulative fraction of sequences of the target nucleic acid molecule. In some instances, uniformity is described using a Gini index (wherein an index of 0 represents perfect equality of the library and an index of 1 represents perfect inequality). In some instances, amplicon libraries described herein have a Gini index of no more than 0.55, 0.50, 0.45, 0.40, or 0.30. In some instances, amplicon libraries described herein have a Gini index of no more than 0.50. In some instances, amplicon libraries described herein have a Gini index of no more than 0.40. Such uniformity metrics in some instances are dependent on the number of reads obtained. For example no more than 100 million, 200 million, 300 million, 400 million, or no more than 500 million reads are obtained. In some instances, the read length is about 50, 75, 100, 125, 150, 175, 200, 225, or about 250 bases in length. In some instances, uniformity metrics are dependent on the depth of coverage of a target nucleic acid. For example, the average depth of coverage is about 10×, 15×, 20×, 25×, or about 30×. In some instances, the average depth of coverage is 10-30×, 20-50×, 5-40×, 20-60×, 5-20×, or 10-20×. In some instances, amplicon libraries described herein have a Gini index of no more than 0.55, wherein about 300 million reads was obtained. In some instances, amplicon libraries described herein have a Gini index of no more than 0.50, wherein about 300 million reads was obtained. In some instances, amplicon libraries described herein have a Gini index of no more than 0.45, wherein about 300 million reads was obtained. In some instances, amplicon libraries described herein have a Gini index of no more than 0.55, wherein no more than 300 million reads was obtained. In some instances, amplicon libraries described herein have a Gini index of no more than 0.50, wherein no more than 300 million reads was obtained. In some instances, amplicon libraries described herein have a Gini index of no more than 0.45, wherein no more than 300 million reads was obtained. In some instances, amplicon libraries described herein have a Gini index of no more than 0.55, wherein the average depth of sequencing coverage is about 15×. In some instances, amplicon libraries described herein have a Gini index of no more than 0.50, wherein the average depth of sequencing coverage is about 15×. In some instances, amplicon libraries described herein have a Gini index of no more than 0.45, wherein the average depth of sequencing coverage is about 15×. In some instances, amplicon libraries described herein have a Gini index of no more than 0.55, wherein the average depth of sequencing coverage is at least 15×. In some instances, amplicon libraries described herein have a Gini index of no more than 0.50, wherein the average depth of sequencing coverage is at least 15×. In some instances, amplicon libraries described herein have a Gini index of no more than 0.45, wherein the average depth of sequencing coverage is at least 15×. In some instances, amplicon libraries described herein have a Gini index of no more than 0.55, wherein the average depth of sequencing coverage is no more than 15×. In some instances, amplicon libraries described herein have a Gini index of no more than 0.50, wherein the average depth of sequencing coverage is no more than 15×. In some instances, amplicon libraries described herein have a Gini index of no more than 0.45, wherein the average depth of sequencing coverage is no more than 15×. Uniform amplicon libraries generated using the methods described herein are in some instances subjected to additional steps, such as adapter ligation and further PCR amplification. In some instances, such additional steps precede a sequencing step.

Primers comprise nucleic acids used for priming the amplification reactions described herein. Such primers in some instances include, without limitation, random deoxynucleotides of any length with or without modifications to make them exonuclease resistant, random ribonucleotides of any length with or without modifications to make them exonuclease resistant, modified nucleic acids such as locked nucleic acids, DNA or RNA primers that are targeted to a specific genomic region, and reactions that are primed with enzymes such as primase. In the case of whole genome PTA, it is preferred that a set of primers having random or partially random nucleotide sequences be used. In a nucleic acid sample of significant complexity, specific nucleic acid sequences present in the sample need not be known and the primers need not be designed to be complementary to any particular sequence. Rather, the complexity of the nucleic acid sample results in a large number of different hybridization target sequences in the sample, which will be complementary to various primers of random or partially random sequence. The complementary portion of primers for use in PTA are in some instances fully randomized, comprise only a portion that is randomized, or be otherwise selectively randomized. The number of random base positions in the complementary portion of primers in some instances, for example, is from 20% to 100% of the total number of nucleotides in the complementary portion of the primers. In some instances, the number of random base positions in the complementary portion of primers is 10% to 90%, 15-95%, 20%-100%, 30%-100%, 50%-100%, 75-100% or 90-95% of the total number of nucleotides in the complementary portion of the primers. In some instances, the number of random base positions in the complementary portion of primers is at least 10%, 20%, 30%, 40%, 50%, 60%, 70%, 80%, or at least 90% of the total number of nucleotides in the complementary portion of the primers. Sets of primers having random or partially random sequences are in some instances synthesized using standard techniques by allowing the addition of any nucleotide at each position to be randomized. In some instances, sets of primers are composed of primers of similar length and/or hybridization characteristics. In some instances, the term "random primer" refers to a primer which can exhibit four-fold degeneracy at each position. In some instances, the term "random primer" refers to a primer which can exhibit three-fold degeneracy at each position. Random primers used in the methods described herein in some instances comprise a random sequence that is 3, 4, 5, 6, 7, 8, 10, 11, 12, 13, 14, 15, 16, 17, 18, 19, 20, or more bases in length. In some instances, primers comprise random sequences that are 3-20, 5-15, 5-20, 6-12, or 4-10 bases in length. Primers may also comprise non-extendable elements that limit subsequent amplification of amplicons generated thereof. For example, primers with non-extendable elements in some instances comprise terminators. In some instances, primers comprise terminator nucleotides, such as 1, 2, 3, 4, 5, 10, or more than 10 terminator nucleotides. Primers need not be limited to components which are added externally to an amplification reaction. In some instances, primers are generated in-situ through the addition of nucleotides and proteins which promote priming. For example, primase-like enzymes in combination with nucleotides is in some instances used to generate random primers for the methods described herein. Primase-like enzymes in some instances are members of the DnaG or AEP enzyme superfamily. In some instances, a primase-like enzyme is TthPrimPol. In some instances, a primase-like enzyme is T7 gp4 helicase-primase. Such primases are in some instances used with the polymerases or strand displacement factors described herein. In some instances, primases initiate priming with deoxyribonucleotides. In some instances, primases initiate priming with ribonucleotides.

The PTA amplification can be followed by selection for a specific subset of amplicons. Such selections are in some instances dependent on size, affinity, activity, hybridization to probes, or other known selection factor in the art. In some instances, selections precede or follow additional steps described herein, such as adapter ligation and/or library amplification. In some instances, selections are based on size (length) of the amplicons. In some instances, smaller amplicons are selected that are less likely to have undergone exponential amplification, which enriches for products that were derived from the primary template while further converting the amplification from an exponential into a quasi-linear amplification process (FIG. 1A). In some instances, amplicons comprising 50-2000, 25-5000, 40-3000, 50-1000, 200-1000, 300-1000, 400-1000, 400-600, 600-2000, or 800-1000 bases in length are selected. Size selection in some instances occurs with the use of protocols, e.g., utilizing solid-phase reversible immobilization (SPRI) on carboxylated paramagnetic beads to enrich for nucleic acid fragments of specific sizes, or other protocol known by those skilled in the art. Optionally or in combination, selection occurs through preferential amplification of smaller fragments during PCR while preparing sequencing libraries, as well as a result of the preferential formation of clusters from smaller sequencing library fragments during Illumina sequencing. Other strategies to select for smaller fragments are also consistent with the methods described herein and include, without limitation, isolating nucleic acid fragments of specific sizes after gel electrophoresis, the use of silica columns that bind nucleic acid fragments of specific sizes, and the use of other PCR strategies that more strongly enrich for smaller fragments.

The non-complementary portion of a primer used in PTA can include sequences which can be used to further manipulate and/or analyze amplified sequences. An example of such a sequence is a "detection tag". Detection tags have sequences complementary to detection probes and are detected using their cognate detection probes. There may be one, two, three, four, or more than four detection tags on a primer. There is no fundamental limit to the number of detection tags that can be present on a primer except the size of the primer. In some instances, there is a single detection tag on a primer. In some instances, there are two detection tags on a primer. When there are multiple detection tags, they may have the same sequence or they may have different sequences, with each different sequence complementary to a different detection probe. In some instances, multiple detection tags have the same sequence. In some instances, multiple detection tags have a different sequence.

Another example of a sequence that can be included in the non-complementary portion of a primer is an "address tag". An address tag has a sequence complementary to an address probe. Address tags become incorporated at the ends of amplified strands. If present, there may be one, or more than one, address tag on a primer. There is no fundamental limit to the number of address tags that can be present on a primer except the size of the primer. When there are multiple address tags, they may have the same sequence or they may have different sequences, with each different sequence complementary to a different address probe. The address tag portion can be any length that supports specific and stable hybridization between the address tag and the address probe. In some instances, nucleic acids from more than one source can incorporate a variable tag sequence. This tag sequence can be up to 100 nucleotides in length, preferably 1 to 10 nucleotides in length, most preferably 4, 5 or 6 nucleotides in length and comprises combinations of nucleotides. In some instances, a tag sequence is 1-20, 2-15, 3-13, 4-12, 5-12, or 1-10 nucleotides in length For example, if six base-pairs are chosen to form the tag and a permutation of four different nucleotides is used, then a total of 4096 nucleic acid anchors (e.g. hairpins), each with a unique 6 base tag can be made.

Primers described herein may be present in solution or immobilized on a solid support. In some instances, primers bearing sample barcodes and/or UMI sequences can be immobilized on a solid support. The solid support can be, for example, one or more beads. In some instances, individual cells are contacted with one or more beads having a unique set of sample barcodes and/or UMI sequences in order to identify the individual cell. In some instances, lysates from individual cells are contacted with one or more beads having a unique set of sample barcodes and/or UMI sequences in order to identify the individual cell lysates. In some instances, purified nucleic acid from individual cells are contacted with one or more beads having a unique set of sample barcodes and/or UMI sequences in order to identify the purified nucleic acid from the individual cell. The beads can be manipulated in any suitable manner as is known in the art, for example, using droplet actuators as described herein. The beads may be any suitable size, including for example, microbeads, microparticles, nanobeads and nanoparticles. In some embodiments, beads are magnetically responsive; in other embodiments beads are not significantly magnetically responsive. Non-limiting examples of suitable beads include flow cytometry microbeads, polystyrene microparticles and nanoparticles, functionalized polystyrene microparticles and nanoparticles, coated polystyrene microparticles and nanoparticles, silica microbeads, fluorescent microspheres and nanospheres, functionalized fluorescent microspheres and nanospheres, coated fluorescent microspheres and nanospheres, color dyed microparticles and nanoparticles, magnetic microparticles and nanoparticles, superparamagnetic microparticles and nanoparticles (e.g., DYNABEADS® available from Invitrogen Group, Carlsbad, Calif.), fluorescent microparticles and nanoparticles, coated magnetic microparticles and nanoparticles, ferromagnetic microparticles and nanoparticles, coated ferromagnetic microparticles and nanoparticles, and those described in U.S. Pat. Appl. Pub. No. US20050260686, US20030132538, US20050118574, 20050277197, 20060159962. Beads may be pre-coupled with an antibody, protein or antigen, DNA/RNA probe or any other molecule with an affinity for a desired target. In some embodiments, primers bearing sample barcodes and/or UMI sequences can be in solution. In certain embodiments, a plurality of droplets can be presented, wherein each droplet in the plurality bears a sample barcode which is unique to a droplet and the UMI which is unique to a molecule such that the UMI are repeated many times within a collection of droplets. In some embodiments, individual cells are contacted with a droplet having a unique set of sample barcodes and/or UMI sequences in order to identify the individual cell. In some embodiments, lysates from individual cells are contacted with a droplet having a unique set of sample barcodes and/or UMI sequences in order to identify the individual cell lysates. In some embodiments, purified nucleic acid from individual cells are contacted with a droplet having a unique set of sample barcodes and/or UMI sequences in order to identify the purified nucleic acid from the individual cell.

Figure 10A:
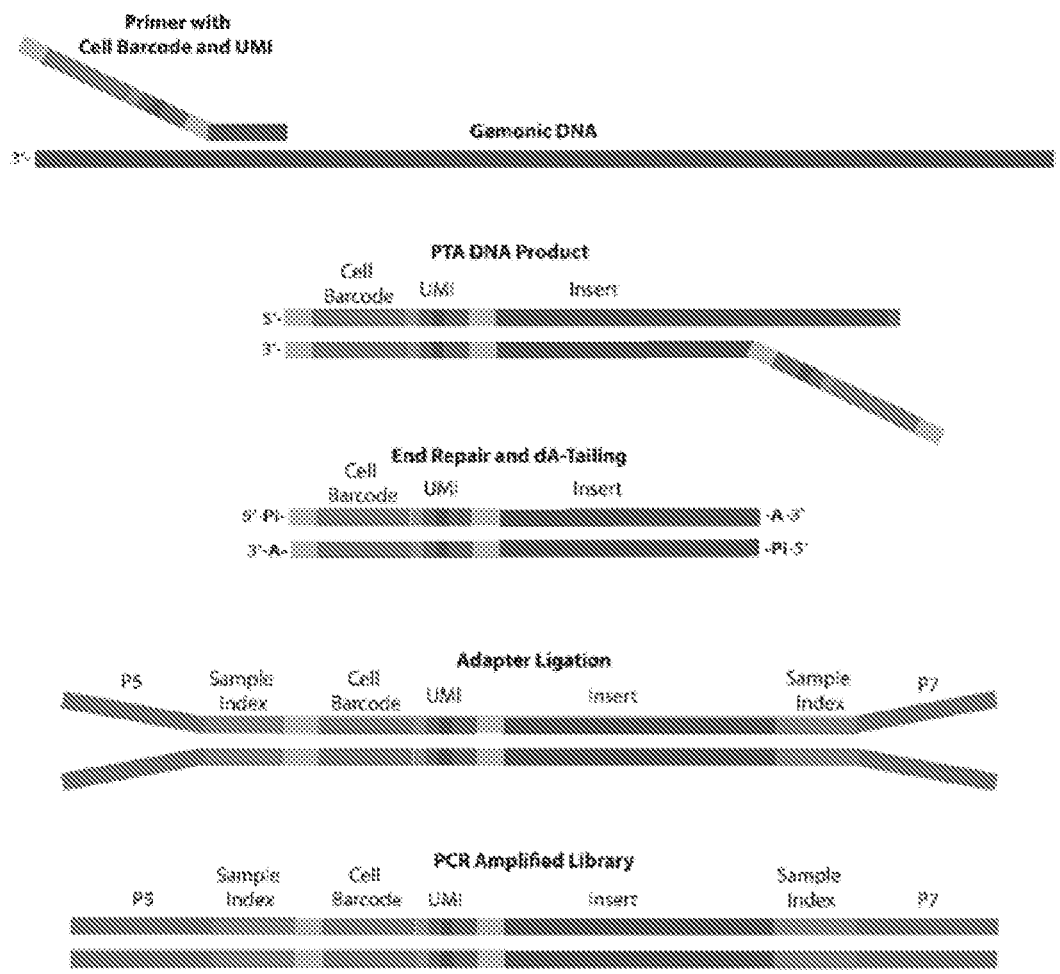
FIG. 10A demonstrates the incorporation of cellular barcodes and/or unique molecular identifiers into the PTA reactions using primers comprising cellular barcodes and/or or unique molecular identifiers.
Figure 11A:
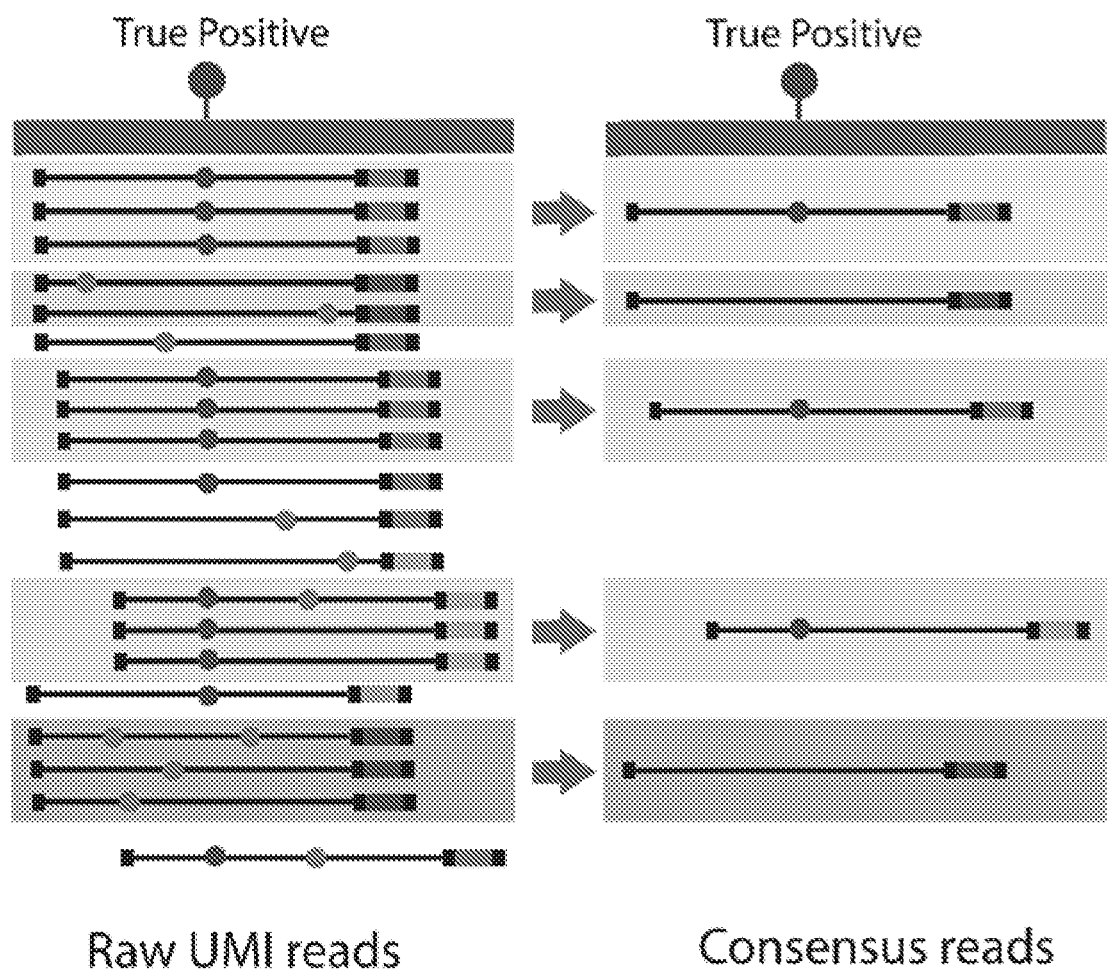
FIG. 11A (PTA_UMI) shows that the incorporation of unique molecular identifiers (UMIs) enables the creation of consensus reads, reducing the false positive rate caused by sequencing and other errors leading to increased sensitivity when performing germline or somatic variant calling.
Figure 11B:
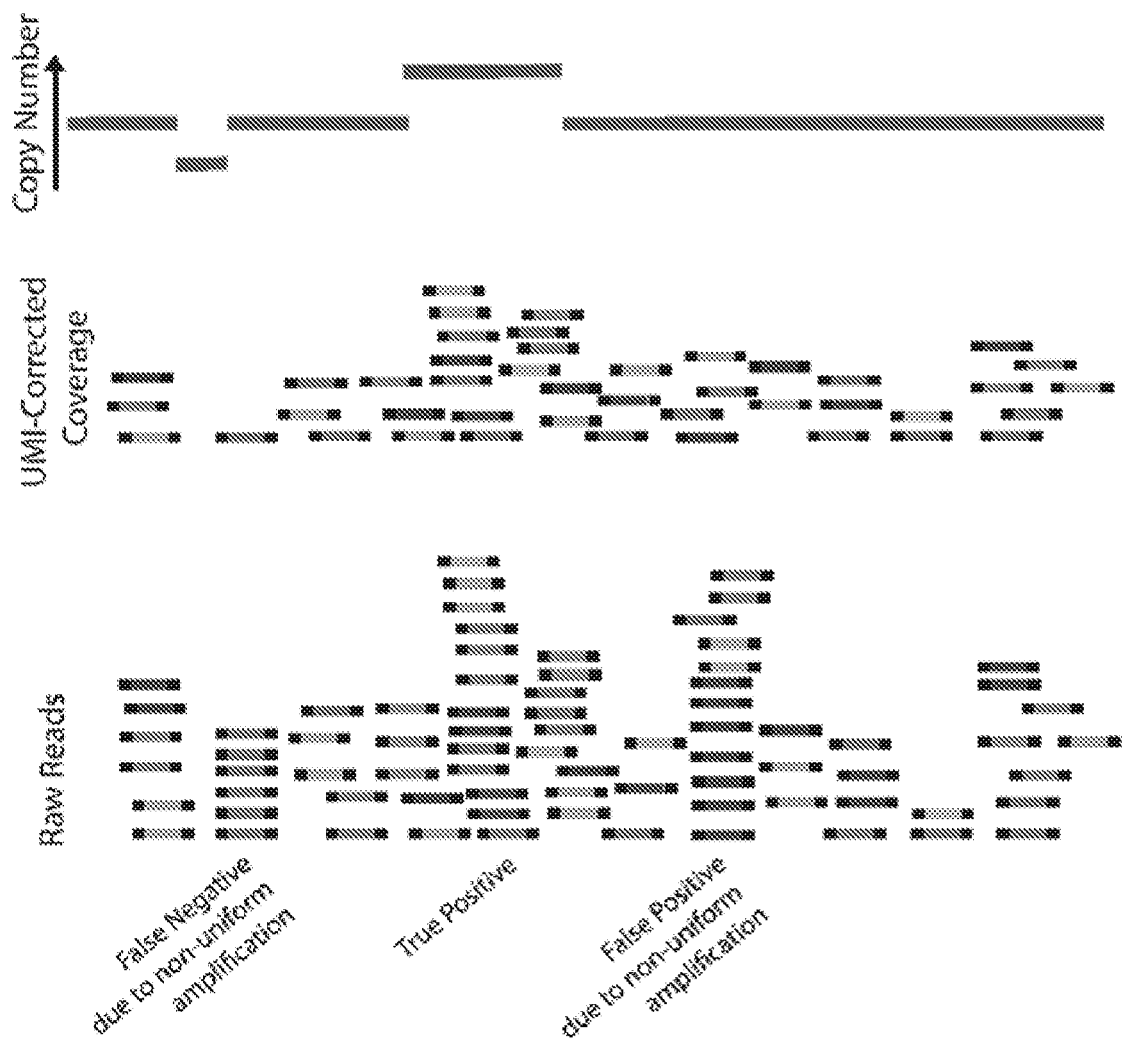
FIG. 11B shows that collapsing reads with the same UMI enables the correction of amplification and other biases that could result in the false detection or limited sensitivity when calling copy number variants.

PTA primers may comprise a sequence-specific or random primer, a cell barcode and/or a unique molecular identifier (UMI) (see, e.g., FIGS. 10A (linear primer) and 10B (hairpin primer)). In some instances, a primer comprises a sequence-specific primer. In some instances, a primer comprises a random primer. In some instances, a primer comprises a cell barcode. In some instances, a primer comprises a sample barcode. In some instances, a primer comprises a unique molecular identifier. In some instances, primers comprise two or more cell barcodes. Such barcodes in some instances identify a unique sample source, or unique workflow. Such barcodes or UMIs are in some instances 5, 6, 7, 8, 9, 10, 11, 12, 15, 20, 25, 30, or more than 30 bases in length. Primers in some instances comprise at least 1000, 10,000, 50,000, 100,000, 250,000, 500,000, $10^6$, $10^7$, $10^8$, $10^9$, or at least $10^{10}$ unique barcodes or UMIs. In some instances primers comprise at least 8, 16, 96, or 384 unique barcodes or UMIs. In some instances a standard adapter is then ligated onto the amplification products prior to sequencing; after sequencing, reads are first assigned to a specific cell based on the cell barcode. Suitable adapters that may be utilized with the PTA method include, e.g., xGen® Dual Index UMI adapters available from Integrated DNA Technologies (IDT). Reads from each cell is then grouped using the UMI, and reads with the same UMI may be collapsed into a consensus read. The use of a cell barcode allows all cells to be pooled prior to library preparation, as they can later be identified by the cell barcode. The use of the UMI to form a consensus read in some instances corrects for PCR bias, improving the copy number variation (CNV) detection (FIGS. 11A and 11B). In addition, sequencing errors may be corrected by requiring that a fixed percentage of reads from the same molecule have the same base change detected at each position. This approach has been utilized to improve CNV detection and correct sequencing errors in bulk samples. In some instances, UMIs are used with the methods described herein, for example, U.S. Pat. No. 8,835,358 discloses the principle of digital counting after attaching a random amplifiable barcode. Schmitt. et al and Fan et al. disclose similar methods of correcting sequencing errors.

The methods described herein may further comprise additional steps, including steps performed on the sample or template. Such samples or templates in some instance are subjected to one or more steps prior to PTA. In some instances, samples comprising cells are subjected to a pre-treatment step. For example, cells undergo lysis and proteolysis to increase chromatin accessibility using a combination of freeze-thawing, TRITON™ X-100 (t-Octylphenoxypolyethoxyethanol, Polyethylene glycol tert-octylphenyl ether), TWEEN® 20, (polyethylebe glycol sorbitan monolaurate, Polyoxyethylenesorbitan monolaurate), and Proteinase K. Other lysis strategies are also be suitable for practicing the methods described herein. Such strategies include, without limitation, lysis using other combinations of detergent and/or lysozyme and/or protease treatment and/or physical disruption of cells such as sonication and/or alkaline lysis and/or hypotonic lysis. In some instances, the primary template or target molecule(s) is subjected to a pre-treatment step. In some instances, the primary template (or target) is denatured using sodium hydroxide, followed by neutralization of the solution. Other denaturing strategies may also be suitable for practicing the methods described herein. Such strategies may include, without limitation, combinations of alkaline lysis with other basic solutions, increasing the temperature of the sample and/or altering the salt concentration in the sample, addition of additives such as solvents or oils, other modification, or any combination thereof. In some instances, additional steps include sorting, filtering, or isolating samples, templates, or amplicons by size. For example, after amplification with the methods described herein, amplicon libraries are enriched for amplicons having a desired length. In some instances, amplicon libraries are enriched for amplicons having a length of 50-2000, 25-1000, 50-1000, 75-2000, 100-3000, 150-500, 75-250, 170-500, 100-500, or 75-2000 bases. In some instances, amplicon libraries are enriched for amplicons having a length no more than 75, 100, 150, 200, 500, 750, 1000, 2000, 5000, or no more than 10,000 bases. In some instances, amplicon libraries are enriched for amplicons having a length of at least 25, 50, 75, 100, 150, 200, 500, 750, 1000, or at least 2000 bases.

Methods and compositions described herein may comprise buffers or other formulations. Such buffers in some instances comprise surfactants/detergent or denaturing agents (Tween-20, DMSO, DMF, pegylated polymers comprising a hydrophobic group, or other surfactant), salts (potassium or sodium phosphate (monobasic or dibasic), sodium chloride, potassium chloride, TrisHCl, magnesium chloride or suflate, Ammonium salts such as phosphate, nitrate, or sulfate, EDTA), reducing agents (DTT, THP, DTE, beta-mercaptoethanol, TCEP, or other reducing agent) or other components (glycerol, hydrophilic polymers such as PEG). In some instances, buffers are used in conjunction with components such as polymerases, strand displacement factors, terminators, or other reaction component described herein.

The nucleic acid molecules amplified according to the methods described herein may be sequenced and analyzed using methods known to those of skill in the art. Non-limiting examples of the sequencing methods which in some instances are used include, e.g., sequencing by hybridization (SBH), sequencing by ligation (SBL) (Shendure et al. (2005) Science 309:1728), quantitative incremental fluorescent nucleotide addition sequencing (QIFNAS), stepwise ligation and cleavage, fluorescence resonance energy transfer (FRET), molecular beacons, TaqMan reporter probe digestion, pyrosequencing, fluorescent in situ sequencing (FISSEQ), FISSEQ beads (U.S. Pat. No. 7,425,431), wobble sequencing (Int. Pat. Appl. Pub. No. WO2006/073504), multiplex sequencing (U.S. Pat. Appl. Pub. No. US2008/0269068; Porreca et al., 2007, Nat. Methods 4:931), polymerized colony (POLONY) sequencing (U.S. Pat. Nos. 6,432,360, 6,485,944 and 6,511,803, and Int. Pat. Appl. Pub. No. WO2005/082098), nanogrid rolling circle sequencing (ROLONY) (U.S. Pat. No. 9,624,538), allele-specific oligo ligation assays (e.g., oligo ligation assay (OLA), single template molecule OLA using a ligated linear probe and a rolling circle amplification (RCA) readout, ligated padlock probes, and/or single template molecule OLA using a ligated circular padlock probe and a rolling circle amplification (RCA) readout), high-throughput sequencing methods such as, e.g., methods using Roche 454, Illumina Solexa, AB-SOLiD, Helicos, Polonator platforms and the like, and light-based sequencing technologies (Landegren et al. (1998) Genome Res. 8:769-76; Kwok (2000) Pharmacogenomics 1:95-100; and Shi (2001) Clin. Chem. 47:164-172). In some instances, the amplified nucleic acid molecules are shotgun sequenced.

Methods and Applications

Described herein are methods of identifying mutations in cells with the methods of PTA. Use of the PTA method in some instances results in improvements over known methods, for example, MDA. PTA in some instances has lower false positive and false negative variant calling rates than the MDA method. Genomes, such as NA12878 platinum genomes, are in some instances used to determine if the greater genome coverage and uniformity of PTA would result in lower false negative variant calling rate. Without being bound by theory, it may be determined that the lack of error propagation in PTA decreases the false positive variant call rate. The amplification balance between alleles with the two methods is in some cases estimated by comparing the allele frequencies of the heterozygous mutation calls at known positive loci. In some instances, amplicon libraries generated using PTA are further amplified by PCR.

Figure 6A:
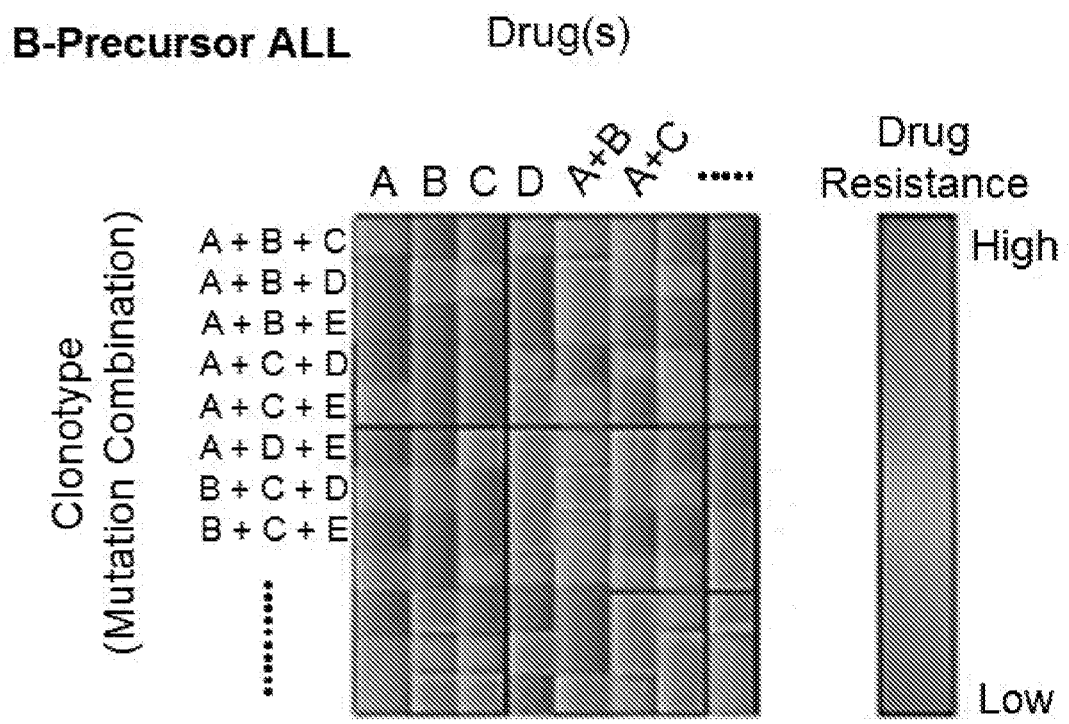
FIG. 6A depicts a schematic description of a catalog of clonotype drug sensitivity according to the disclosure. By identifying the drug sensitivities of distinct clonotypes, a catalog can be created from which oncologists can translate clonotypes identified in a patient's tumor to a list of drugs that will best target the resistant populations.

Cells analyzed using the methods described herein in some instances comprise tumor cells. For example, circulating tumor cells can be isolated from a fluid taken from patients, such as but not limited to, blood, bone marrow, urine, saliva, cerebrospinal fluid, pleural fluid, pericardial fluid, ascites, or aqueous humor. The cells are then subjected to the methods described herein (e.g. PTA) and sequencing to determine mutation burden and mutation combination in each cell. These data are in some instances used for the diagnosis of a specific disease or as tools to predict treatment response. Similarly, in some instances cells of unknown malignant potential in some instances are isolated from fluid taken from patients, such as but not limited to, blood, bone marrow, urine, saliva, cerebrospinal fluid, pleural fluid, pericardial fluid, ascites, or aqueous humor. After utilizing the methods described herein and sequencing, such methods are further used to determine mutation burden and mutation combination in each cell. These data are in some instances used for the diagnosis of a specific disease or as tools to predict progression of a premalignant state to overt malignancy. In some instances, cells can be isolated from primary tumor samples. The cells can then undergo PTA and sequencing to determine mutation burden and mutation combination in each cell. These data can be used for the diagnosis of a specific disease or are as tools to predict the probability that a patient's malignancy is resistant to available anti-cancer drugs. By exposing samples to different chemotherapy agents, it has been found that the major and minor clones have differential sensitivity to specific drugs that does not necessarily correlate with the presence of a known "driver mutation," suggesting that combinations of mutations within a clonal population determine its sensitivities to specific chemotherapy drugs. Without being bound by theory, these findings suggest that a malignancy may be easier to eradicate if premalignant lesions that have not yet expanded are and evolved into clones are detected whose increased number of genome modification may make them more likely to be resistant to treatment. See, Ma et al., 2018, "Pan-cancer genome and transcriptome analyses of 1,699 pediatric leukemias and solid tumors." A single-cell genomics protocol is in some instances used to detect the combinations of somatic genetic variants in a single cancer cell, or clonotype, within a mixture of normal and malignant cells that are isolated from patient samples. This technology is in some instances further utilized to identify clonotypes that undergo positive selection after exposure to drugs, both in vitro and/or in patients. As shown in FIG. 6A, by comparing the surviving clones exposed to chemotherapy compared to the clones identified at diagnosis, a catalog of cancer clonotypes can be created that documents their resistance to specific drugs. PTA methods in some instances detect the sensitivity of specific clones in a sample composed of multiple clonotypes to existing or novel drugs, as well as combinations thereof, where the method can detect the sensitivity of specific clones to the drug. This approach in some instances shows efficacy of a drug for a specific clone that may not be detected with current drug sensitivity measurements that consider the sensitivity of all cancer clones together in one measurement. When the PTA described herein are applied to patient samples collected at the time of diagnosis in order to detect the cancer clonotypes in a given patient's cancer, a catalog of drug sensitivities may then be used to look up those clones and thereby inform oncologists as to which drug or combination of drugs will not work and which drug or combination of drugs is most likely to be efficacious against that patient's cancer.

Described herein are methods of measuring the mutagenicity of an environmental factor. For example, cells (single or a population) are exposed to a potential environmental condition. For example, cells such originating from organs (liver, pancreas, lung, colon, thyroid, or other organ), tissues (skin, or other tissue), blood, or other biological source are in some instances used with the method. In some instances, an environmental condition comprises heat, light (e.g. ultraviolet), radiation, a chemical substance, or any combination thereof. After an amount of exposure to the environmental condition, in some instances minutes, hours, days, or longer, single cells are isolated and subjected to the PTA method. In some instances, molecular barcodes and unique molecular identifiers are used to tag the sample. The sample is sequenced and then analyzed to identify mutations resulting from exposure to the environmental condition. In some instances, such mutations are compared with a control environmental condition, such as a known non-mutagenic substance, vehicle/solvent, or lack of an environmental condition. Such analysis in some instances not only provides the total number of mutations caused by the environmental condition, but also the locations and nature of such mutations. Patterns are in some instances identified from the data, and may be used for diagnosis of diseases or conditions. In some instances, patterns are used to predict future disease states or conditions. In some instances, the methods described herein measure the mutation burden, locations, and patterns in a cell after exposure to an environmental agent, such as, e.g., a potential mutagen or teratogen. This approach in some instances is used to evaluate the safety of a given agent, including its potential to induce mutations that can contribute to the development of a disease. For example, the method could be used to predict the carcinogenicity or teratogenicity of an agent to specific cell types after exposure to a specific concentration of the specific agent.

Described herein are methods of identifying mutations in animal, plant or microbial cells that have undergone genome editing (e.g., using CRISPR technologies). Such cells in some instances can be isolated and subjected to PTA and sequencing to determine mutation burden and mutation combination in each cell. The per-cell mutation rate and locations of mutations that result from a genome editing protocol are in some instances used to assess the safety of a given genome editing method.

Described herein are methods of determining mutations in cells that are used for cellular therapy, such as but not limited to the transplantation of induced pluripotent stem cells, transplantation of hematopoietic or other cells that have not be manipulated, or transplantation of hematopoietic or other cells that have undergone genome edits. The cells can then undergo PTA and sequencing to determine mutation burden and mutation combination in each cell. The per-cell mutation rate and locations of mutations in the cellular therapy product can be used to assess the safety and potential efficacy of the product.

In a further embodiment, cells can be isolated from blastomeres that are created by in vitro fertilization. The cells can then undergo PTA and sequencing to determine the burden and combination of potentially disease predisposing genetic variants in each cell. The mutation profile of the cell can then be used to extrapolate the genetic predisposition of the blastomere to specific diseases prior to implantation.

In another embodiment, microbial cells (e.g., bacteria, fungi, protozoa) can be isolated from plants or animals (e.g., from microbiota samples [e.g., GI microbiota, skin microbiota, etc.] or from bodily fluids such as, e.g., blood, bone marrow, urine, saliva, cerebrospinal fluid, pleural fluid, pericardial fluid, ascites, or aqueous humor). In addition, microbial cells may be isolated from indwelling medical devices, such as but not limited to, intravenous catheters, urethral catheters, cerebrospinal shunts, prosthetic valves, artificial joints, or endotracheal tubes. The cells can then undergo PTA and sequencing to determine the identity of a specific microbe, as well as to detect the presence of microbial genetic variants that predict response (or resistance) to specific antimicrobial agents. These data can be used for the diagnosis of a specific infectious disease and/or as tools to predict treatment response.

Described herein are methods generating amplicon libraries from samples comprising short nucleic acid using the PTA methods described herein. In some instances, PTA leads to improved fidelity and uniformity of amplification of shorter nucleic acids. In some instances, nucleic acids are no more than 2000 bases in length. In some instances, nucleic acids are no more than 1000 bases in length. In some instances, nucleic acids are no more than 500 bases in length. In some instances, nucleic acids are no more than 200, 400, 750, 1000, 2000 or 5000 bases in length. In some instances, samples comprising short nucleic acid fragments include but at not limited to ancient DNA (hundreds, thousands, millions, or even billions of years old), FFPE (Formalin-Fixed Paraffin-Embedded) samples, cell-free DNA, or other sample comprising short nucleic acids.

Embodiments

Described herein are methods of amplifying a target nucleic acid molecule, the method comprising: a) bringing into contact a sample comprising the target nucleic acid molecule, one or more amplification primers, a nucleic acid polymerase, and a mixture of nucleotides which comprises one or more terminator nucleotides which terminate nucleic acid replication by the polymerase, and b) incubating the sample under conditions that promote replication of the target nucleic acid molecule to obtain a plurality of terminated amplification products, wherein the replication proceeds by strand displacement replication. In one embodiment of any of the above methods, the method further comprises isolating from the plurality of terminated amplification products the products which are between about 50 and about 2000 nucleotides in length. In one embodiment of any of the above methods, the method further comprises isolating from the plurality of terminated amplification products the products which are between about 400 and about 600 nucleotides in length. In one embodiment of any of the above methods, the method further comprises: c) removing the terminal terminator nucleotides from the terminated amplification products; d) repairing ends and A-tailing, and e) ligating the molecules obtained in step (d) to adaptors, and thereby generating a library of amplification products. In one embodiment of any of the above methods, the method further comprises sequencing the amplification products. In one embodiment of any of the above methods, the amplification is performed under substantially isothermic conditions. In one embodiment of any of the above methods, the nucleic acid polymerase is a DNA polymerase.

In one embodiment of any of the above methods, the DNA polymerase is a strand displacing DNA polymerase. In one embodiment of any of the above methods, the nucleic acid polymerase is selected from bacteriophage phi29 (Φ29) polymerase, genetically modified phi29 (Φ29) DNA polymerase, Klenow Fragment of DNA polymerase I, phage M2 DNA polymerase, phage phiPRD1 DNA polymerase, Bst DNA polymerase, Bst large fragment DNA polymerase, exo(-) Bst polymerase, exo(-)Bca DNA polymerase, Bsu DNA polymerase, a DNA polymerase sold under the trademark VENT®, an (exo-) DNA polymerase sold under trademark VENT®, a DNA polymerase sold under trademark DEEP VENT®, an (exo-) DNA polymerase sold under trademark DEEP VENT®, a DNA polymerase sold under trademark ISOPOL, DNA polymerase I, a DNA polymerase sold under trademark THERMINATOR™, T5 DNA polymerase, a polymerase sold under trademark SEQUENASE™, T7 DNA polymerase, T7-Sequenase, and T4 DNA polymerase. In one embodiment of any of the above methods, the nucleic acid polymerase has 3'->5' exonuclease activity and the terminator nucleotides inhibit such 3'->5' exonuclease activity. In one specific embodiment, the terminator nucleotides are selected from nucleotides with modification to the alpha group (e.g., alpha-thio dideoxynucleotides creating a phosphorothioate bond), C3 spacer nucleotides, locked nucleic acids (LNA), inverted nucleic acids, 2' fluoro nucleotides, 3' phosphorylated nucleotides, 2'-O-Methyl odified nucleotides, and trans nucleic acids. In one embodiment of any of the above methods, the nucleic acid polymerase does not have 3'->5' exonuclease activity. In one specific embodiment, the polymerase is selected from Bst DNA polymerase, exo(-) Bst polymerase, exo(-) Bca DNA polymerase, Bsu DNA polymerase, an (exo-) DNA polymerase sold under trademark VENT®, an (exo-) DNA polymerase sold under trademark DEEP VENT®, Klenow Fragment (exo-) DNA polymerase, and a DNA polymerase sold under trademark THERMINATOR. In one specific embodiment, the terminator nucleotides comprise modifications of the r group of the 3' carbon of the deoxyribose. In one specific embodiment, the terminator nucleotides are selected from 3' blocked reversible terminator comprising nucleotides, 3' unblocked reversible terminator comprising nucleotides, terminators comprising 2' modifications of deoxynucleotides, terminators comprising modifications to the nitrogenous base of deoxynucleotides, and combinations thereof. In one specific embodiment, the terminator nucleotides are selected from dideoxynucleotides, inverted dideoxynucleotides, 3' biotinylated nucleotides, 3' amino nucleotides, 3'-phosphorylated nucleotides, 3'-O-methyl nucleotides, 3' carbon spacer nucleotides including 3' C3 spacer nucleotides, 3' C18 nucleotides, 3' Hexanediol spacer nucleotides, acyclonucleotides, and combinations thereof. In one embodiment of any of the above methods, the amplification primers are between 4 and 70 nucleotides long. In one embodiment of any of the above methods, the amplification products are between about 50 and about 2000 nucleotides in length. In one embodiment of any of the above methods, the target nucleic acid is DNA (e.g., a cDNA or a genomic DNA). In one embodiment of any of the above methods, the amplification primers are random primers. In one embodiment of any of the above methods, the amplification primers comprise a barcode. In one specific embodiment, the barcode comprises a cell barcode. In one specific embodiment, the barcode comprises a sample barcode. In one embodiment of any of the above methods, the amplification primers comprise a unique molecular identifier (UMI). In one embodiment of any of the above methods, the method comprises denaturing the target nucleic acid or genomic DNA before the initial primer annealing. In one specific embodiment, denaturation is conducted under alkaline conditions followed by neutralization. In one embodiment of any of the above methods, the sample, the amplification primers, the nucleic acid polymerase, and the mixture of nucleotides are contained in a microfluidic device. In one embodiment of any of the above methods, the sample, the amplification primers, the nucleic acid polymerase, and the mixture of nucleotides are contained in a droplet. In one embodiment of any of the above methods, the sample is selected from tissue(s) samples, cells, biological fluid samples (e.g., blood, urine, saliva, lymphatic fluid, cerebrospinal fluid (CSF), amniotic fluid, pleural fluid, pericardial fluid, ascites, aqueous humor), bone marrow samples, semen samples, biopsy samples, cancer samples, tumor samples, cell lysate samples, forensic samples, archaeological samples, paleontological samples, infection samples, production samples, whole plants, plant parts, microbiota samples, viral preparations, soil samples, marine samples, freshwater samples, household or industrial samples, and combinations and isolates thereof. In one embodiment of any of the above methods, the sample is a cell (e.g., an animal cell [e.g., a human cell], a plant cell, a fungal cell, a bacterial cell, and a protozoal cell). In one specific embodiment, the cell is lysed prior to the replication. In one specific embodiment, cell lysis is accompanied by proteolysis. In one specific embodiment, the cell is selected from a cell from a preimplantation embryo, a stem cell, a fetal cell, a tumor cell, a suspected cancer cell, a cancer cell, a cell subjected to a gene editing procedure, a cell from a pathogenic organism, a cell obtained from a forensic sample, a cell obtained from an archeological sample, and a cell obtained from a paleontological sample. In one embodiment of any of the above methods, the sample is a cell from a preimplantation embryo (e.g., a blastomere [e.g., a blastomere obtained from an eight-cell stage embryo produced by in vitro fertilization]). In one specific embodiment, the method further comprises determining the presence of disease predisposing germline or somatic variants in the embryo cell. In one embodiment of any of the above methods, the sample is a cell from a pathogenic organism (e.g., a bacterium, a fungus, a protozoan). In one specific embodiment, the pathogenic organism cell is obtained from fluid taken from a patient, microbiota sample (e.g., GI microbiota sample, vaginal microbiota sample, skin microbiota sample, etc.) or an indwelling medical device (e.g., an intravenous catheter, a urethral catheter, a cerebrospinal shunt, a prosthetic valve, an artificial joint, an endotracheal tube, etc.). In one specific embodiment, the method further comprises the step of determining the identity of the pathogenic organism. In one specific embodiment, the method further comprises determining the presence of genetic variants responsible for resistance of the pathogenic organism to a treatment. In one embodiment of any of the above methods, the sample is a tumor cell, a suspected cancer cell, or a cancer cell. In one specific embodiment, the method further comprises determining the presence of one or more diagnostic or prognostic mutations. In one specific embodiment, the method further comprises determining the presence of germline or somatic variants responsible for resistance to a treatment. In one embodiment of any of the above methods, the sample is a cell subjected to a gene editing procedure. In one specific embodiment, the method further comprises determining the presence of unplanned mutations caused by the gene editing process. In one embodiment of any of the above methods, the method further comprises determining the history of a cell lineage. In a related aspect, the invention provides a use of any of the above methods for identifying low frequency sequence variants (e.g., variants which constitute ≥0.01% of the total sequences).

In a related aspect, the invention provides a kit comprising a nucleic acid polymerase, one or more amplification primers, a mixture of nucleotides comprising one or more terminator nucleotides, and optionally instructions for use. In one embodiment of the kits of the invention, the nucleic acid polymerase is a strand displacing DNA polymerase. In one embodiment of the kits of the invention, the nucleic acid polymerase is selected from bacteriophage phi29 (Φ29) polymerase, genetically modified phi29 (129) DNA polymerase, Klenow Fragment of DNA polymerase I, phage M2 DNA polymerase, phage phiPRD1 DNA polymerase, Bst DNA polymerase, Bst large fragment DNA polymerase, exo(-) Bst polymerase, exo(-)Bca DNA polymerase, Bsu DNA polymerase, a DNA polymerase sold under the trademark VENT®, an (exo-) DNA polymerase sold under trademark VENT®, a DNA polymerase sold under trademark DEEP VENT®, an (exo-) DNA polymerase sold under trademark DEEP VENT®, a DNA polymerase sold under trademark ISOPOL™, DNA polymerase I, a DNA polymerase sold under trademark THERMINATOR™, T5 DNA polymerase, a polymerase sold under trademark SEQUENASE™, T7 DNA polymerase, T7-Sequenase, and T4 DNA polymerase. In one embodiment of the kits of the invention, the nucleic acid polymerase has 3'->5' exonuclease activity and the terminator nucleotides inhibit such 3'->5' exonuclease activity (e.g., nucleotides with modification to the alpha group [e.g., alpha-thio dideoxynucleotides], C3 spacer nucleotides, locked nucleic acids (LNA), inverted nucleic acids, 2' fluoro nucleotides, 3' phosphorylated nucleotides, 2'-O-Methyl modified nucleotides, trans nucleic acids). In one embodiment of the kits of the invention, the nucleic acid polymerase does not have 3'->5' exonuclease activity (e.g., Bst DNA polymerase, exo(-) Bst polymerase, exo(-) Bca DNA polymerase, Bsu DNA polymerase, VentR (exo-) DNA polymerase, Deep Vent (exo-) DNA polymerase, Klenow Fragment (exo-) DNA polymerase, a DNA polymerase sold under trademark THERMINATOR). In one specific embodiment, the terminator nucleotides comprise modifications of the r group of the 3' carbon of the deoxyribose. In one specific embodiment, the terminator nucleotides are selected from 3' blocked reversible terminator comprising nucleotides, 3' unblocked reversible terminator comprising nucleotides, terminators comprising 2' modifications of deoxynucleotides, terminators comprising modifications to the nitrogenous base of deoxynucleotides, and combinations thereof. In one specific embodiment, the terminator nucleotides are selected from dideoxynucleotides, inverted dideoxynucleotides, 3' biotinylated nucleotides, 3' amino nucleotides, 3'-phosphorylated nucleotides, 3'-O-methyl nucleotides, 3' carbon spacer nucleotides including 3' C3 spacer nucleotides, 3' C18 nucleotides, 3' Hexanediol spacer nucleotides, acyclonucleotides, and combinations thereof.

Described herein are methods of amplifying a genome, the method comprising: a) bringing into contact a sample comprising the genome, a plurality of amplification primers (e.g., two or more primers), a nucleic acid polymerase, and a mixture of nucleotides which comprises one or more terminator nucleotides which terminate nucleic acid replication by the polymerase, and b) incubating the sample under conditions that promote replication of the genome to obtain a plurality of terminated amplification products, wherein the replication proceeds by strand displacement replication. In one embodiment of any of the above methods, the method further comprises isolating from the plurality of terminated amplification products the products which are between about 50 and about 2000 nucleotides in length. In one embodiment of any of the above methods, the method further comprises isolating from the plurality of terminated amplification products the products which are between about 400 and about 600 nucleotides in length. In one embodiment of any of the above methods, the method further comprises: c) removing the terminal terminator nucleotides from the terminated amplification products; d) repairing ends and A-tailing, and e) ligating the molecules obtained in step (d) to adaptors, and thereby generating a library of amplification products. In one embodiment of any of the above methods, the method further comprises sequencing the amplification products. In one embodiment of any of the above methods, the amplification is performed under substantially isothermic conditions. In one embodiment of any of the above methods, the nucleic acid polymerase is a DNA polymerase.

In one embodiment of any of the above methods, the DNA polymerase is a strand displacing DNA polymerase. In one embodiment of any of the above methods, the nucleic acid polymerase is selected from bacteriophage phi29 (Φ29) polymerase, genetically modified phi29 (Φ29) DNA polymerase, Klenow Fragment of DNA polymerase I, phage M2 DNA polymerase, phage phiPRD1 DNA polymerase, Bst DNA polymerase, Bst large fragment DNA polymerase, exo(-) Bst polymerase, exo(-)Bca DNA polymerase, Bsu DNA polymerase, a DNA polymerase sold under the trademark VENT®, an (exo-) DNA polymerase sold under trademark VENT®, a DNA polymerase sold under trademark DEEP VENT®, an (exo-) DNA polymerase sold under trademark DEEP VENT®, a DNA polymerase sold under trademark ISOPOL, DNA polymerase I, a DNA polymerase sold under trademark THERMINATOR, T5 DNA polymerase, a polymerase sold under trademark SEQUENASE™, T7 DNA polymerase, a T7 polymerase sold under trademark SEQUENASE™, and T4 DNA polymerase. In one embodiment of any of the above methods, the nucleic acid polymerase has 3'->5' exonuclease activity and the terminator nucleotides inhibit such 3'->5' exonuclease activity. In one specific embodiment, the terminator nucleotides are selected from nucleotides with modification to the alpha group (e.g., alpha-thio dideoxynucleotides creating a phosphorothioate bond), C3 spacer nucleotides, locked nucleic acids (LNA), inverted nucleic acids, 2' fluoro nucleotides, 3' phosphorylated nucleotides, 2'-O-Methyl modified nucleotides, and trans nucleic acids. In one embodiment of any of the above methods, the nucleic acid polymerase does not have 3'->5' exonuclease activity. In one specific embodiment, the polymerase is selected from Bst DNA polymerase, exo(-) Bst polymerase, exo(-) Bca DNA polymerase, Bsu DNA polymerase, an (exo-) DNA polymerase VENT®, an (exo-) DNA polymerase sold under trademark DEEP VENT®, Klenow Fragment (exo-) DNA polymerase, and a DNA polymerase sold under trademark THERMINATOR. In one specific embodiment, the terminator nucleotides comprise modifications of the r group of the 3' carbon of the deoxyribose. In one specific embodiment, the terminator nucleotides are selected from 3' blocked reversible terminator comprising nucleotides, 3' unblocked reversible terminator comprising nucleotides, terminators comprising 2' modifications of deoxynucleotides, terminators comprising modifications to the nitrogenous base of deoxynucleotides, and combinations thereof. In one specific embodiment, the terminator nucleotides are selected from dideoxynucleotides, inverted dideoxynucleotides, 3' biotinylated nucleotides, 3' amino nucleotides, 3'-phosphorylated nucleotides, 3'-O-methyl nucleotides, 3' carbon spacer nucleotides including 3' C3 spacer nucleotides, 3' C18 nucleotides, 3' Hexanediol spacer nucleotides, acyclonucleotides, and combinations thereof. In one embodiment of any of the above methods, the amplification primers are between 4 and 70 nucleotides long. In one embodiment of any of the above methods, the amplification products are between about 50 and about 2000 nucleotides in length. In one embodiment of any of the above methods, the target nucleic acid is DNA (e.g., a cDNA or a genomic DNA). In one embodiment of any of the above methods, the amplification primers are random primers. In one embodiment of any of the above methods, the amplification primers comprise a barcode. In one specific embodiment, the barcode comprises a cell barcode. In one specific embodiment, the barcode comprises a sample barcode. In one embodiment of any of the above methods, the amplification primers comprise a unique molecular identifier (UMI). In one embodiment of any of the above methods, the method comprises denaturing the target nucleic acid or genomic DNA before the initial primer annealing. In one specific embodiment, denaturation is conducted under alkaline conditions followed by neutralization. In one embodiment of any of the above methods, the sample, the amplification primers, the nucleic acid polymerase, and the mixture of nucleotides are contained in a microfluidic device. In one embodiment of any of the above methods, the sample, the amplification primers, the nucleic acid polymerase, and the mixture of nucleotides are contained in a droplet. In one embodiment of any of the above methods, the sample is selected from tissue(s) samples, cells, biological fluid samples (e.g., blood, urine, saliva, lymphatic fluid, cerebrospinal fluid (CSF), amniotic fluid, pleural fluid, pericardial fluid, ascites, aqueous humor), bone marrow samples, semen samples, biopsy samples, cancer samples, tumor samples, cell lysate samples, forensic samples, archaeological samples, paleontological samples, infection samples, production samples, whole plants, plant parts, microbiota samples, viral preparations, soil samples, marine samples, freshwater samples, household or industrial samples, and combinations and isolates thereof. In one embodiment of any of the above methods, the sample is a cell (e.g., an animal cell [e.g., a human cell], a plant cell, a fungal cell, a bacterial cell, and a protozoal cell). In one specific embodiment, the cell is lysed prior to the replication. In one specific embodiment, cell lysis is accompanied by proteolysis. In one specific embodiment, the cell is selected from a cell from a preimplantation embryo, a stem cell, a fetal cell, a tumor cell, a suspected cancer cell, a cancer cell, a cell subjected to a gene editing procedure, a cell from a pathogenic organism, a cell obtained from a forensic sample, a cell obtained from an archeological sample, and a cell obtained from a paleontological sample. In one embodiment of any of the above methods, the sample is a cell from a preimplantation embryo (e.g., a blastomere [e.g., a blastomere obtained from an eight-cell stage embryo produced by in vitro fertilization]). In one specific embodiment, the method further comprises determining the presence of disease predisposing germline or somatic variants in the embryo cell. In one embodiment of any of the above methods, the sample is a cell from a pathogenic organism (e.g., a bacterium, a fungus, a protozoan). In one specific embodiment, the pathogenic organism cell is obtained from fluid taken from a patient, microbiota sample (e.g., GI microbiota sample, vaginal microbiota sample, skin microbiota sample, etc.) or an indwelling medical device (e.g., an intravenous catheter, a urethral catheter, a cerebrospinal shunt, a prosthetic valve, an artificial joint, an endotracheal tube, etc.). In one specific embodiment, the method further comprises the step of determining the identity of the pathogenic organism. In one specific embodiment, the method further comprises determining the presence of genetic variants responsible for resistance of the pathogenic organism to a treatment. In one embodiment of any of the above methods, the sample is a tumor cell, a suspected cancer cell, or a cancer cell. In one specific embodiment, the method further comprises determining the presence of one or more diagnostic or prognostic mutations. In one specific embodiment, the method further comprises determining the presence of germline or somatic variants responsible for resistance to a treatment. In one embodiment of any of the above methods, the sample is a cell subjected to a gene editing procedure. In one specific embodiment, the method further comprises determining the presence of unplanned mutations caused by the gene editing process. In one embodiment of any of the above methods, the method further comprises determining the history of a cell lineage. In a related aspect, the invention provides a use of any of the above methods for identifying low frequency sequence variants (e.g., variants which constitute >0.01% of the total sequences).

In a related aspect, the invention provides a kit comprising a nucleic acid polymerase, one or more amplification primers, a mixture of nucleotides comprising one or more terminator nucleotides, and optionally instructions for use. In one embodiment of the kits of the invention, the nucleic acid polymerase is a strand displacing DNA polymerase. In one embodiment of the kits of the invention, the nucleic acid polymerase is selected from bacteriophage phi29 (Φ29) polymerase, genetically modified phi29 (Φ29) DNA polymerase, Klenow Fragment of DNA polymerase I, phage M2 DNA polymerase, phage phiPRD1 DNA polymerase, Bst DNA polymerase, Bst large fragment DNA polymerase, exo(-) Bst polymerase, exo(-)Bca DNA polymerase, Bsu DNA polymerase, an (exo-) DNA polymerase sold under trademark VENT®, an (exo-) DNA polymerase sold under trademark VENT®, a DNA polymerase sold under trademark DEEP VENT™, an (exo-) DNA polymerase sold under trademark DEEP VENT™, a DNA polymerase sold under trademark ISOPOL™, DNA polymerase I, a DNA polymerase sold under trademark THERMINATOR™, T5 DNA polymerase, a polymerase sold under trademark SEQUENASE™, T7 DNA polymerase, a T7 polymerase sold under trademark SEQUENASE™, and T4 DNA polymerase. In one embodiment of the kits of the invention, the nucleic acid polymerase has 3'->5' exonuclease activity and the terminator nucleotides inhibit such 3'->5' exonuclease activity (e.g., nucleotides with modification to the alpha group [e.g., alpha-thio dideoxynucleotides], C3 spacer nucleotides, locked nucleic acids (LNA), inverted nucleic acids, 2' fluoro nucleotides, 3' phosphorylated nucleotides, 2'-O-Methyl modified nucleotides, trans nucleic acids). In one embodiment of the kits of the invention, the nucleic acid polymerase does not have 3'->5' exonuclease activity (e.g., Bst DNA polymerase, exo(-) Bst polymerase, exo(-) Bca DNA polymerase, Bsu DNA polymerase, an (exo-) DNA polymerase sold under trademark VENT®, an (exo-) DNA polymerase sold under trademark DEEP VENT®, Klenow Fragment (exo-) DNA polymerase, a DNA polymerase sold under trademark THERMINATOR™). In one specific embodiment, the terminator nucleotides comprise modifications of the r group of the 3' carbon of the deoxyribose. In one specific embodiment, the terminator nucleotides are selected from 3' blocked reversible terminator comprising nucleotides, 3' unblocked reversible terminator comprising nucleotides, terminators comprising 2' modifications of deoxynucleotides, terminators comprising modifications to the nitrogenous base of deoxynucleotides, and combinations thereof. In one specific embodiment, the terminator nucleotides are selected from dideoxynucleotides, inverted dideoxynucleotides, 3' biotinylated nucleotides, 3' amino nucleotides, 3'-phosphorylated nucleotides, 3'-O-methyl nucleotides, 3' carbon spacer nucleotides including 3' C3 spacer nucleotides, 3' C18 nucleotides, 3' Hexanediol spacer nucleotides, acyclonucleotides, and combinations thereof.

EXAMPLES

The following examples are set forth to illustrate more clearly the principle and practice of embodiments disclosed herein to those skilled in the art and are not to be construed as limiting the scope of any claimed embodiments. Unless otherwise stated, all parts and percentages are on a weight basis.

Example 1: Primary Template-Directed Amplification (PTA)

Figure 1C:
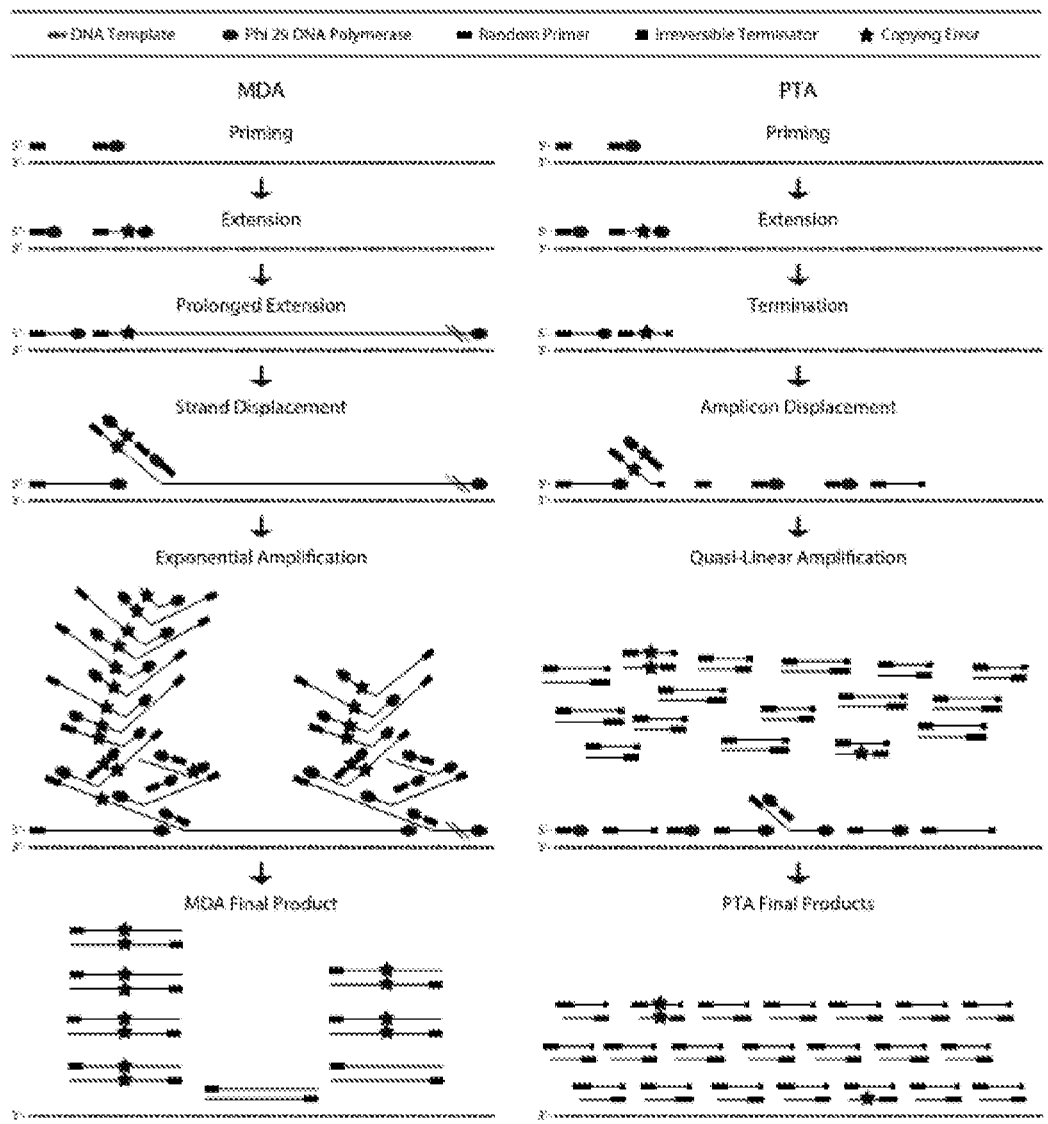
FIG. 1C illustrates a comparison of MDA and the PTA-Irreversible Terminator method as they relate to mutation propagation.
Figure 1D:
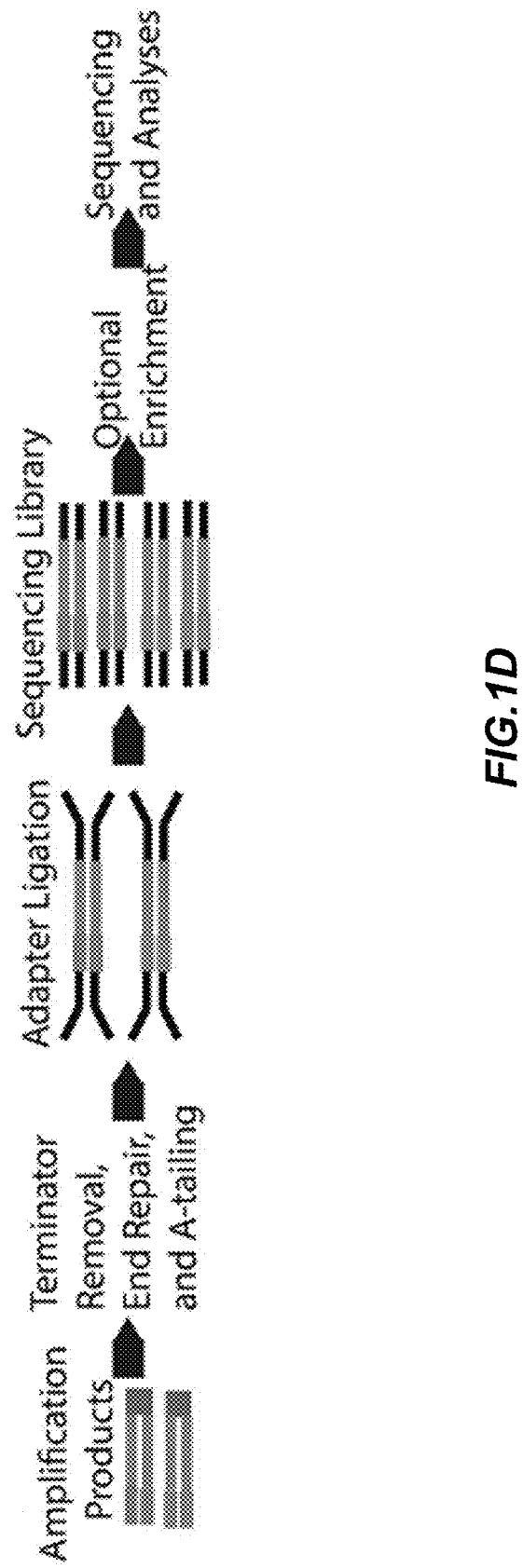
FIG. 1D illustrates the method steps performed after amplification, which include removing the terminator, repairing ends, and performing A-tailing prior to adapter ligation. The library of pooled cells can then undergo hybridization-mediated enrichment for all exons or other specific regions of interest prior to sequencing. The cell of origin of each read is identified by the cell barcode (shown as green and blue sequences).

While PTA can be used for any nucleic acid amplification, it is particularly useful for whole genome amplification as it allows to capture a larger percentage of a cell genome in a more uniform and reproducible manner and with lower error rates than the currently used methods such as, e.g., Multiple Displacement Amplification (MDA), avoiding such drawbacks of the currently used methods as exponential amplification at locations where the polymerase first extends the random primers which results in random overrepresentation of loci and alleles and mutation propagation (see FIGS. 1A-1C).

Cell Culture

Human NA12878 (Coriell Institute) cells were maintained in RPMI media, supplemented with 15% FBS and 2 mM L-glutamine, and 100 units/mL of penicillin, 100 µg/mL of streptomycin, and 0.25 µg/mL of Amphotericin B (Gibco, Life Technologies). The cells were seeded at a density of $3.5 \times 10^5$ cells/ml. The cultures were split every 3 days and were maintained in a humidified incubator at 37 C with 5% $Co_2$.

Single-Cell Isolation and WGA

After culturing NA12878 cells for a minimum of three days after seeding at a density of $3.5 \times 10^5$ cells/ml, 3 mL of cell suspension were pelleted at 300×g for 10 minutes. The medium was then discarded and the cells were washed three times with 1 mL of cell wash buffer (1×PBS containing 2% FBS without $Mg^2$ or $Ca^2$) being spun at 300×g, 200×g and finally 100×g for 5 minutes. The cells were then resuspended in 500 µL of cell wash buffer. This was followed by staining with 100 nM of Calcein AM (Molecular Probes) and 100 ng/ml of propidium iodide (PI; Sigma-Aldrich) to distinguish the live cell population. The cells were loaded on a BD FACScan flow cytometer (FACSAria II) (BD Biosciences) that had been thoroughly cleaned with ELIMINase (Decon Labs) and calibrated using Accudrop fluorescent beads (BD Biosciences) for cell sorting. A single cell from the Calcein AM-positive, PI-negative fraction was sorted in each well of a 96 well plate containing 3 µL of PBS (Qiagen, REPLI-g SC Kit) with 0.2% Tween 20 in the cells that would undergo PTA (Sigma-Aldrich). Multiple wells were intentionally left empty to be used as no template controls (NTC). Immediately after sorting, the plates were briefly centrifuged and placed on ice. Cells were then frozen at a minimum of overnight at −20° C. On a subsequent day, WGA Reactions were assembled on a pre-PCR workstation that provides a constant positive pressure of HEPA filtered air and which was decontaminated with UV light for 30 minutes before each experiment.

MDA was carried using the REPLI-g Single Cell Kit (Qiagen) with modifications that have previously been shown to improve the amplification uniformity. Specifically, exonuclease-resistant random primers (ThermoFisher) were added to Buffer D2 (REPLI-g Single Cell Kit, Qiagen) to a final concentration of 125 µM in Buffer D2. 4 µL of the resulting lysis/denaturing mix was added to the tubes containing the single cells, vortexed, briefly spun and incubated on ice for 10 minutes. The cell lysates were neutralized by adding 3 µL of Stop Solution (REPLI-g Single Cell Kit, Qiagen), mixed by vortexing, centrifuged briefly, and placed at room temperature. This was followed by addition of 40 µl of amplification mix before incubation at 30° C. for 8 hours after which the amplification was terminated by heating to 65° C. for 3 minutes.

PTA was carried out by first further lysing the cells after freeze thawing by adding 2 µl a prechilled solution of a 1:1 mixture of 5% Triton X-100 (Sigma-Aldrich) and 20 mg/ml Proteinase K (Promega). The cells were then vortexed and briefly centrifuged before placing at 40 degrees for 10 minutes. 4 µl of Buffer D2 (REPLI-g Single Cell Kit, Qiagen) and 1 µl of 500 µM exonuclease-resistant random primer were then added to the lysed cells to denature the DNA prior to vortexing, spinning, and placing at 65 degrees for 15 minutes. 4 µl of room temperature Stop solution (REPLI-g Single Cell Kit, Qiagen) was then added and the samples were vortexed and spun down. 56 µl of amplification mix (REPLI-g Single Cell Kit, Qiagen) that contained alpha-thio-ddNTPs at equal ratios at a concentration of 1200 µM in the final amplification reaction. The samples were then placed at 30° C. for 8 hours after which the amplification was terminated by heating to 65° C. for 3 minutes.

After the amplification step, the DNA from both MDA and PTA reactions were purified using AMPure XP magnetic beads (Beckman Coulter) at a 2:1 ratio of beads to sample and the yield was measured using the Qubit dsDNA HS Assay Kit with a Qubit 3.0 fluorometer according to the manufacturer's instructions (Life Technologies).

Library Preparation

The MDA reactions resulted in the production of 40 µg of amplified DNA. 1 µg of product was fragmented for 30 minutes according to the KAPA HyperPlus protocol after the addition of the conditioning solution (KAPA Biosystems). The samples then underwent standard library preparation with 15 µM of dual index adapters (Integrated DNA Technologies) and 4 cycles of PCR. Each PTA reaction generated between 40-60 ng of material which was used for DNA sequencing library preparation in its entirety using the KAPA HyperPlus kit without fragmentation. 2.5 µM adapters with UMIs and dual indices (Integrated DNA Technologies) were used in the ligation, and 15 cycles of PCR were used in the final amplification. The libraries were then cleaned up using a double sided SPRI using ratios of 0.65× and 0.55× for the right and left sided selection, respectively. The final libraries were quantified using the Qubit dsDNA BR Assay Kit and 2100 Bioanalyzer (Agilent Technologies) before sequencing on the Illumina NextSeq platform. All Illumina sequencing platforms, including the NovaSeq, are also compatible with the protocol.

Data Analysis

Sequencing reads were demultiplexed based on cell barcode using Bcl2fastq. The reads were then trimmed using trimmomatic, which was followed by alignment to hg19 using BWA. Reads underwent duplicate marking by Picard, followed by local realignment and base recalibration using GATK 4.0. All files used to calculate quality metrics were downsampled to twenty million reads using Picard DownSampleSam. Quality metrics were acquired from the final bam file using qualimap, as well as Picard AlignmentSummaryMetrics and CollectWgsMetrics. Total genome coverage was also estimated using Preseq.

Variant Calling

Single nucleotide variants and Indels were called using the GATK UnifiedGenotyper from GATK 4.0. Standard filtering criteria using the GATK best practices were used for all steps in the process (software.broadinstitute.org/gatk/best-practices/). Copy number variants were called using Control-FREEC (Boeva et al., Bioinformatics, 2012, 28(3): 423-5). Structural variants were also detected using CREST (Wang et al., Nat Methods, 2011, 8(8):652-4).

Results

Figure 2A:
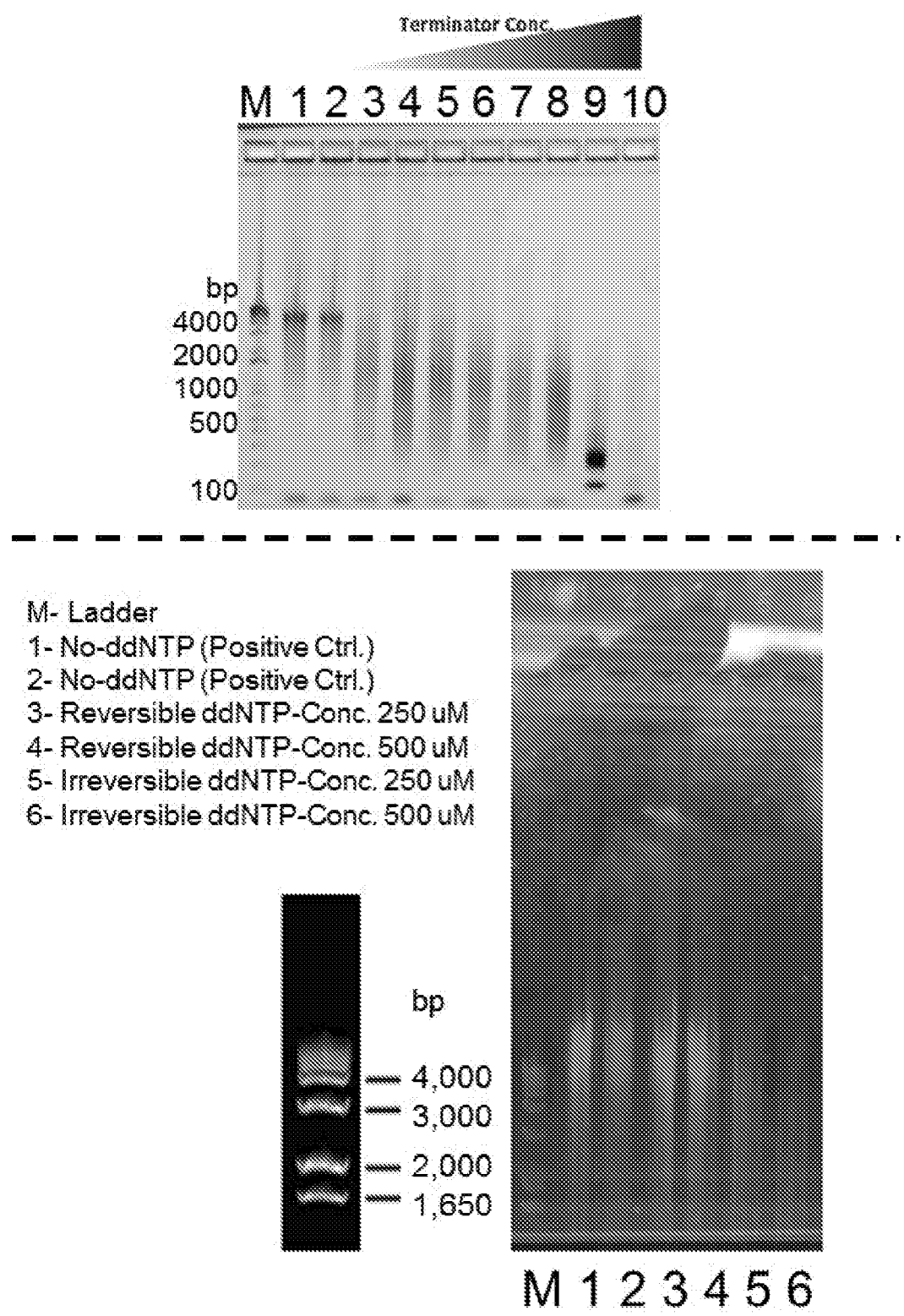
FIG. 2A shows the size distribution of amplicons after undergoing PTA with addition of increasing concentrations of terminators (top gel). The bottom gel shows size distribution of amplicons after undergoing PTA with addition of increasing concentrations of reversible terminator, or addition of increasing concentrations of irreversible terminator.
Figure 2B:
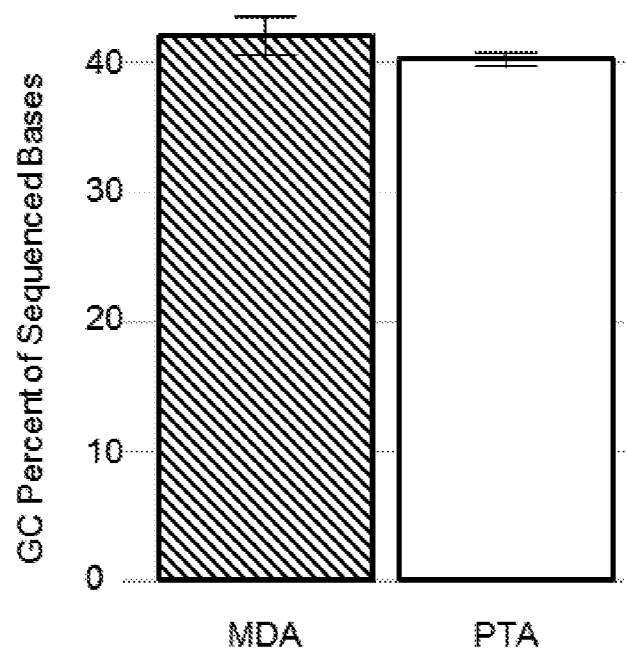
FIG. 2B (GC) shows comparison of GC content of sequenced bases for MDA and PTA.
Figure 2C:
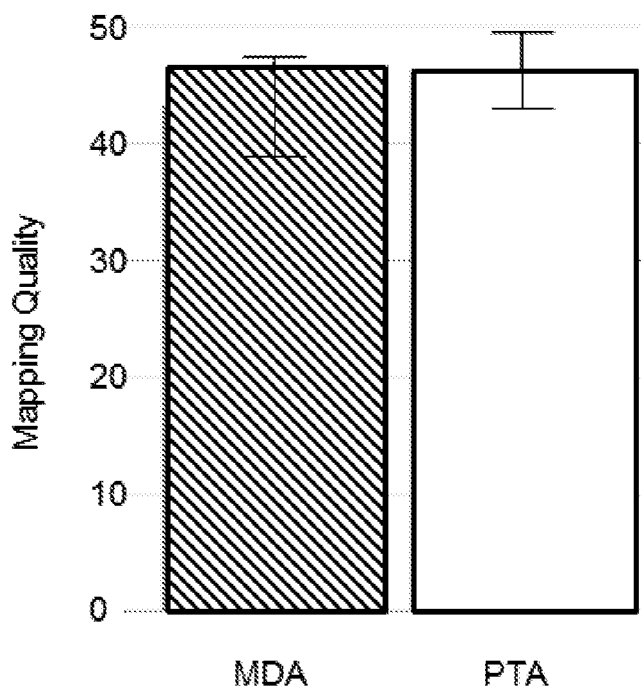
FIG. 2C shows map quality scores(e) (mapQ) mapping to human genome (p_mapped) after single cells underwent PTA or MDA.
Figure 2D:
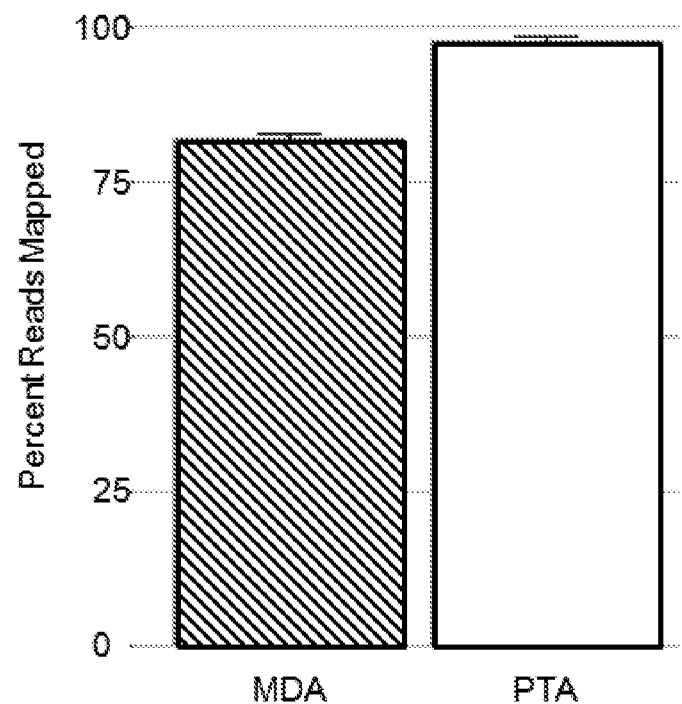
FIG. 2D percent of reads mapping to human genome (p_mapped) after single cells underwent PTA or MDA.
Figure 2E:
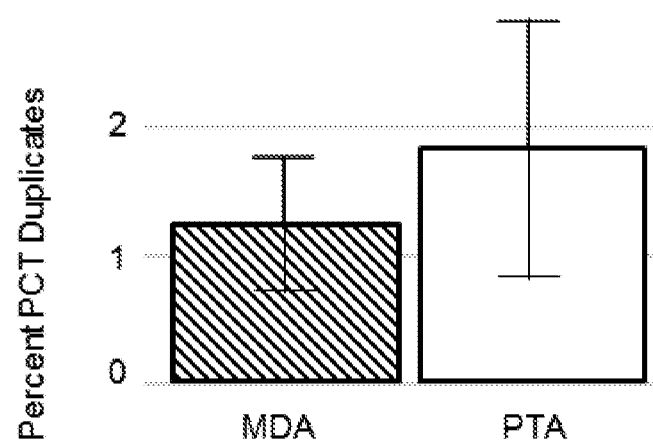
FIG. 2E (PCR) shows the comparison of percent of reads that are PCR duplicates for 20 million subsampled reads after single cells underwent MDA and PTA.
Figure 3A:
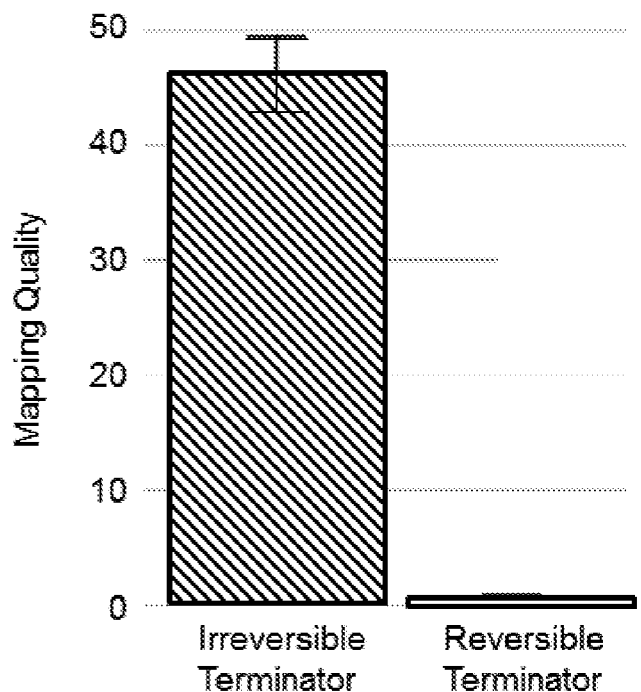
FIG. 3A shows map quality scores(c) (mapQ2) mapping to human genome (p_mapped2) after single cells underwent PTA with reversible or irreversible terminators.
Figure 3B:
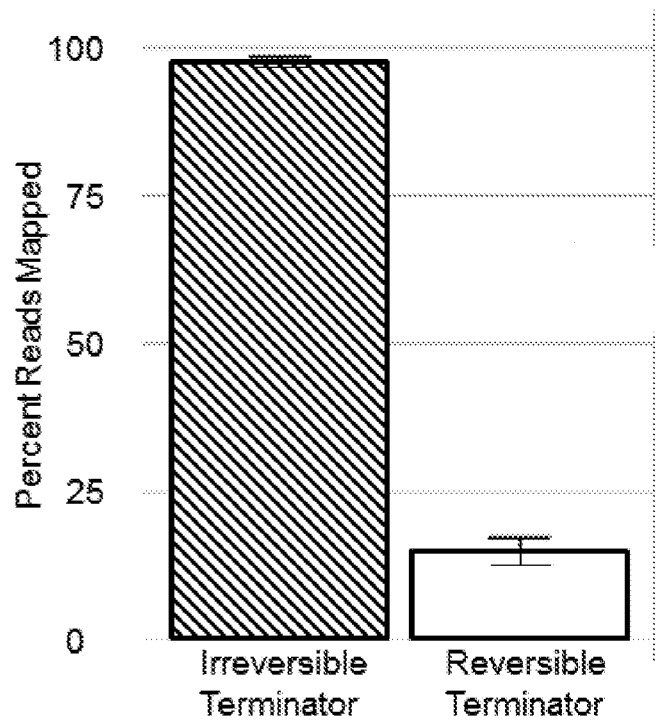
FIG. 3B shows percent of reads mapping to human genome (p_mapped2) after single cells underwent PTA with reversible or irreversible terminators.
Figure 3C:
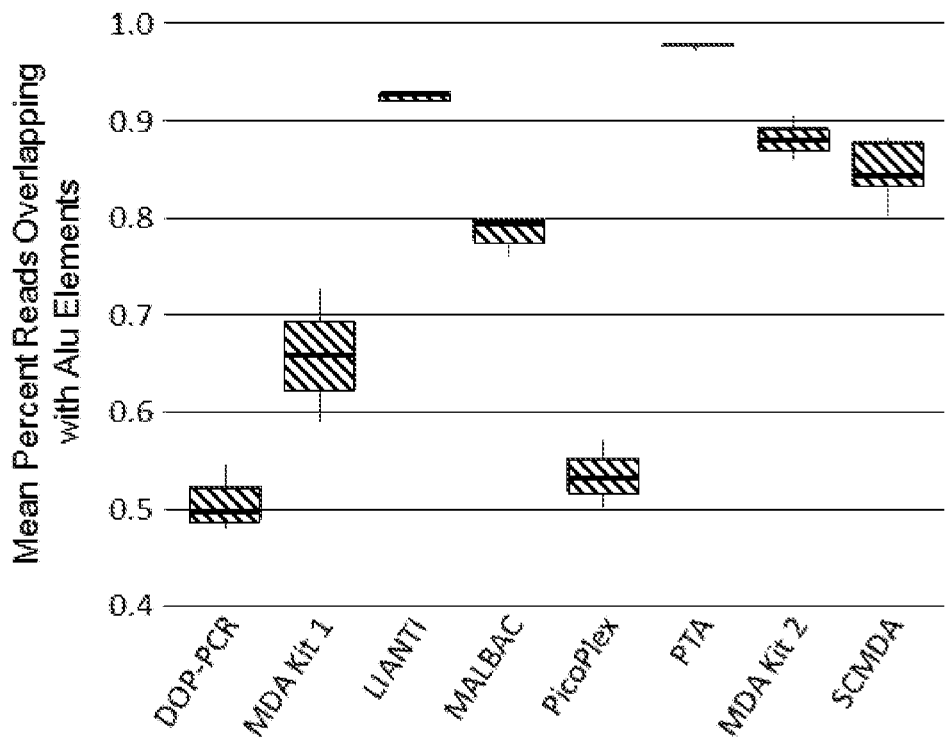
FIG. 3C shows a series of box plots describing aligned reads for the mean percent reads overlapping with Alu elements using various methods. PTA had the highest number of reads aligned to the genome.
Figure 3D:
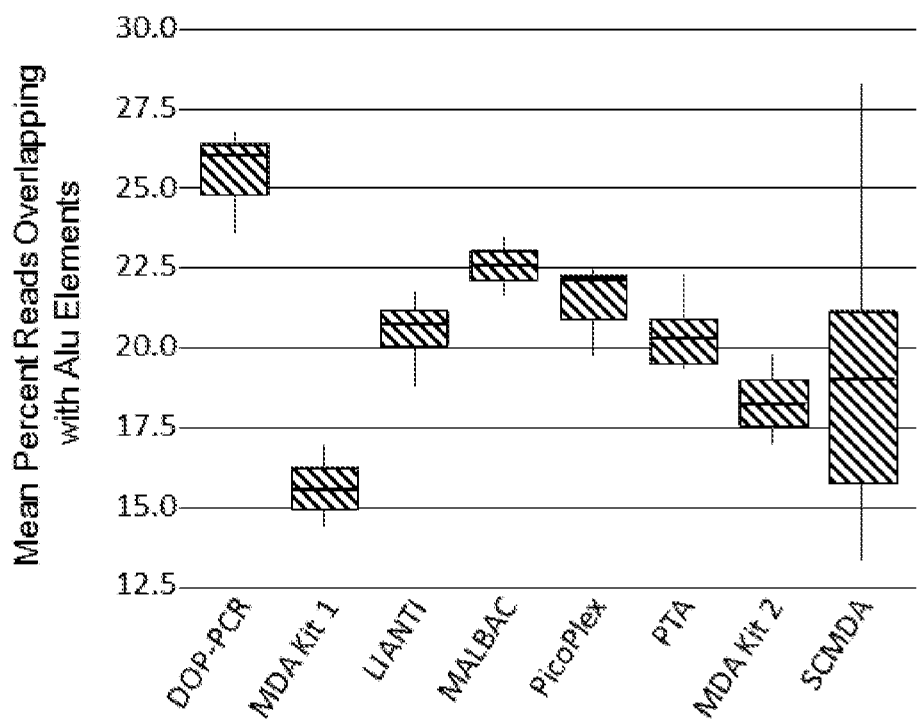
FIG. 3D shows a series of box plots describing PCR duplications for the mean percent reads overlapping with Alu elements using the various methods.
Figure 3E:
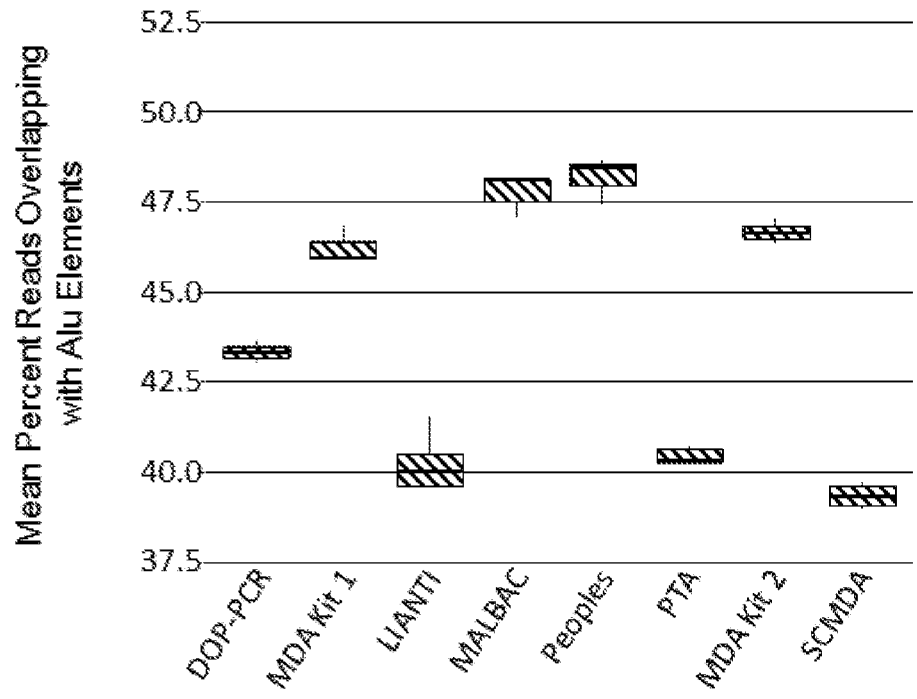
FIG. 3E shows a series of box plots describing GC content of reads for the mean percent reads overlapping with Alu elements using various methods.
Figure 3F:
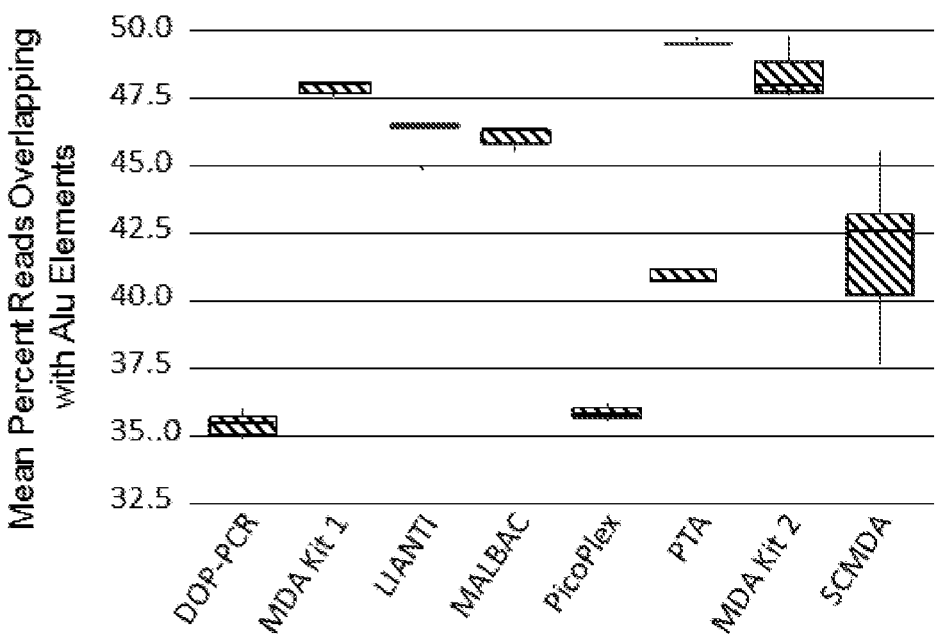
FIG. 3F shows a series of box plots describing the mapping quality of mean percent reads overlapping with Alu elements using various methods. PTA had the highest mapping quality of methods tested.

As shown in FIG. 3A and FIG. 3B, the mapping rates and mapping quality scores of the amplification with dideoxynucleotides ("reversible") alone are 15.0+/−2.2 and 0.8+/−0.08, respectively, while the incorporation of exonuclease-resistant alpha-thio dideoxynucleotide terminators ("irreversible") results in mapping rates and quality scores of 97.9+/−0.62 and 46.3+/−3.18, respectively. Experiments were also run using a reversible ddNTP, and different concentrations of terminators. (FIG. 2A, bottom)

Figure 4A:
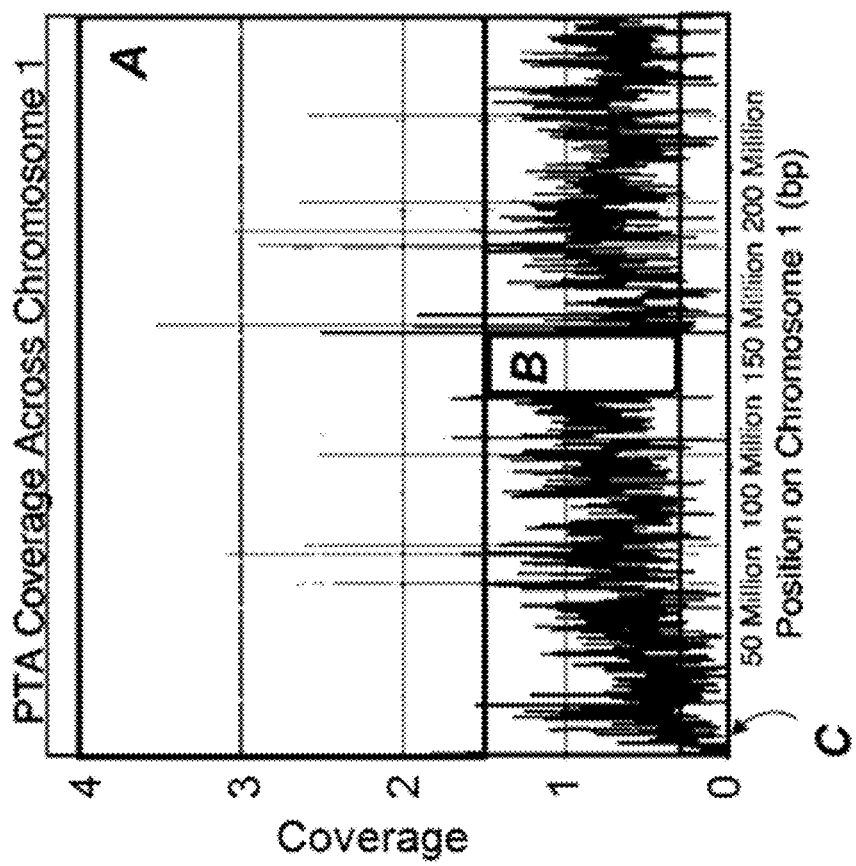
FIG. 4A shows mean coverage depth of 10 kilobase windows across chromosome 1 after selecting for a high quality MDA cell (representative of ~50% cells) compared to a random primer PTA-amplified cell after downsampling each cell to 40 million paired reads. The figure shows that MDA has less uniformity with many more windows that have more (box A) or less (box C) than twice the mean coverage depth. There is absence of coverage in both MDA and PTA at the centromere due to high GC content and low mapping quality of repetitive regions (box B).
Figure 4A:
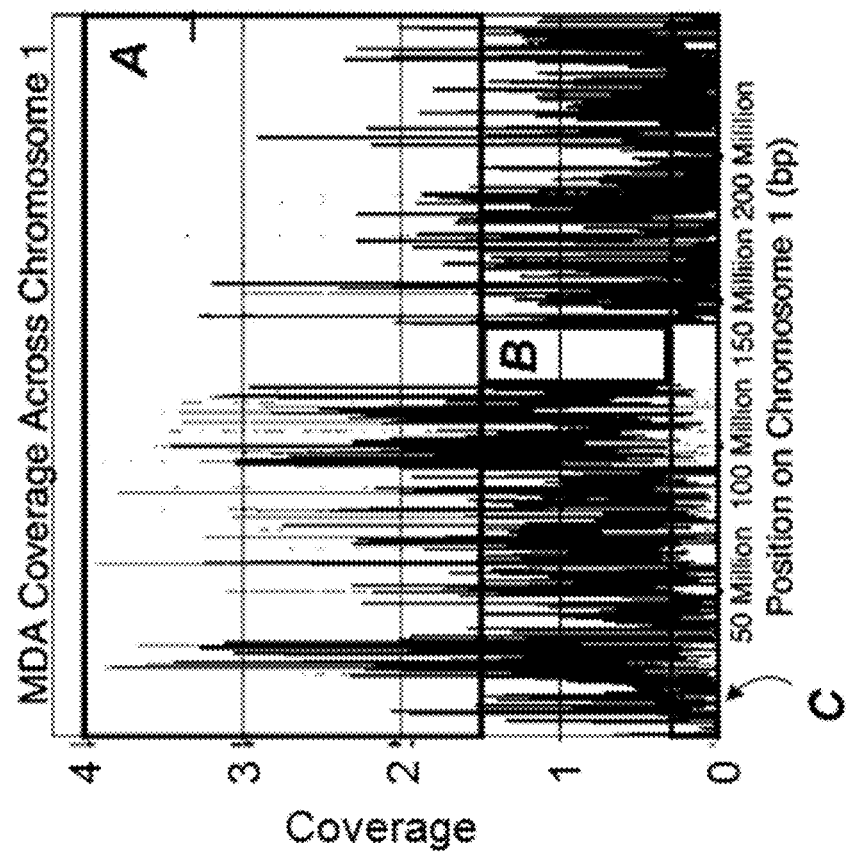

FIGS. 2B-2E show the comparative data produced from NA12878 human single cells that underwent MDA (following the method of Dong, X. et al., Nat Methods. 2017, 14(5):491-493) or PTA. While both protocols produced comparable low PCR duplication rates (MDA 1.26%+/−0.52 vs PTA 1.84%+/−0.99). and GC % (MDA 42.0+/−1.47 vs PTA 40.33+/−0.45), PTA produced smaller amplicon sizes. The percent of reads that mapped and mapping quality scores were also significantly higher for PTA as compared to MDA (PTA 97.9+/−0.62 vs MDA 82.13+/−0.62 and PTA 46.3+/−3.18 vs MDA 43.2+/−4.21, respectively). Overall, PTA produces more usable, mapped data when compared to MDA. FIG. 4A shows that, as compared to MDA, PTA has significantly improved uniformity of amplification with greater coverage breadth and fewer regions where coverage falls to near 0. The use of PTA allows identifying low frequency sequence variants in a population of nucleic acids, including variants which constitute ≥0.01% of the total sequences. PTA can be successfully used for single cell genome amplification.

Example 2: Comparative Analysis of PTA

Benchmarking PTA and SCMDA Cell Maintenance and Isolation

Lymphoblastoid cells from 1000 Genome Project subject NA12878 (Coriell Institute, Camden, N.J., USA) were maintained in RPMI media, which was supplemented with 15% FBS, 2 mM L-glutamine, 100 units/mL of penicillin, 100 μg/mL of streptomycin, and 0.25 μg/mL of Amphotericin B). The cells were seeded at a density of $3.5 \times 10^5$ cells/ml and split every 3 days. They were maintained in a humidified incubator at 37° C. with 5% $CO_2$. Prior to single cell isolation, 3 mL of suspension of cells that had expanded over the previous 3 days was spun at 300×g for 10 minutes. The pelleted cells were washed three times with 1 mL of cell wash buffer (1×PBS containing 2% FBS without $Mg^{2+}$ or $Ca^{2+}$)) where they were spun sequentially at 300×g, 200×g, and finally 100×g for 5 minutes to remove dead cells. The cells were then resuspended in 500 uL of cell wash buffer, which was followed by staining with 100 nM of Calcein AM and 100 ng/ml of propidium iodide (PI) to distinguish the live cell population. The cells were loaded on a BD FACScan flow cytometer (FACSAria II) that had been thoroughly cleaned with ELIMINase and calibrated using Accudrop fluorescent beads. A single cell from the Calcein AM-positive, PI-negative fraction was sorted in each well of a 96 well plate containing 3 uL of PBS with 0.2% Tween 20. Multiple wells were intentionally left empty to be used as no template controls. Immediately after sorting, the plates were briefly centrifuged and placed on ice. Cells were then frozen at a minimum of overnight at −80° C.

PTA and SCMDA Experiments

WGA Reactions were assembled on a pre-PCR workstation that provides constant positive pressure with HEPA filtered air and which was decontaminated with UV light for 30 minutes before each experiment. MDA was carried according to the SCMDA methodology using the REPLI-g Single Cell Kit according the published protocol (Dong et al. Nat. Meth. 2017, 14, 491-493). Specifically, exonuclease-resistant random primers were added at a final concentration of 12.5 uM to the lysis buffer. 4 uL of the resulting lysis mix was added to the tubes containing the single cells, pipetted three times to mix, briefly spun and incubated on ice for 10 minutes. The cell lysates were neutralized by adding 3 uL of quenching buffer, mixed by pipetting 3 times, centrifuged briefly, and placed on ice. This was followed by addition of 40 ul of amplification mix before incubation at 30° C. for 8 hours after which the amplification was terminated by heating to 65° C. for 3 minutes. PTA was carried out by first further lysing the cells after freeze thawing by adding 2 μl of a prechilled solution of a 1:1 mixture of 5% Triton X-100 and 20 mg/ml Proteinase K. The cells were then vortexed and briefly centrifuged before placing at 40 degrees for 10 minutes. 4 μl of denaturing buffer and 1 μl of 500 μM exonuclease-resistant random primer were then added to the lysed cells to denature the DNA prior to vortexing, spinning, and placing at 65° C. for 15 minutes. 4 μl of room temperature quenching solution was then added and the samples were vortexed and spun down. 56 μl of amplification mix that contained alpha-thio-ddNTPs at equal ratios at a concentration of 1200 μM in the final amplification reaction. The samples were then placed at 30° C. for 8 hours after which the amplification was terminated by heating to 65° C. for 3 minutes. After the SCMDA or PTA amplification, the DNA was purified using AMPure XP magnetic beads at a 2:1 ratio of beads to sample and the yield was measured using the Qubit dsDNA HS Assay Kit with a Qubit 3.0 fluorometer according to the manufacturer's instructions. PTA experiments were also run using reversible ddNTPs, and different concentrations of terminators. (FIG. 2A, top)

Library Preparation 1 ug of SCMDA product was fragmented for 30 minutes according to the HyperPlus protocol after the addition of the conditioning solution. The samples then underwent standard library preparation with 15 uM of unique dual index adapters and 4 cycles of PCR. The entire product of each PTA reaction was used for DNA sequencing library preparation using the KAPA HyperPlus kit without fragmentation. 2.5 uM of unique dual index adapter was used in the ligation, and 15 cycles of PCR were used in the final amplification. The libraries from SCMDA and PTA were then visualized on a 1% Agarose E-Gel. Fragments between 400-700 bp were excised from the gel and recovered using a Gel DNA Recovery Kit. The final libraries were quantified using the Qubit dsDNA BR Assay Kit and Agilent 2100 Bioanalyzer before sequencing on the NovaSeq 6000.

Data Analysis

Data was trimmed using trimmomatic, which was followed by alignment to hg19 using BWA. Reads underwent duplicate marking by Picard, followed by local realignment and base recalibration using GATK 3.5 best practices. All files were downsampled to the specified number of reads using Picard DownSampleSam. Quality metrics were acquired from the final bam file using qualimap, as well as Picard AlignmentMetricsAummary and CollectWgsMetrics. Lorenz curves were drawn and Gini Indices calculated using htSeqTools. SNV calling was performed using UnifiedGenotyper, which were then filtered using the standard recommended criteria (QD<2.0||FS>60.0||MQ<40.0||SOR>4.0||MQRankSum<−12.5||ReadPosRankSum<−8.0). No regions were excluded from the analyses and no other data normalization or manipulations were performed. Sequencing metrics for the methods tested are found in Table 1.

TABLE 1

Comparison of sequencing metrics between methods tested.

| | PTA | MDA Kit 2 | PicoPlex | MALBAC | LIANTI | MDA Kit 1 | DOP PCR |
|---|---|---|---|---|---|---|---|
| % Genome Mapping | 97 | 88 | 55 | 79 | 92 | 65 | 52 |
| % Genome Recovery (300M reads) | 95 | 75 | 43 | 60 | 82 | 73 | 23 |
| % CV of Coverage (300M reads) | 0.8 | 1.8 | 3 | 2.5 | 1.1 | 2 | 3.5 |
| SNV Sensitivity % (300M reads) | 76 | 50 | 15 | 34 | 49 | 46 | 5 |

TABLE 1-continued

Comparison of sequencing metrics between methods tested.

|  | PTA | MDA Kit 2 | PicoPlex | MALBAC | LIANTI | MDA Kit 1 | DOP PCR |
|---|---|---|---|---|---|---|---|
| SNV Specificity % (300M reads) | 93 | 91 | 56 | 47 | 88 | 90 | 35 |

CV = Coefficient of Variation; SNV = Single Nucleotide Variation; values refer to 15X coverage.

Genome Coverage Breadth and Uniformity

Comprehensive comparisons of PTA to all common single-cell WGA methods were performed. To accomplish this, PTA and an improved version of MDA called single-cell MDA (Dong et al. Nat. Meth. 2017, 14, 491-493) (SCMDA) was performed on 10NA12878 cells each. In addition, those results to cells that had undergone amplification with DOP-PCR (Zhang et al. PNAS 1992, 89, 5847-5851), MDA Kit 1 (Dean et al. PNAS 2002, 99, 5261-5266), MDA Kit 2, MALBAC (Zong et al. Science 2012, 338, 1622-1626), LIANTI (Chen et al., Science 2017, 356, 189-194), or PicoPlex (Langmore, Pharmacogenomics 3, 557-560 (2002)) was compared using data that were produced as part of the LIANTI study.

Figure 3G:
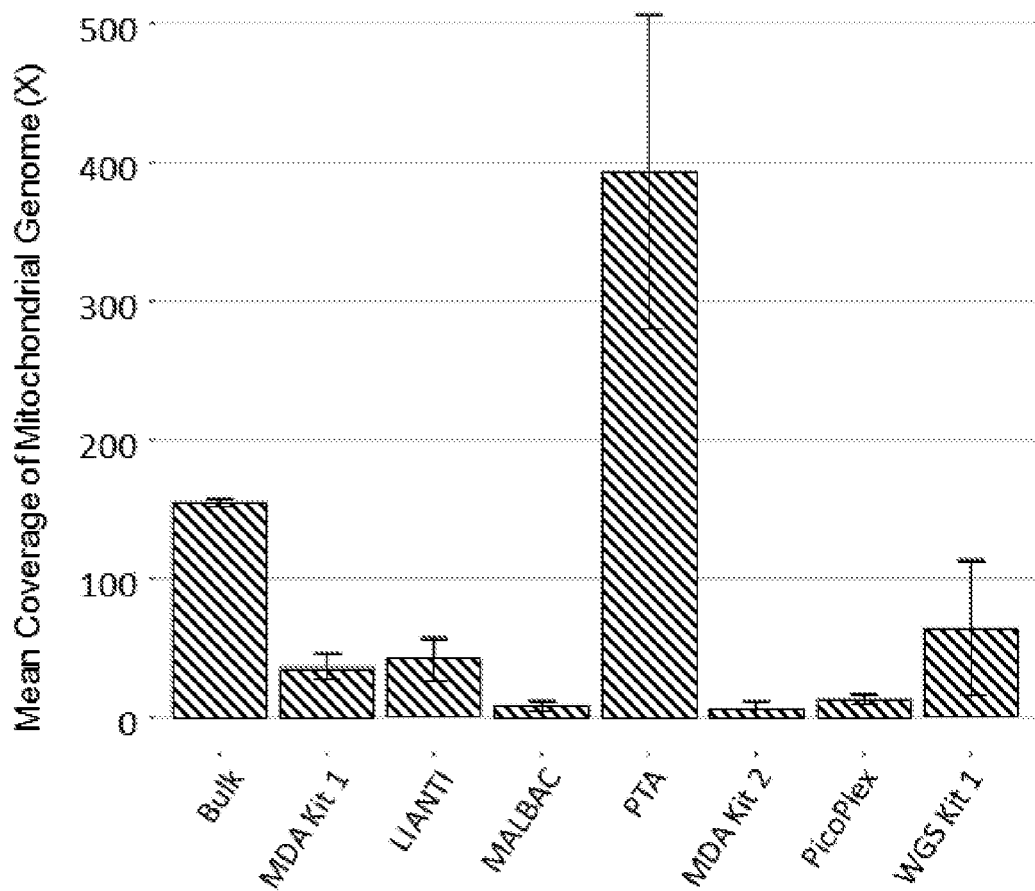
FIG. 3G shows a comparison of SC mitochondrial genome coverage breadth with different WGA methods at a fixed 7.5× sequencing depth.

To normalize across samples, raw data from all samples were aligned and underwent pre-processing for variant calling using the same pipeline. The bam files were then subsampled to 300 million reads each prior to performing comparisons. Importantly, the PTA and SCMDA products were not screened prior to performing further analyses while all other methods underwent screening for genome coverage and uniformity before selecting the highest quality cells that were used in subsequent analyses. Of note, SCMDA and PTA were compared to bulk diploid NA12878 samples while all other methods were compared to bulk BJ1 diploid fibroblasts that had been used in the LIANTI study. As seen in FIGS. 3C-3F, PTA had the highest percent of reads aligned to the genome, as well as the highest mapping quality. PTA, LIANTI, and SCMDA had similar GC content, all of which were lower than the other methods. PCR duplication rates were similar across all methods. Additionally, the PTA method enabled smaller templates such as the mitochondrial genome to give higher coverage rates (similar to larger canonical chromosomes) relative to other methods tested (FIG. 3G).

Figure 4B:
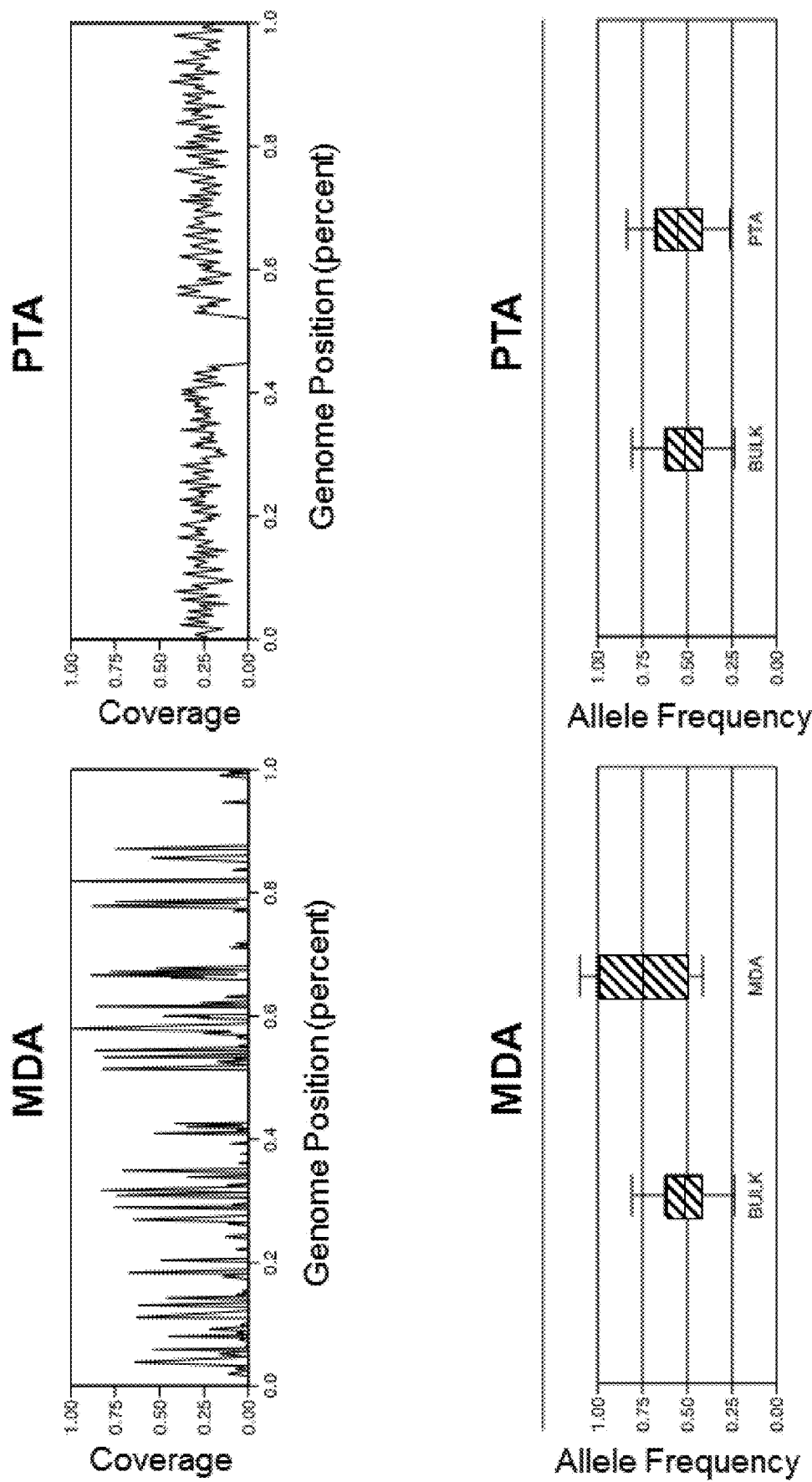
FIG. 4B shows plots of sequencing coverage vs. genome position for MDA and PTA methods (top). The lower box plots show allele frequencies for MDA and PTA methods as compared to the bulk sample.
Figure 4C:
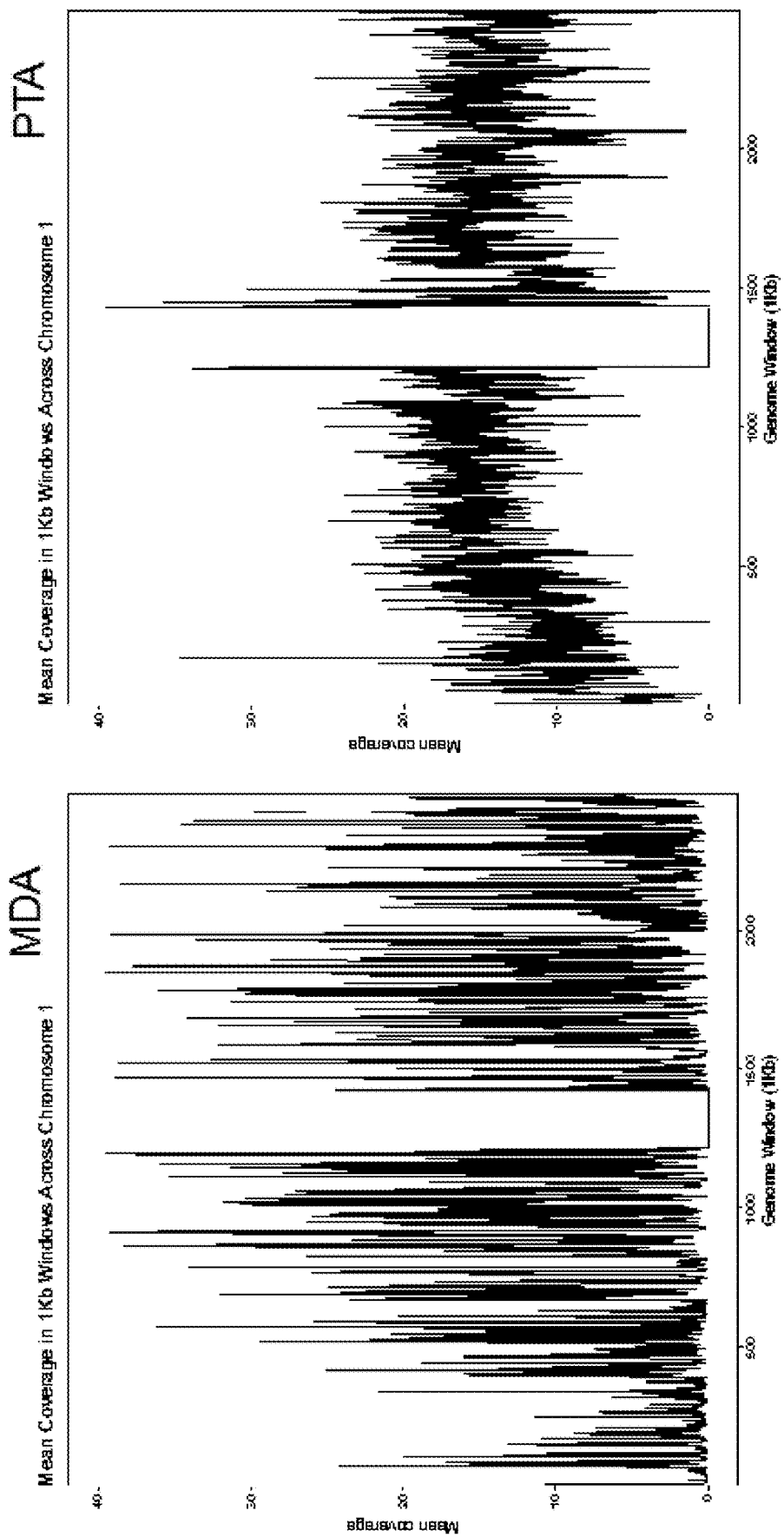
FIG. 4C shows a plot of mean coverage vs. genome window for the uniformity of coverage of MDA and PTA experiments. PTA led to significantly more uniform coverage across the genome than MDA.
Figure 5A:
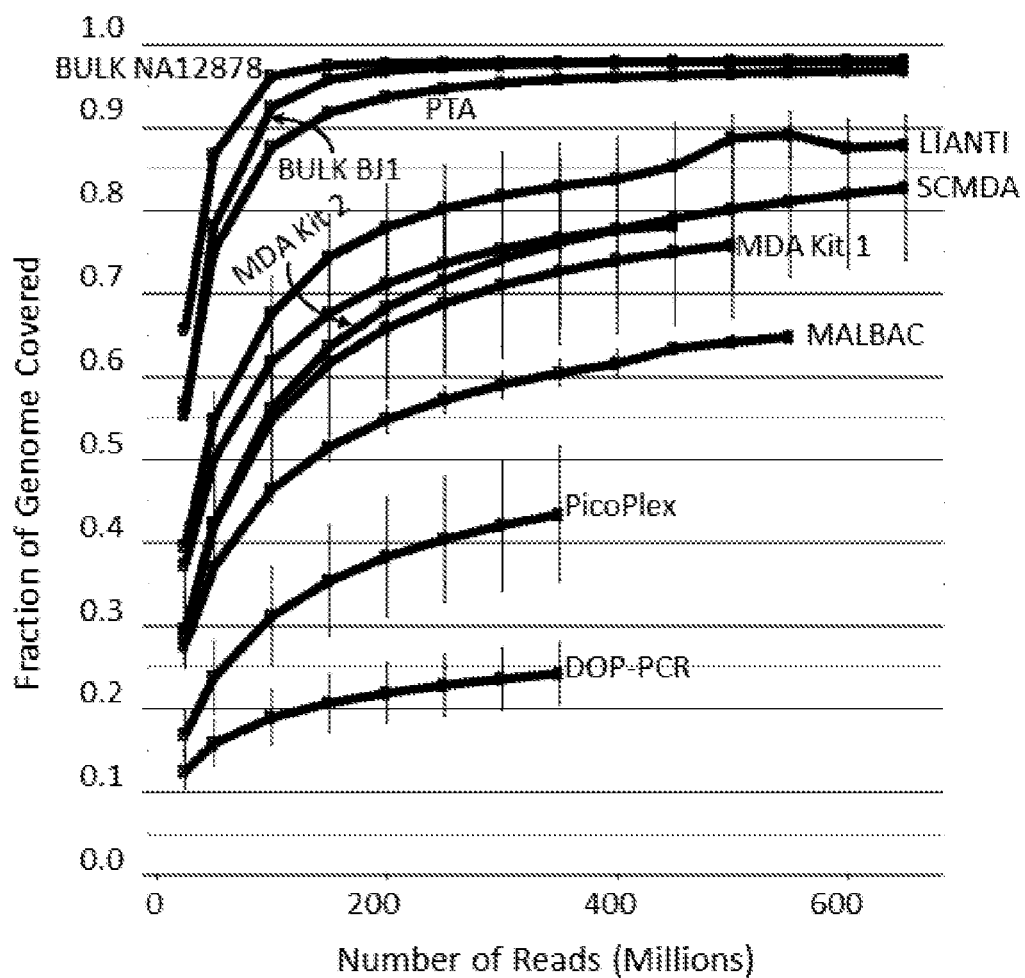
FIG. 5A shows a plot of the fraction of the genome covered vs. number of reads genome to evaluate the coverage at increasing sequencing depth for a variety of methods. The PTA method approaches the two bulk samples at every depth, which is an improvement over other methods tested.
Figure 5B:
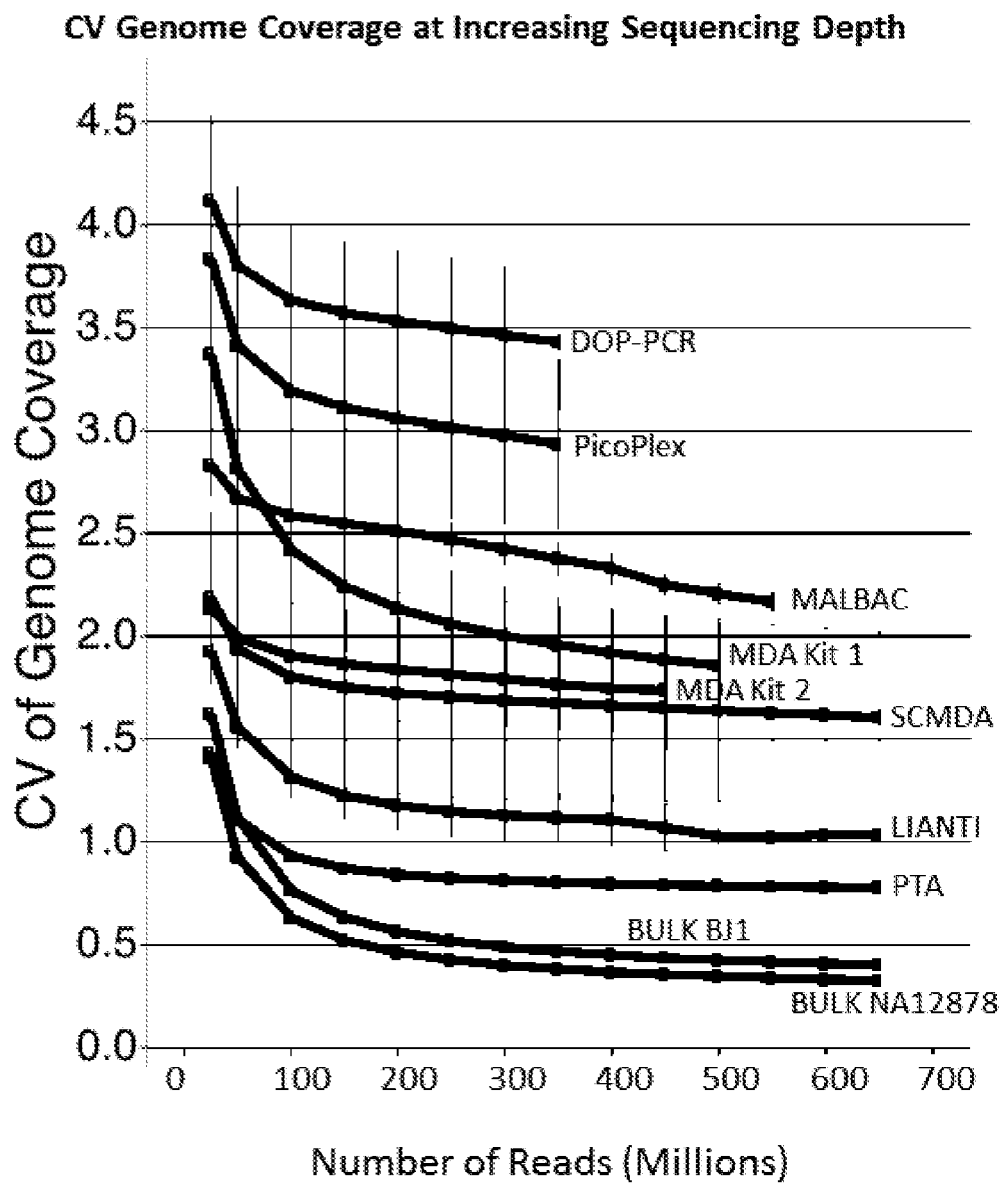
FIG. 5B shows a plot of the coefficient of variation of the genome coverage vs. number of reads to evaluate coverage uniformity. The PTA method was found to have the highest uniformity of the methods tested.
Figure 5C:
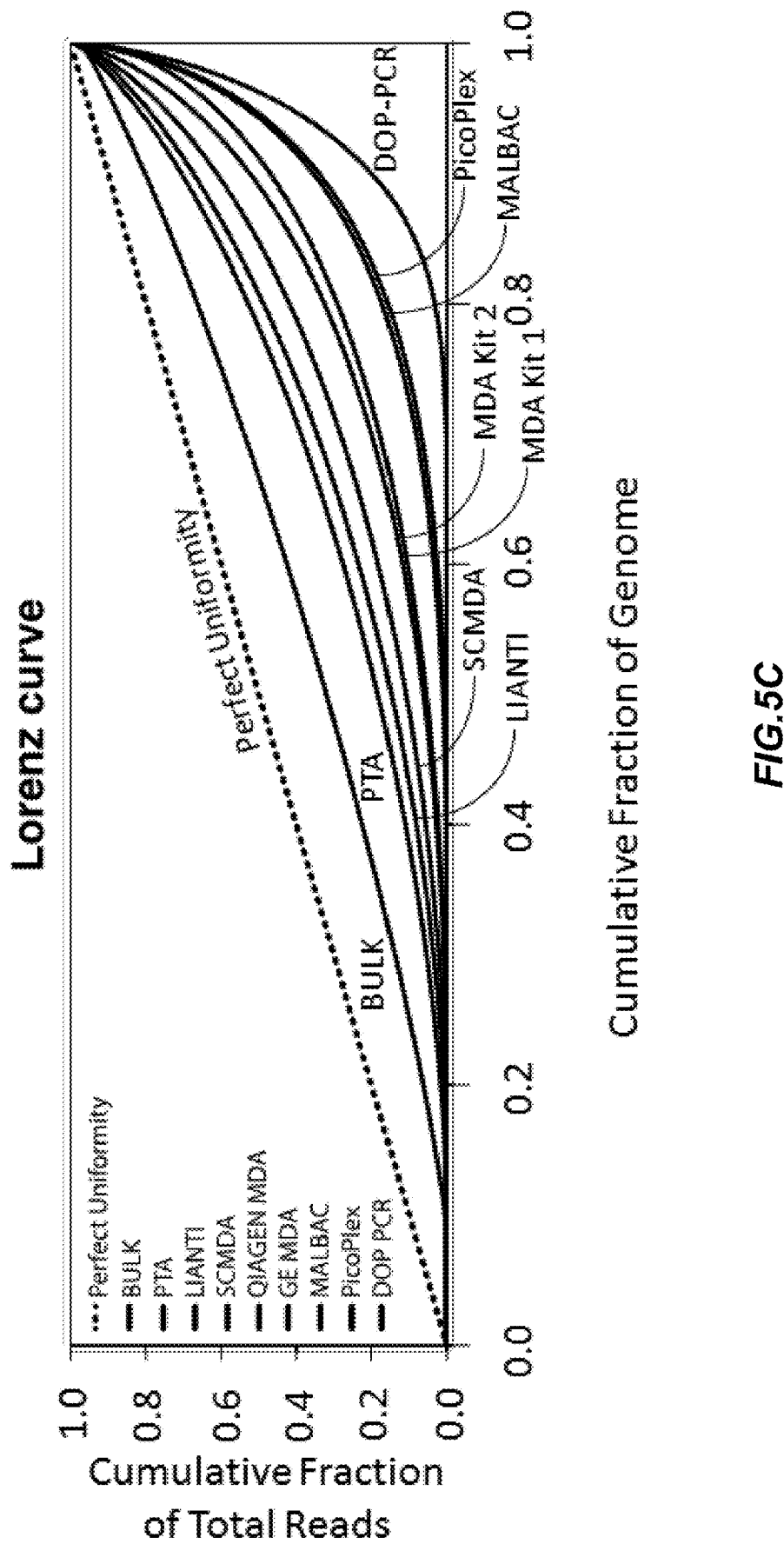
FIG. 5C shows a Lorenz plot of the cumulative fraction of the total reads vs. the cumulative fraction of the genome. The PTA method was found to have the highest uniformity of the methods tested.
Figure 5D:
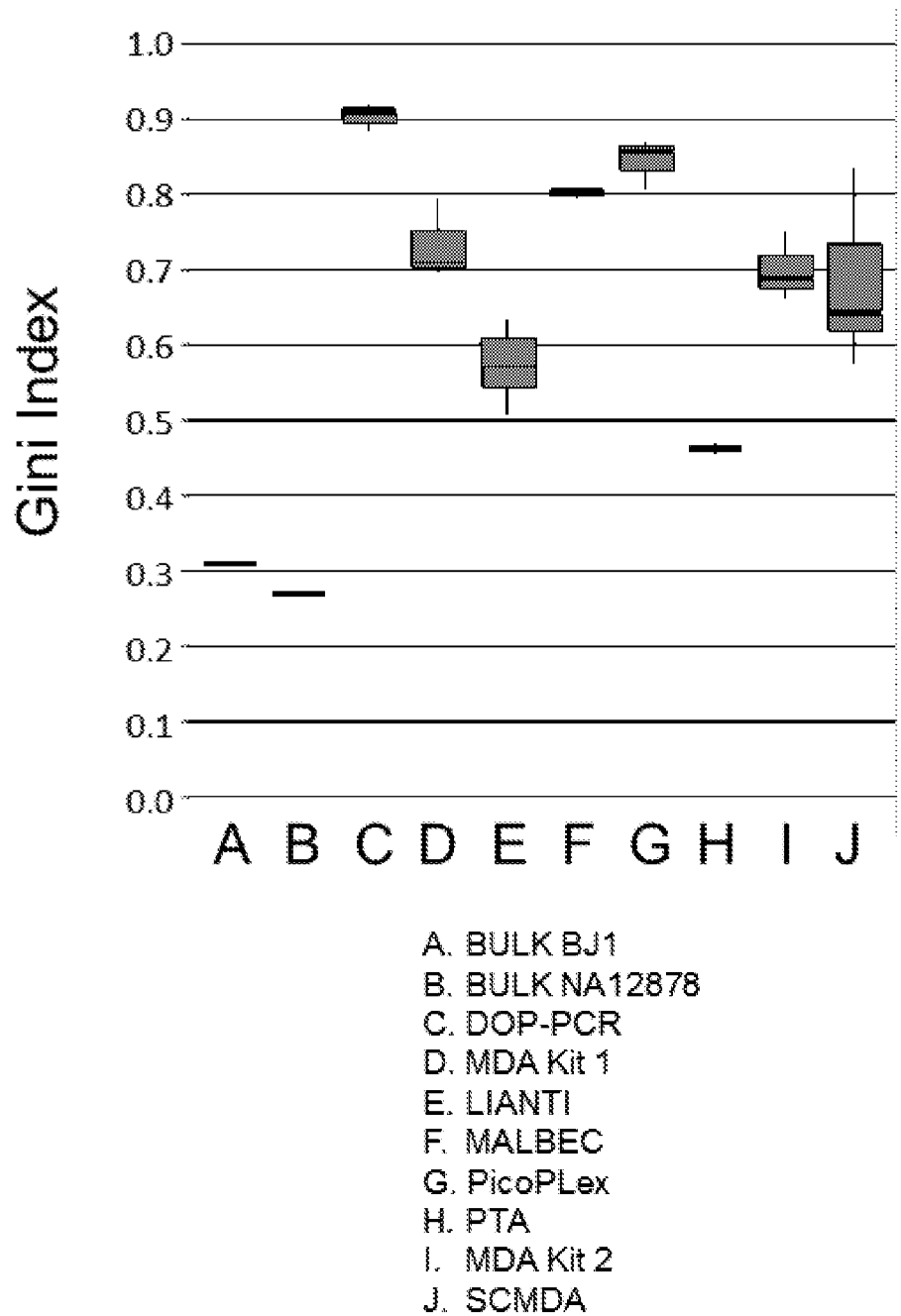
FIG. 5D shows a series of box plots of calculated Gini Indices for each of the methods tested in order to estimate the difference of each amplification reaction from perfect uniformity. The PTA method was found to be reproducibly more uniform than other methods tested.

Coverage breadth and uniformity of all methods was then compared. Examples of coverage plots across chromosome 1 are shown for SCMDA and PTA, where PTA is shown to have significantly improved uniformity of coverage (FIGS. 4B and 4C). Coverage rates were then calculated for all methods using increasing number of reads. PTA approaches the two bulk samples at every depth, which is a significant improvement over all other methods (FIG. 5A). We then used two strategies to measure coverage uniformity. The first approach was to calculate the coefficient of variation of coverage at increasing sequencing depth where PTA was found to be more uniform than all other methods (FIG. 5B). The second strategy was to compute Lorenz curves for each subsampled bam file where PTA was again found to have the greatest uniformity (FIG. 5C). To measure the reproducibility of amplification uniformity, Gini Indices were calculated to estimate the difference of each amplification reaction from perfect uniformity (de Bourcy et al., PloS one 9, e105585 (2014)). PTA was again shown to be reproducibly more uniform than the other methods (FIG. 5D).

SNV Sensitivity

Figure 5E:
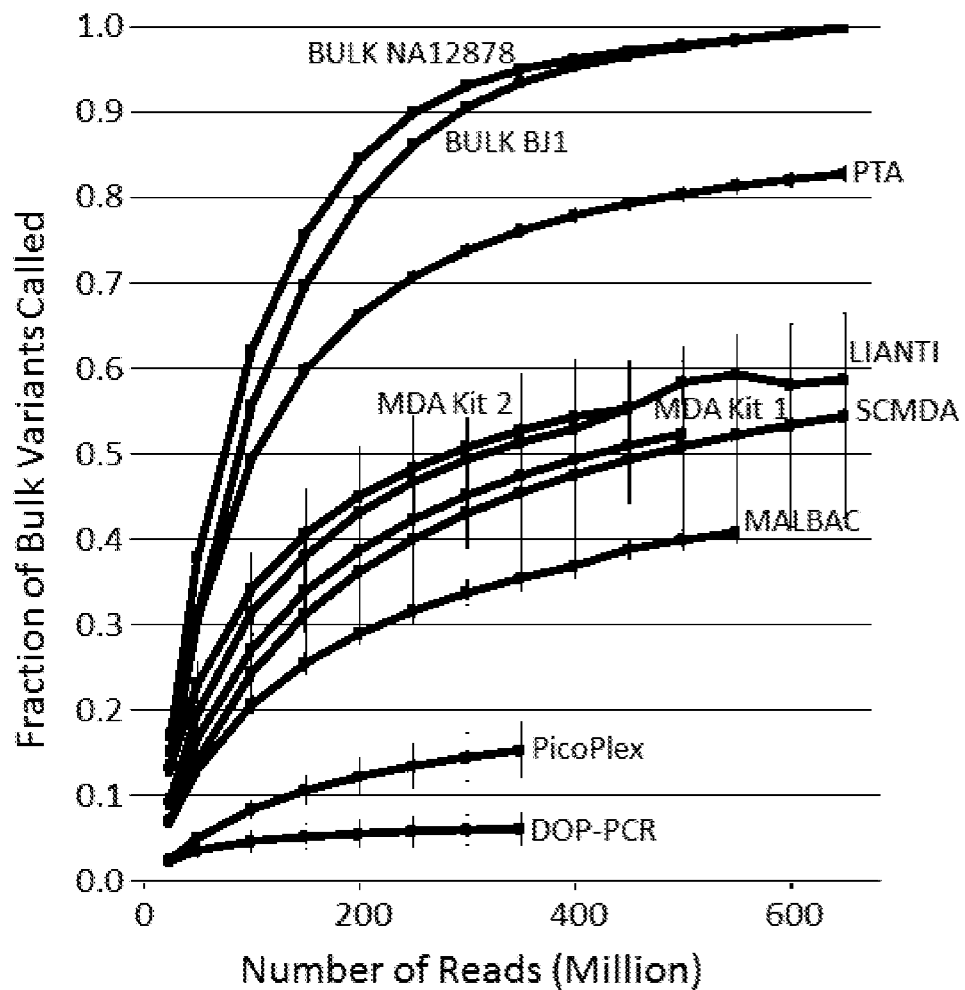
FIG. 5E shows a plot of the fraction of bulk variants called vs. number of reads. Variant call rates for each of the methods were compared to the corresponding bulk sample at increasing sequencing depth. To estimate sensitivity, the percent of variants called in corresponding bulk samples that had been subsampled to 650 million reads found in each cell at each sequencing depth (FIG. 3A) were calculated. Improved coverage and uniformity of PTA resulted in the detection of 30% more variants over the Q-MDA method, which was the next most sensitive method.
Figure 5F:
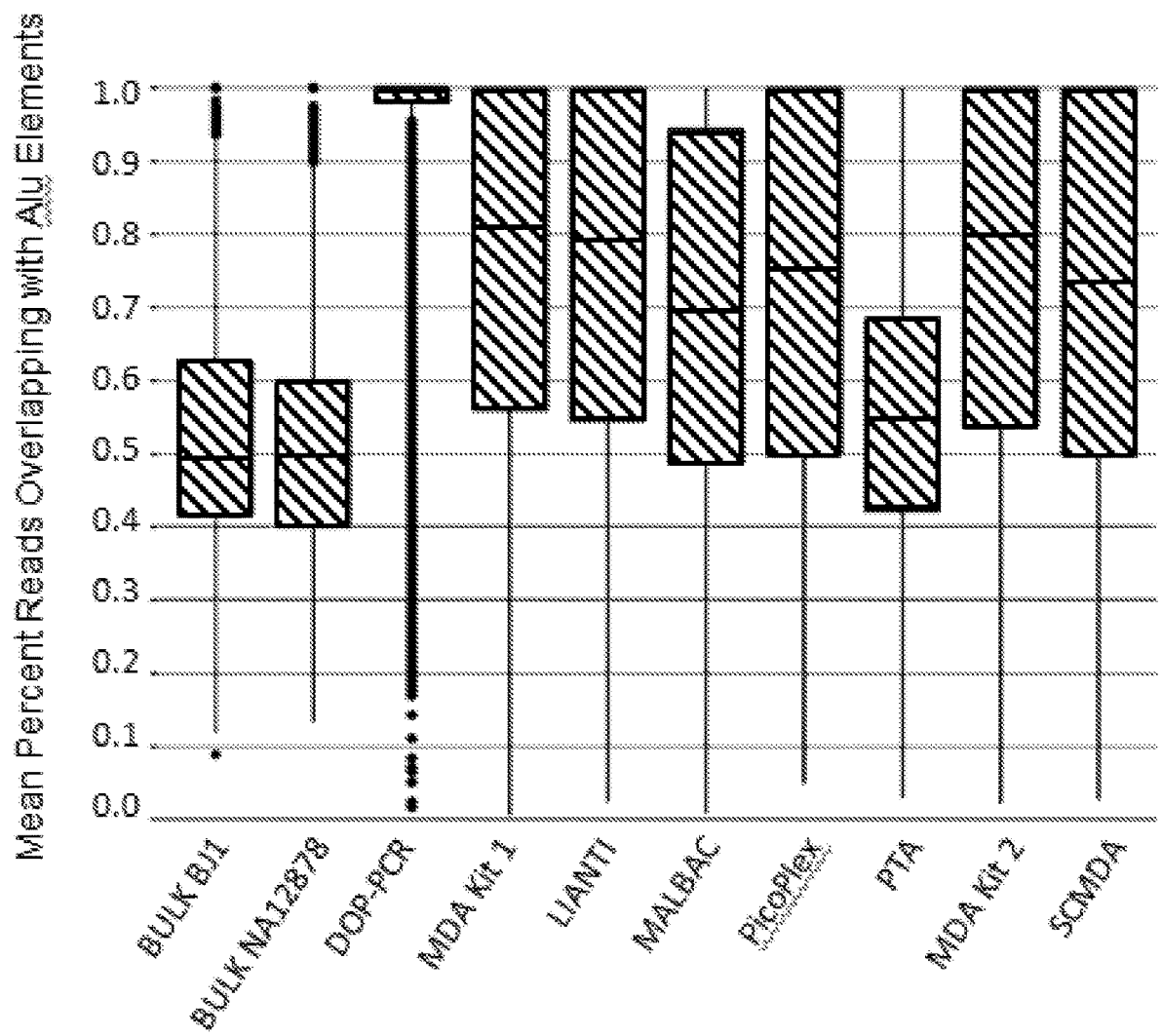
FIG. 5F shows a series of box plots of the mean percent reads overlapping with Alu elements. The PTA method significantly diminished allelic skewing at these heterozygous sites. The PTA method more evenly amplifies two alleles in the same cell relative to other methods tested.

To determine the effects of these differences in the performance of the amplification methods on SNV calling, variant call rates for each to the corresponding bulk sample were compared at increasing sequencing depth. To estimate sensitivity, the percent of variants called in corresponding bulk samples that had been subsampled to 650 million reads that were found in each cell at each sequencing depth (FIG. 5E) were compared. Improved coverage and uniformity of PTA resulted in the detection of 45.6% more variants over MDA Kit 2, which was the next most sensitive method. An examination of sites called as heterozygous in the bulk sample showed that PTA had significantly diminished allelic skewing at those heterozygous sites (FIG. 5F). This finding supports the assertion that PTA not only has more even amplification across the genome, but also more evenly amplifies two alleles in the same cell.

SAW Specificity

Figure 5G:
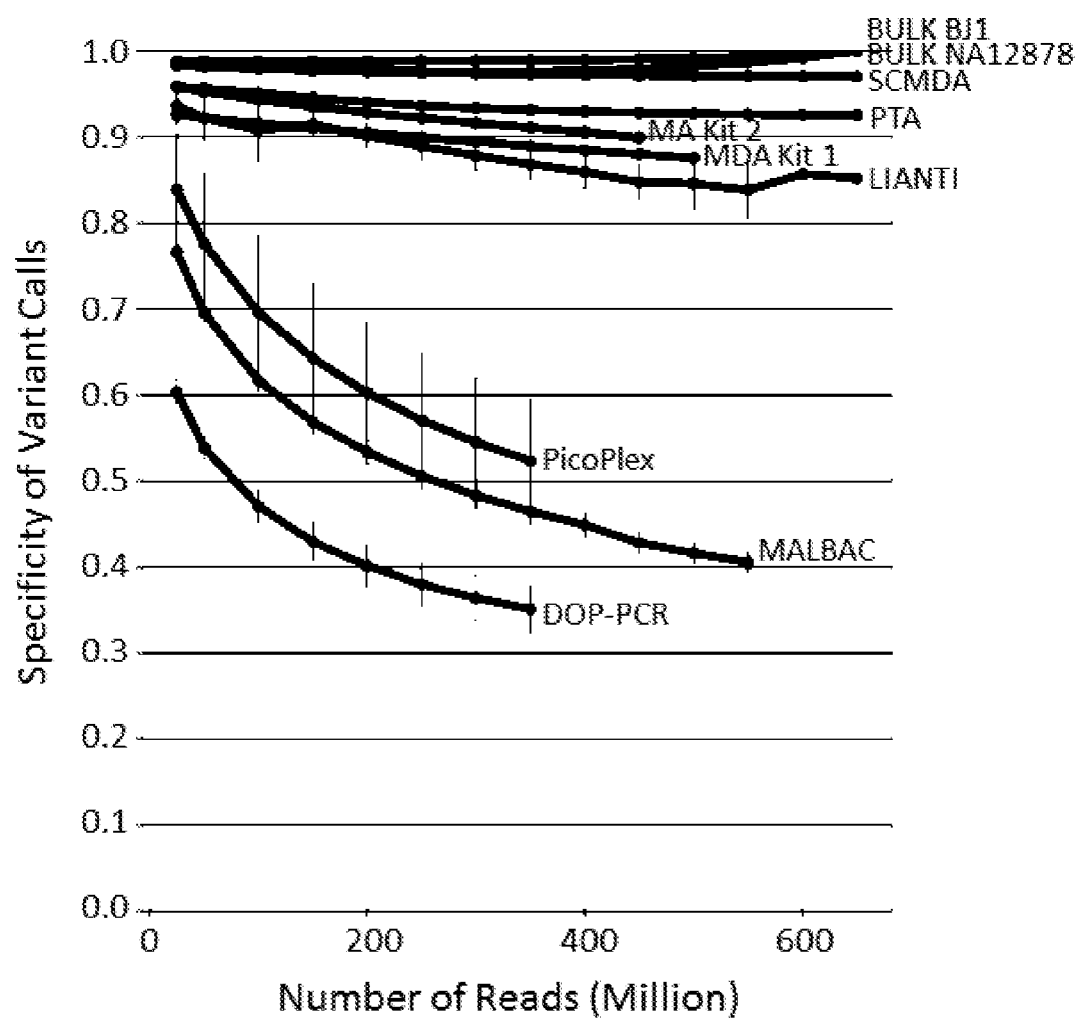
FIG. 5G shows a plot of specificity of variant calls vs. number of reads to evaluate the specificity of mutation calls. Variants found using various methods which were not found in the bulk samples were considered as false positives. The PTA method resulted in the lowest false positive calls (highest specificity) of methods tested.
Figure 5H:
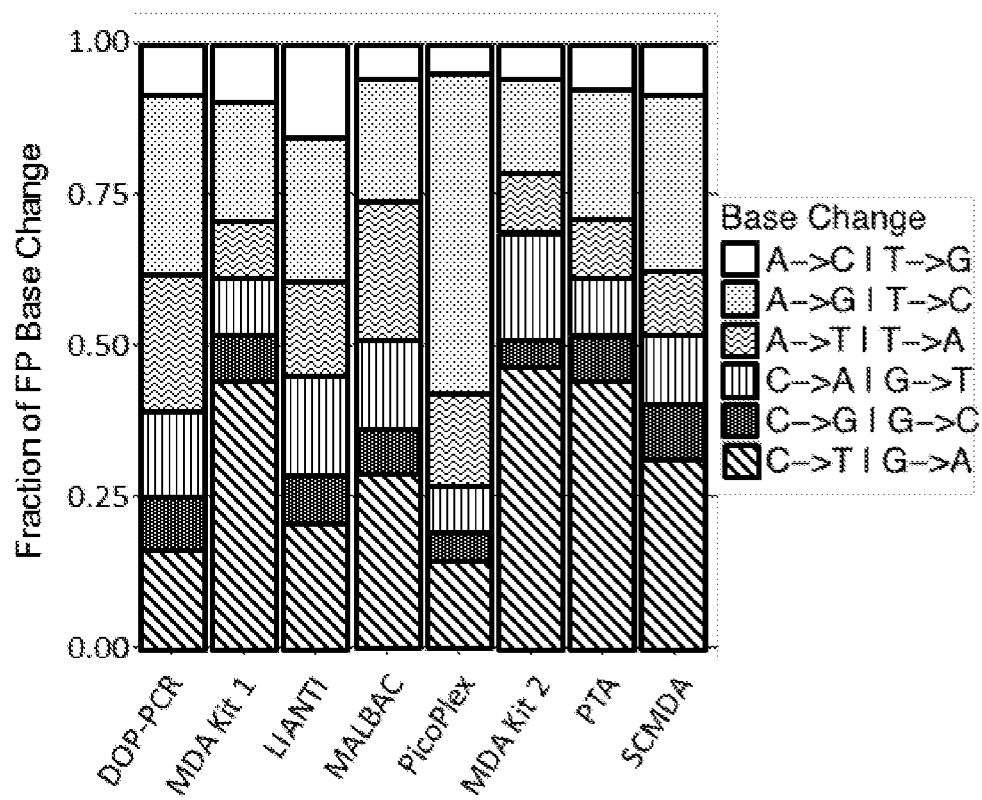
FIG. 5H shows the fraction of false positive base changes for each type of base change across various methods. Without being bound by theory, such patterns may be polymerase dependent.
Figure 5I:
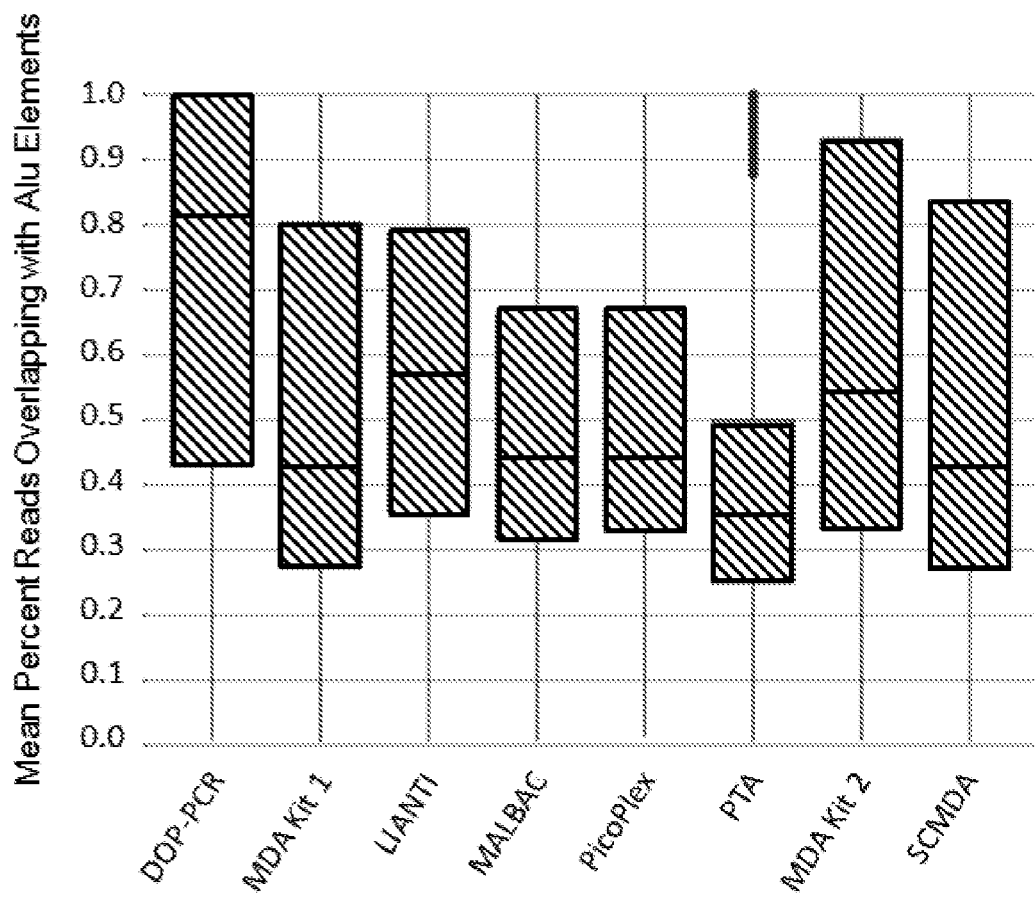
FIG. 5I shows a series of box plots of the mean percent reads overlapping with Alu elements for false positives variant calls. The PTA method resulted in the lowest allele frequencies for false positive variant calls.

To estimate the specificity of mutation calls, the variants called in each single cell not found in the corresponding bulk sample were considered false positives. The lower temperature lysis of SCMDA significantly reduced the number of false positive variant calls (FIG. 5G). Methods using thermostable polymerases (MALBAC, PicoPlex, and DOP-PCR) showed further decreases in the SNV calling specificity with increasing sequencing depth. Without being bound by theory, this is likely the result of the significantly increased error rate of those polymerases compared to phi29 DNA polymerase. In addition, the base change patterns seen in the false positive calls also appear to be polymerase-dependent (FIG. 5H). As seen in FIG. 5G, the model of suppressed error propagation in PTA is supported by the lower false positive SNV calling rate in PTA compared to standard MDA protocols. In addition, PTA has the lowest allele frequencies of false positive variant calls, which is again consistent with the model of suppressed error propagation with PTA (FIG. 5I).

Example 3: Direct Measurement of Environmental Mutagenicity (DMEM)

PTA was used to conduct a novel mutagenicity assay that provides a framework for performing high-resolution, genome wide human toxicogenomics studies. Previous studies such as the Ames test, relies on bacterial genetics to make measurements that are assumed to be representative of human cells while only providing limited information on the mutation number and patterns induced in each exposed cell. To overcome these limitations, a human mutagenesis system "direct measurement of environmental mutagenicity (DMEM)" was developed, wherein single human cells was exposed to an environmental compound, isolated as single cells, and subjected to single-cell sequencing to identify the new mutations induced in each cell.

Umbilical cord blood cells that express the stem/progenitor marker CD34 were exposed to increasing concentrations of the direct mutagen N-ethyl-N-nitrosourea (ENU). ENU is known to have a relatively low Swain-Scott substrate constant and has consequently been shown to predominantly act through a two-step SN1 mechanism that results in preferential alkylation of 04-thymine, O2-thymine, and O2-cytosine. Through limited sequencing of target genes, ENU has also been shown to have preference for T to A (A to T), T to C (A to G), and C to T (G to A) changes in mice, which significantly differs from the pattern seen in E. coli.

Isolation and Expansion of Cord Blood Cells for Mutagenicity Experiments

ENU (CAS 759-73-9) and D-mannitol (CAS 69-65-8) were put into solution at their maximal solubility. Fresh anticoagulant-treated umbilical cord blood (CB) was obtained from St. Louis Cord Blood Bank. CB was diluted 1:2 with PBS and mononuclear cells (MNCs) were isolated by density gradient centrifugation on Ficoll-Paque Plus according to manufacturer's instructions. CB MNCs expressing CD34 were then immunomagnetically selected using the human CD34 microbead kit and magnetic cell sorting (MACS) system as per the manufacturer. Cell count and viability were assessed using the Luna FL cell counter. CB CD34+ cells were seeded at a density of $2.5 \times 10^4$ cells/mL in StemSpan SFEM supplemented with 1×CD34+ Expansion supplement, 100 units/mL of penicillin, and 100 ug/mL of streptomycin where they expanded for 96 hours before proceeding to mutagen exposure.

Direct Measurement of Environmental Mutagenicity (DMEM)

Expanded cord blood CD34+ cells were cultured in StemSpan SFEM supplemented with 1×CD34+ Expansion Supplement, 100 units/mL of penicillin, and 100 ug/mL of streptomycin. The cells were exposed to ENU at concentrations of 8.54, 85.4, and 854 uM, D-mannitol at 1152.8, and 11528 uM, or 0.9% sodium chloride (vehicle control) for 40 hours. Single-cell suspensions from drug-treated cells and vehicle control samples were harvested and stained for viability as described above. Single cell sorts were carried out as described above. PTA was performed and libraries were prepared using a simplified and improved protocol as per the general methods of the methods described herein, and Example 2.

Analysis of DMEM Data

Data acquired from cells in the DMEM experiments were trimmed using Trimmomatic, aligned to GRCh38 using BWA, and further processed using GATK 4.0.1 best practices without deviation from the recommended parameters. Genotyping was performed using HaplotypeCaller where joint genotypes were again filtered using standard parameters. A variant was only considered to be the result of the mutagen if it had a Phred quality score of at least 100 and was only found in one cell while not being found in the bulk sample. The trinucleotide context of each SNV was determined by extracting the surrounding bases from the reference genome using bedtools. Mutation counts and context were visualized using ggplot2 and heatmap2 in R.

To determine whether mutations were enriched in DNase I hypersensitivity sites (DHS) in CD34+ cells, the proportion of SNVs in each sample that overlap with DHS sites from 10 CD34+ primary cell datasets produced by the Roadmap Epigenomics Project were calculated. DHS sites were extended by 2 nucleosomes, or 340 bases in either direction. Each DHS dataset was paired with a single cell sample where we determined the proportion of the human genome with at least 10× coverage in that cell which overlapped with a DHS, which was compared to the proportion of SNVs that were found within the covered DHS sites.

Results

Figure 12A:
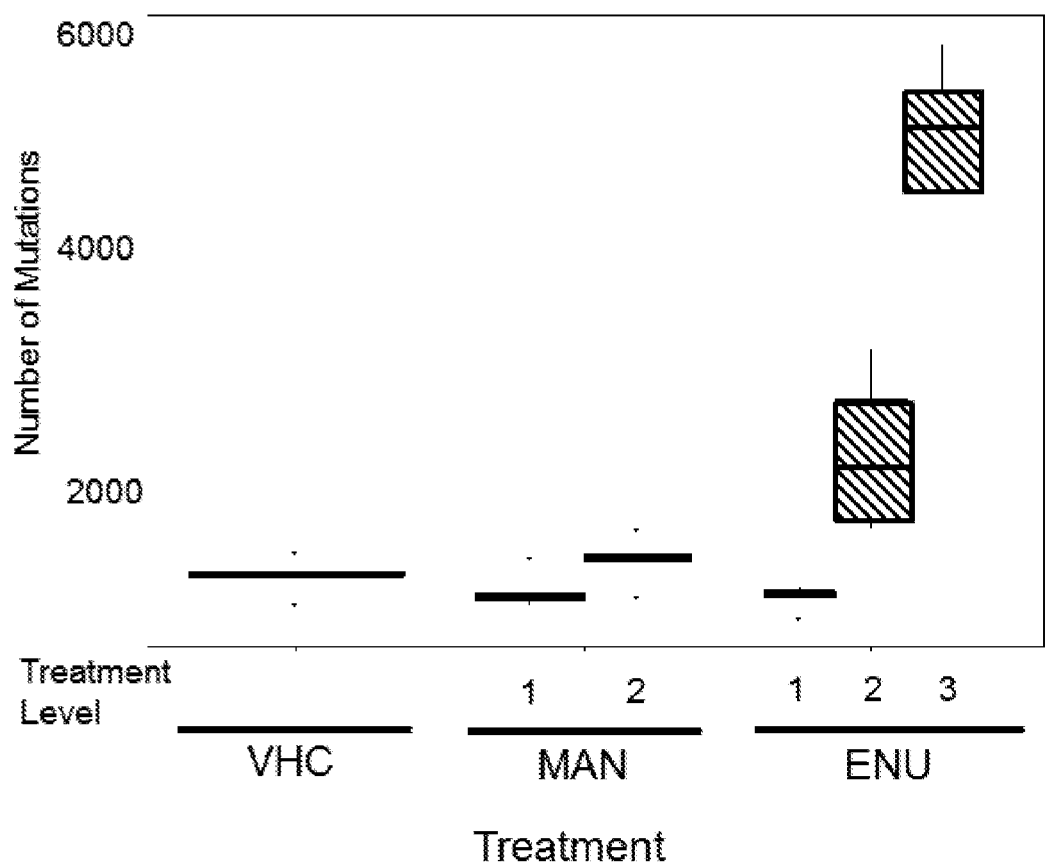
FIG. 12A shows a plot of number of mutations verses treatment groups for a direct measurement of environmental mutagenicity experiment. Single human cells were exposed to vehicle (VHC), mannose (MAN), or the direct mutagen N-ethyl-N-nitrosourea (ENU) at different treatment levels, and the number of mutations measured.
Figure 12B:
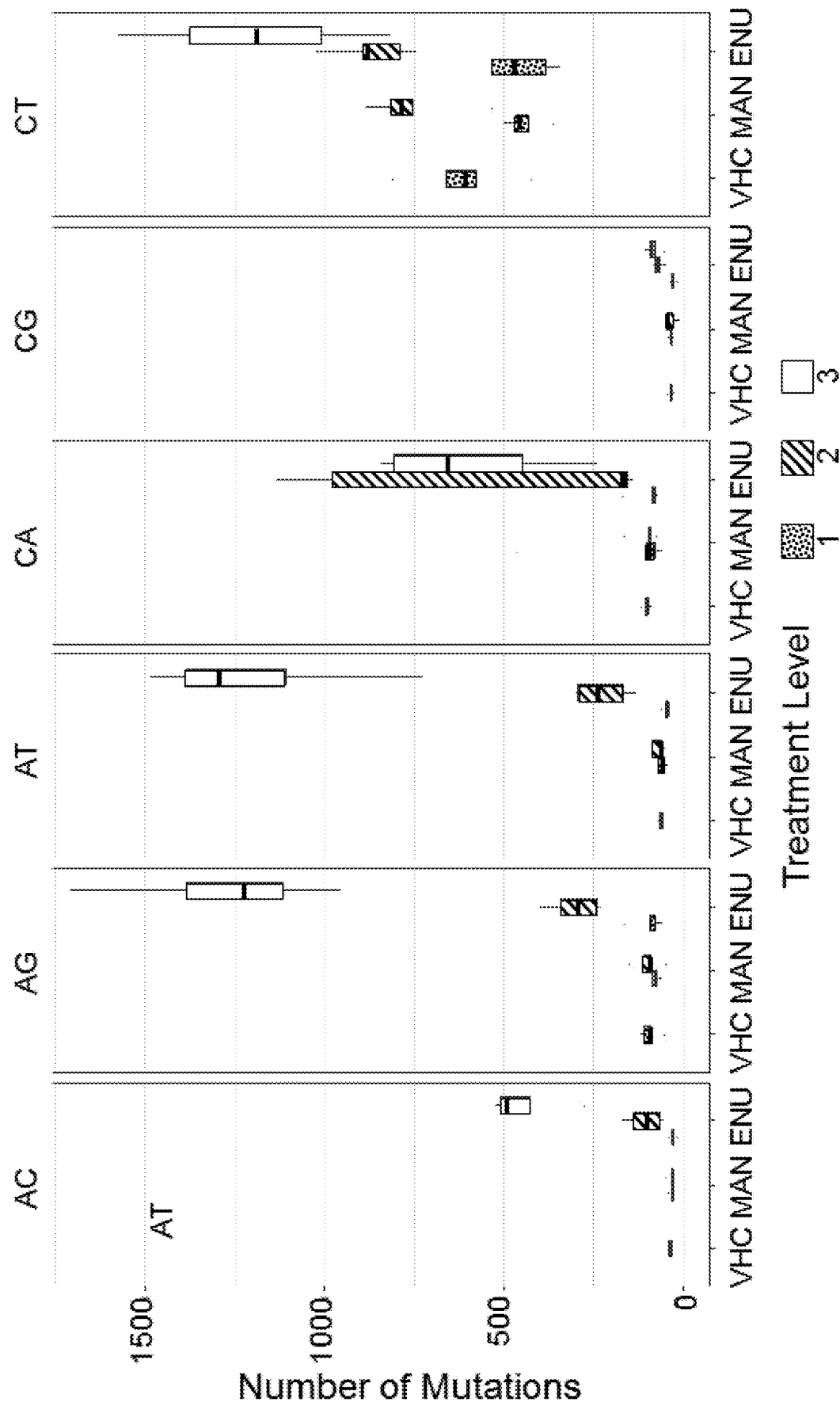
FIG. 12B shows a series of plots of the number of mutations verses different treatment groups and levels, further divided by the type of base mutations.
Figure 12C:
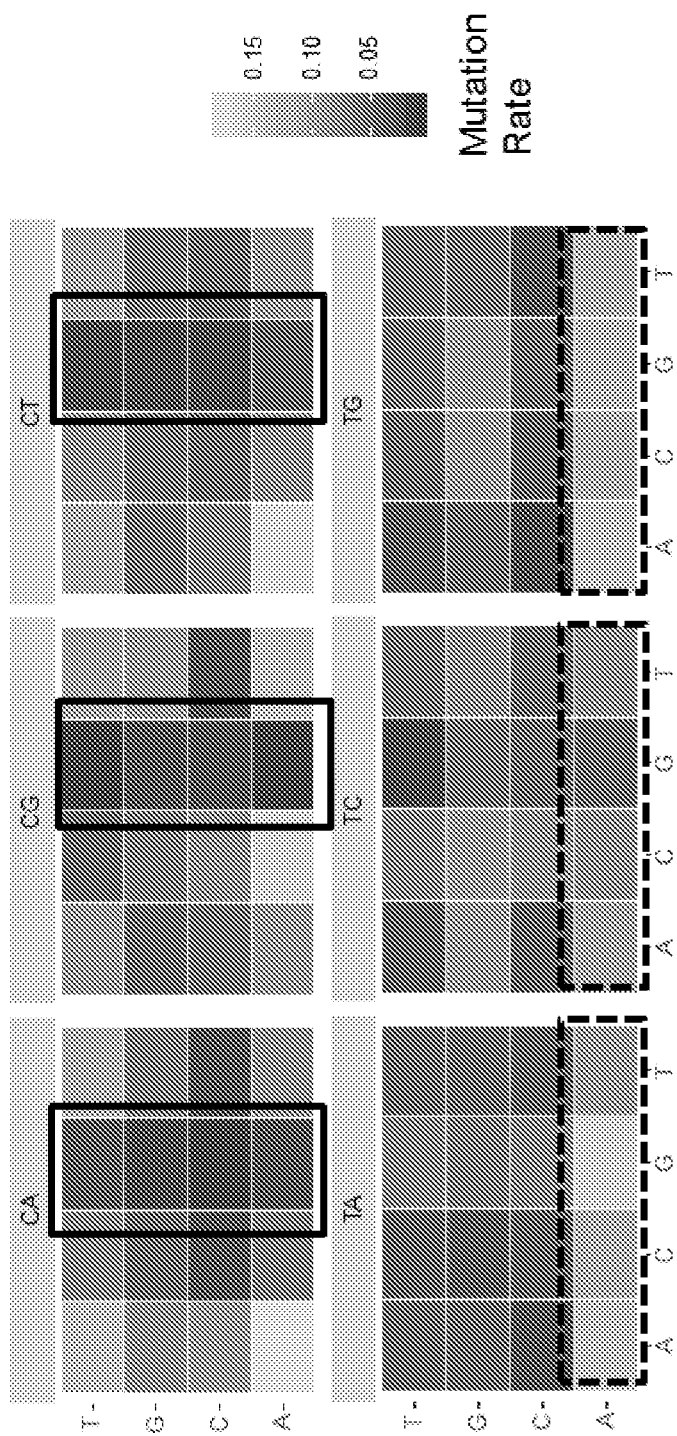
FIG. 12C shows a pattern representation of mutations in a trinucleotide context. Bases on the y axis are at the n−1 position, and bases on the x axis are at the n+1 position. Darker regions indicate a lower mutational frequency, and lighter regions indicate a higher mutational frequency. The solid black boxes in the top row (cytosine mutations) indicate that cytosine mutagenesis is less frequent when the cytosine is followed by a guanine. The dashed black boxes on the bottom row (thymine mutations) indicate most thymine mutations occur in positions where adenine is immediately preceding thymine.
Figure 12D:
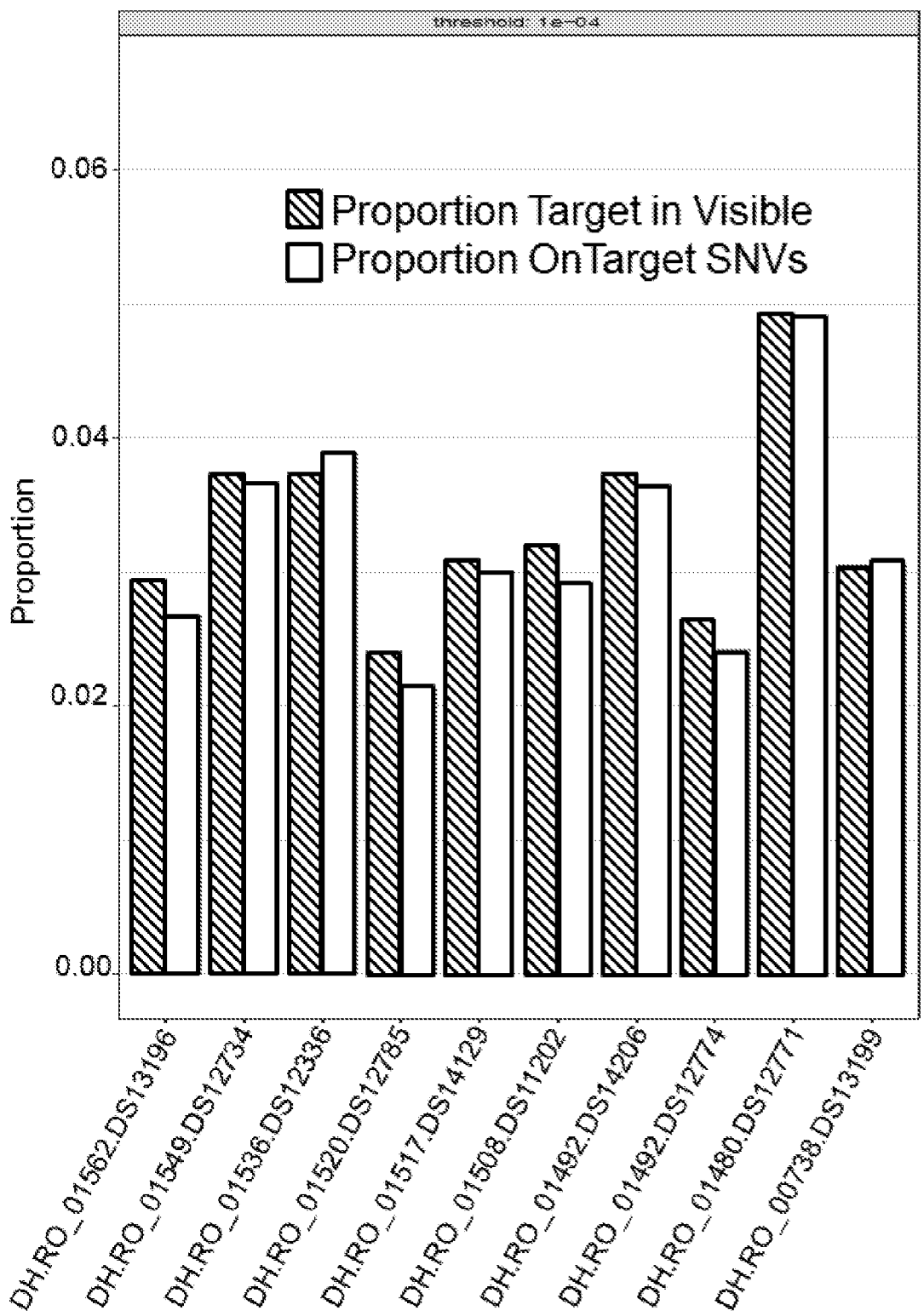
FIG. 12D shows a graph comparing locations of known DNase I hypersensitive sites in CD34+ cells to corresponding locations from N-ethyl-N-nitrosourea treated cells. No significant enrichment of cytosine variants was observed.
Figure 12E:
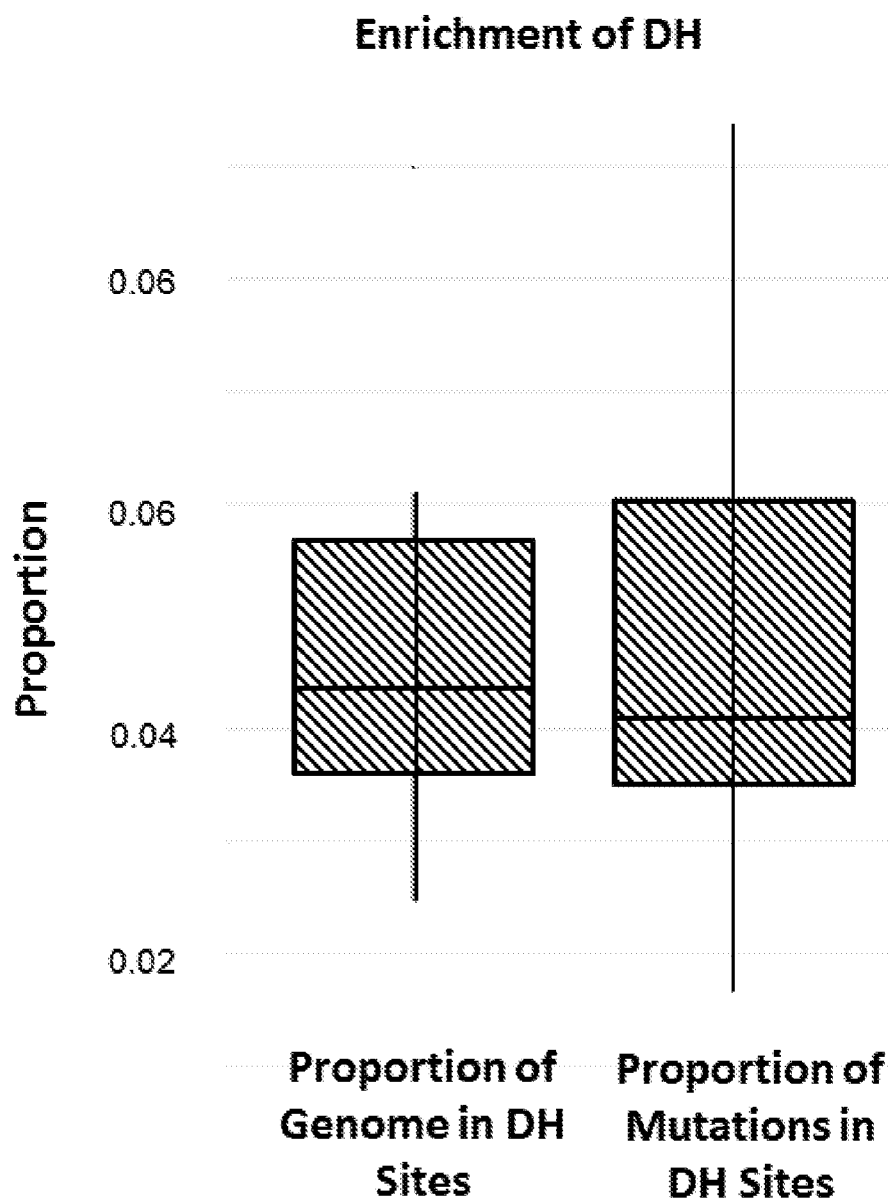
FIG. 12E shows the proportion of ENU induced mutations in DNase I Hypersensitive (DH) sites. DH sites in CD34+ cells previously catalogued by the Roadmap Epigenomics Project were used to investigate whether ENU mutations are more prevalent in DH sites which represent sites of open chromatin. No significant enrichment in variant locations at DH sites was identified, and no enrichment of variants restricted to cytosines was observed in DH sites.
Figure 12F:
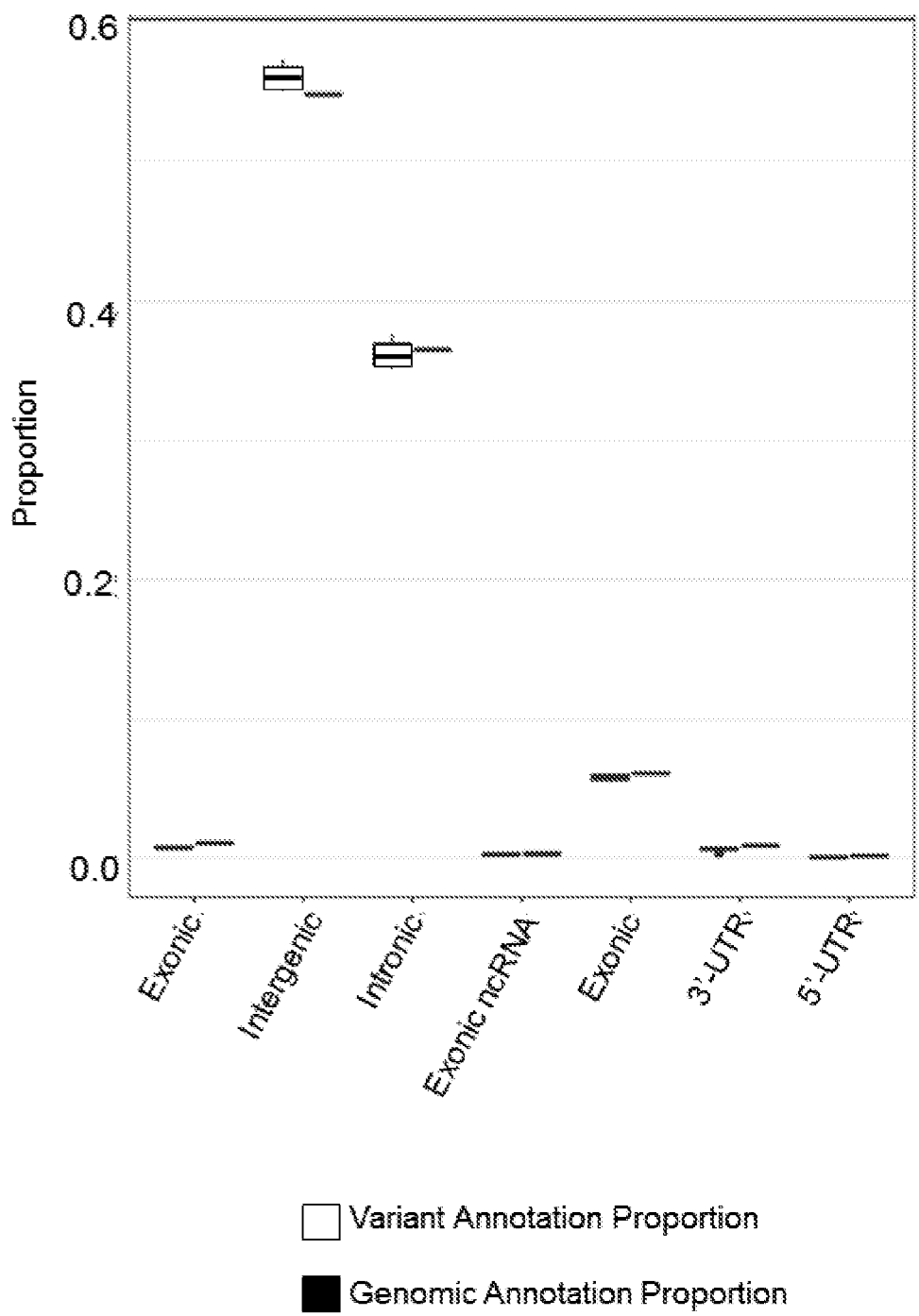
FIG. 12F shows a series of box plots of the proportion of ENU induced mutations in genomic locations with specific annotations. No specific enrichment was seen in specific annotations for variants (left boxes) in each cell relative to the proportion of the genome (right boxes) each annotation comprises.

Consistent with these studies, a dose-dependent increase in mutation number of each cell was observed, where a similar number of mutations were detected in the lowest dose of ENU compared to either vehicle control or toxic doses of mannitol (FIG. 12A). Also consistent with previous work in mice using ENU, the most common mutations are T to A (A to T), T to C (A to G), and C to T (G to A). The other three types of base changes were also observed, although C to G (G to C) transversion appears to be rare (FIG. 12B). An examination of the trinucleotide context of the SNVs illustrates two distinct patterns (FIG. 12C). The first pattern is that cytosine mutagenesis appears to be rare when cytosine is followed by guanine. Cytosine that is followed by guanine is commonly methylated at the fifth carbon site in human genomes, which is a marker of heterochromatin. Without being bound by theory, it was hypothesized that 5-methylcytosine does not undergo alkylation by ENU due to inaccessibility in heterochromatin or as a result of unfavorable reaction conditions with 5-methylcytosine compared to cytosine. To test the former hypothesis, locations of the mutation sites were compared to known DNase I hypersensitive sites in CD34+ cells that were catalogued by the Roadmap Epigenomics Project. As seen in FIG. 12D, no enrichment of cytosine variants in DNase I hypersensitivity sites was observed. Further, no enrichment of variants restricted to cytosines was observed in DH sites (FIG. 12E). Additionally, most thymine variants occur where adenine is present before thymine. Genomic feature annotation for the variants was not significantly different from the annotation of those features in the genome (FIG. 12F).

Example 4: Massively Parallel Single-Cell DNA Sequencing

Figure 10B:
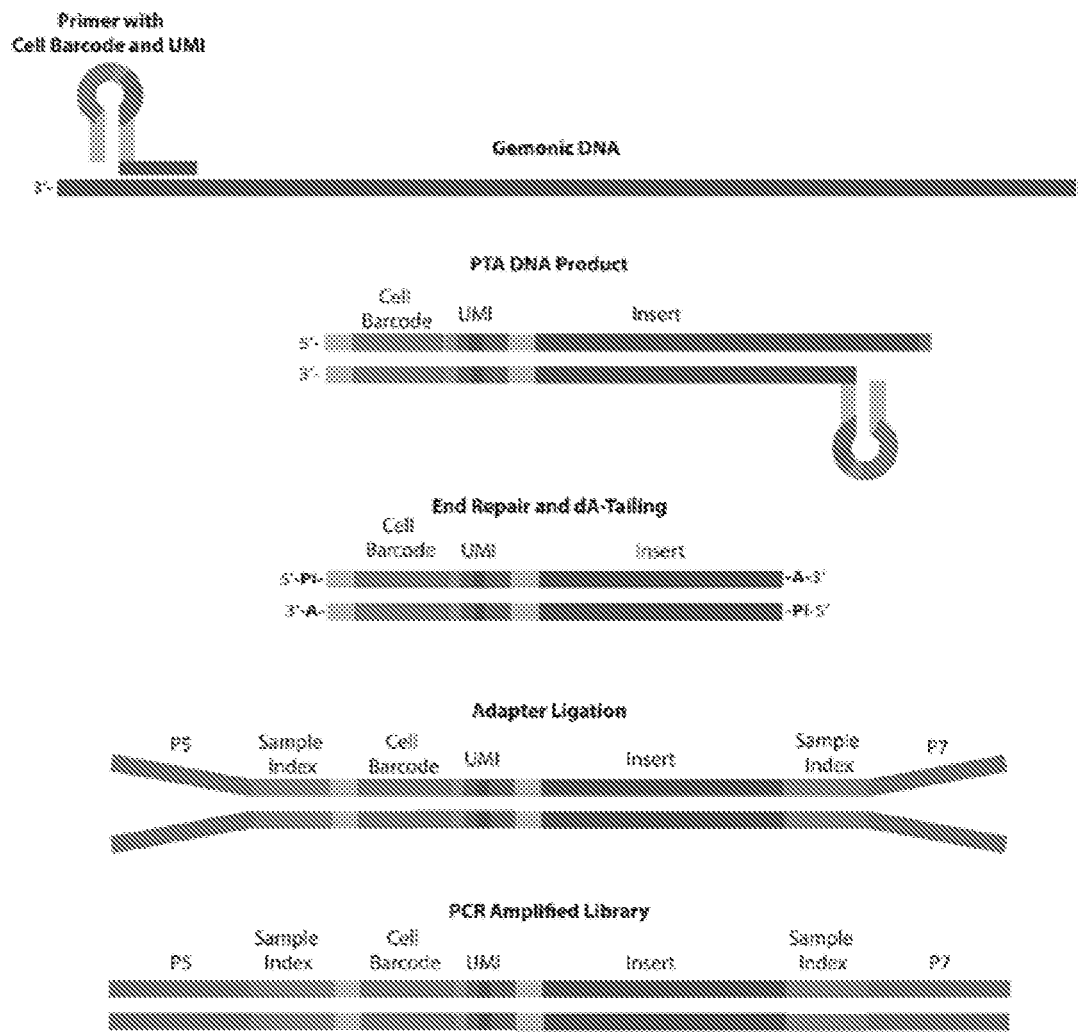
FIG. 10B demonstrates the incorporation of cellular barcodes and/or unique molecular identifiers into the PTA reactions using hairpin primers comprising cellular barcodes and/or or unique molecular identifiers.

Using PTA, a protocol for massively parallel DNA sequencing is established. First, a cell barcode is added to the random primer. Two strategies to minimize any bias in the amplification introduced by the cell barcode is employed: 1) lengthening the size of the random primer and/or 2) creating a primer that loops back on itself to prevent the cell barcode from binding the template (FIG. 10B). Once the optimal primer strategy is established, up to 384 sorted cells are scaled by using, e.g., Mosquito HTS liquid handler, which can pipette even viscous liquids down to a volume of 25 nL with high accuracy. This liquid handler also reduces reagent costs approximately 50-fold by using a 1 μL PTA reaction instead of the standard 50 L reaction volume.

Figure 9:
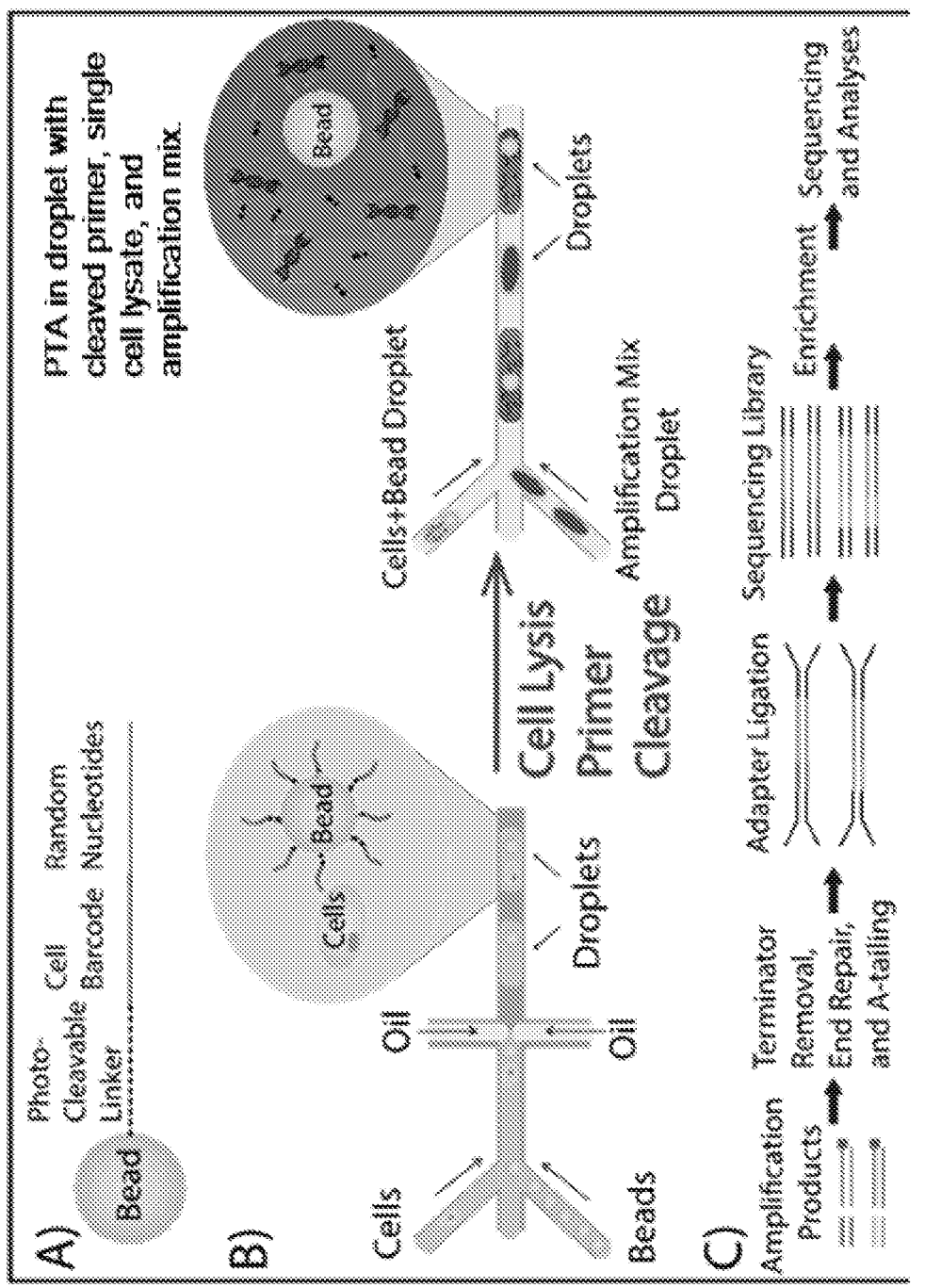
FIG. 9 (part A) shows beads with oligonucleotides attached with a cleavable linker, unique cell barcode, and a random primer. Part B shows a single cell and bead encapsulated in the same droplet, followed by lysis of the cell and cleavage of the primer. The droplet may then be fused with another droplet comprising the PTA amplification mix. Part C shows droplets are broken after amplification, and amplicons from all cells are pooled. The protocol according to the disclosure is then utilized for removing the terminator, end repair, and A-tailing prior to adapter ligation. The library of pooled cells then undergoes hybridization-mediated enrichment for exons of interest prior to sequencing. The cell of origin of each read is then identified using the cell barcode.

The amplification protocol is transitioned into droplets by delivering a primer with a cell barcode to a droplet. Solid supports, such as beads that have been created using the split-and-pool strategy, are optionally used. Suitable beads are available e.g., from ChemGenes. The oligonucleotide in some instances contains a random primer, cell barcode, unique molecular identifier, and cleavable sequence or spacer to release the oligonucleotide after the bead and cell are encapsulated in the same droplet. During this process, the template, primer, dNTP, alpha-thio-ddNTP, and polymerase concentrations for the low nanoliter volume in the droplets are optimized. Optimization in some instances includes use of larger droplets to increase the reaction volume. As seen in FIG. 9, this process requires two sequential reactions to lyse the cells, followed by WGA. The first droplet, which contains the lysed cell and bead, is combined with a second droplet with the amplification mix. Alternatively or in combination, the cell is encapsulated in a hydrogel bead before lysis and then both beads may be added to an oil droplet. See Lan, F. et al., Nature Biotechnol., 2017, 35:640-646).

Additional methods include use of microwells, which in some instances capture 140,000 single cells in 20-picoliter reaction chambers on a device that is the size of a 3"×2" microscope slide. Similarly to the droplet-based methods, these wells combine a cell with a bead that contains a cell barcode, allowing massively parallel processing. See Gole et al., Nature Biotechnol., 2013, 31:1126-1132).

Example 5: Application of PTA to Pediatric Acute Lymphoblastic Leukemia (ALL)

Figure 6B:
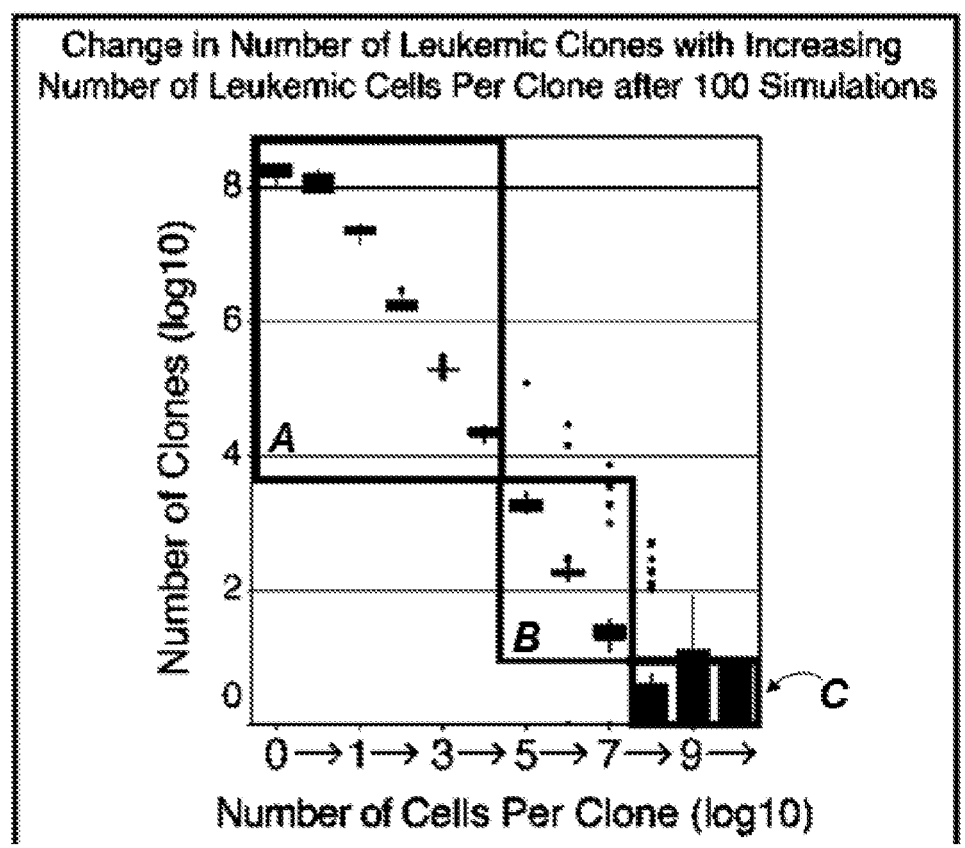
FIG. 6B shows a change in number of leukemic clones with increasing number of leukemic cells per clone after 100 simulations. Using per cell mutation rates, simulations predict a massive diversity of smaller clones created as one cell expands into 10-100 billion cells (box A). Only the highest frequency 1-5 clones (box C) are detected with current sequencing methods. In one embodiment of the invention, methods to determine drug resistance of the hundreds of clones that are just below the level of detection of current method (box B) are provided.

Single-cell exome sequencing of individual leukemia cells harboring an ETV6-RUNX1 translocation has been performed, measuring approximately 200 coding mutations per cell, only 25 of which have been present in enough cells to be detected with standard bulk sequencing in that patient. The mutation load per cell has then been incorporated with other known features of this type of leukemia, such as the replication-associated mutation rate (1 coding mutation/300 cell divisions), the time from initiation to diagnosis (4.2 years), and the population size at the time of diagnosis (100 billion cells) to create an in silico simulation of the development of the disease. It has been unexpectedly discovered that even in what has been thought to be a genetically simple cancer such as pediatric ALL, there are an estimated 330 million clones with distinct coding mutation profiles at the time of diagnosis in that patient. Interestingly, as seen in FIG. 6B, only the one to five most abundant clones (box C) are being detected with standard bulk sequencing; there are tens of millions of clones that are composed of a small number of cells and are thus less likely to be clinically significant (box A). Accordingly, methods are provided for enhancing the sensitivity of detection so that clones that make up at least 0.01% (1:10,000) of the cells (box B) can be detected, as this is the stratum in which most resistant disease that causes relapse is hypothesized to reside.

Figure 7:
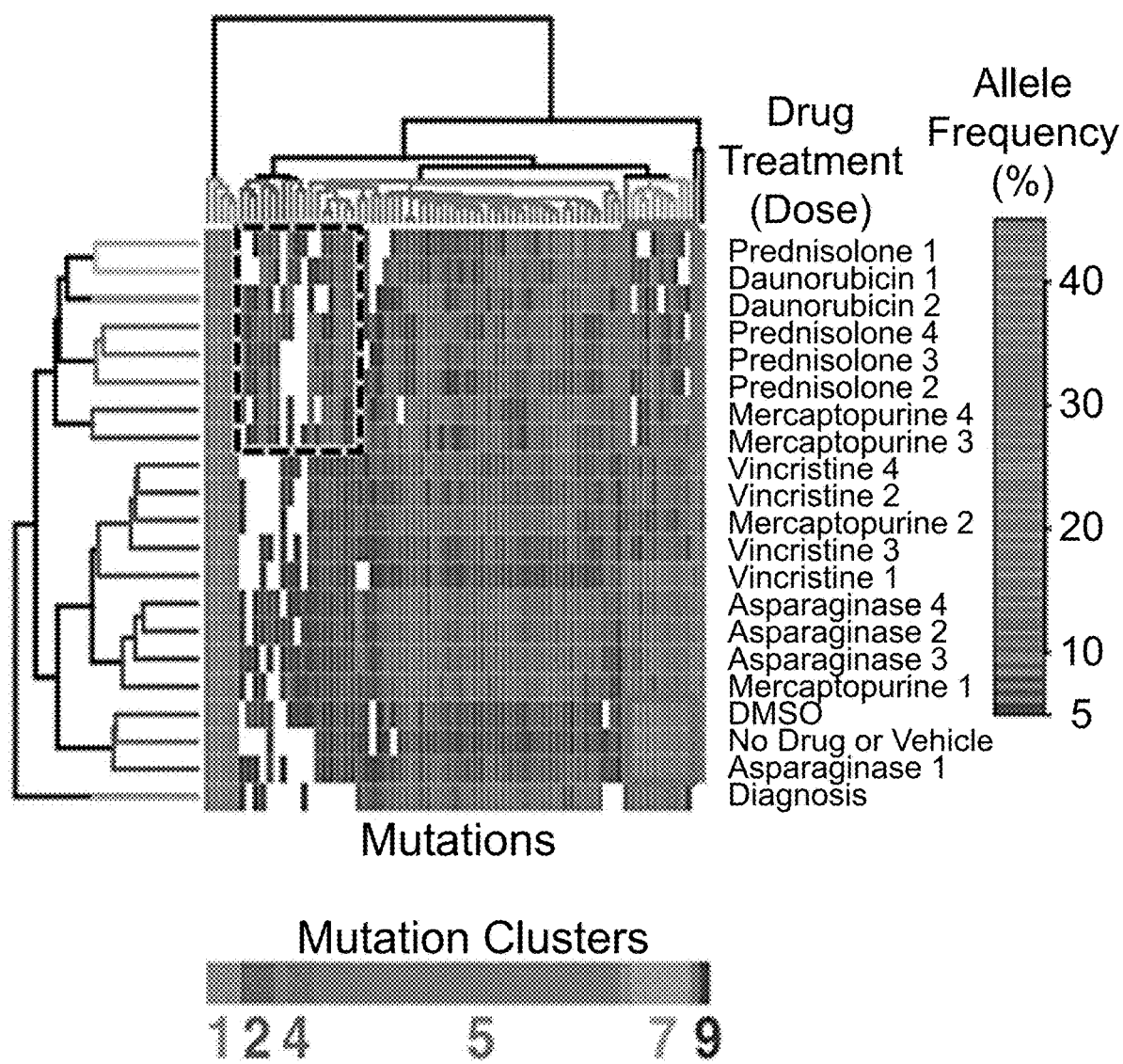
FIG. 7 shows an exemplary embodiment of the disclosure. Compared to the diagnostic sample on the bottom row, culturing without chemotherapy selected for a clone (red box, lower right corner) that harbored an activating KRAS mutation. Conversely, that clone was killed by prednisolone or daunorubicin (green box, upper right corner) while lower frequency clones underwent positive selection (dashed box).

Given such a massive population genetic diversity, it has been hypothesized that there are clones that are more resistant to treatment within a given patient. To test that hypothesis, the sample is placed in culture and the leukemia cells are exposed to increasing concentrations of standard ALL chemotherapy drugs. As seen in FIG. 7, in the control samples and those receiving the lowest dose of asparaginase, the clone harboring an activating KRAS mutation continued to expand. However, that clone proved more sensitive to prednisolone and daunorubicin, whereas other previously undetectable clones could be more clearly detected after treatment with those drugs (FIG. 7, dashed-line box). This approach also employed bulk sequencing of the treated samples. The use of single-cell DNA sequencing in some instances allows a determination of the diversity and clonotypes of the expanding populations.

Creating a Catalog of ALL Clonotype Drug Sensitivities

Figure 8:
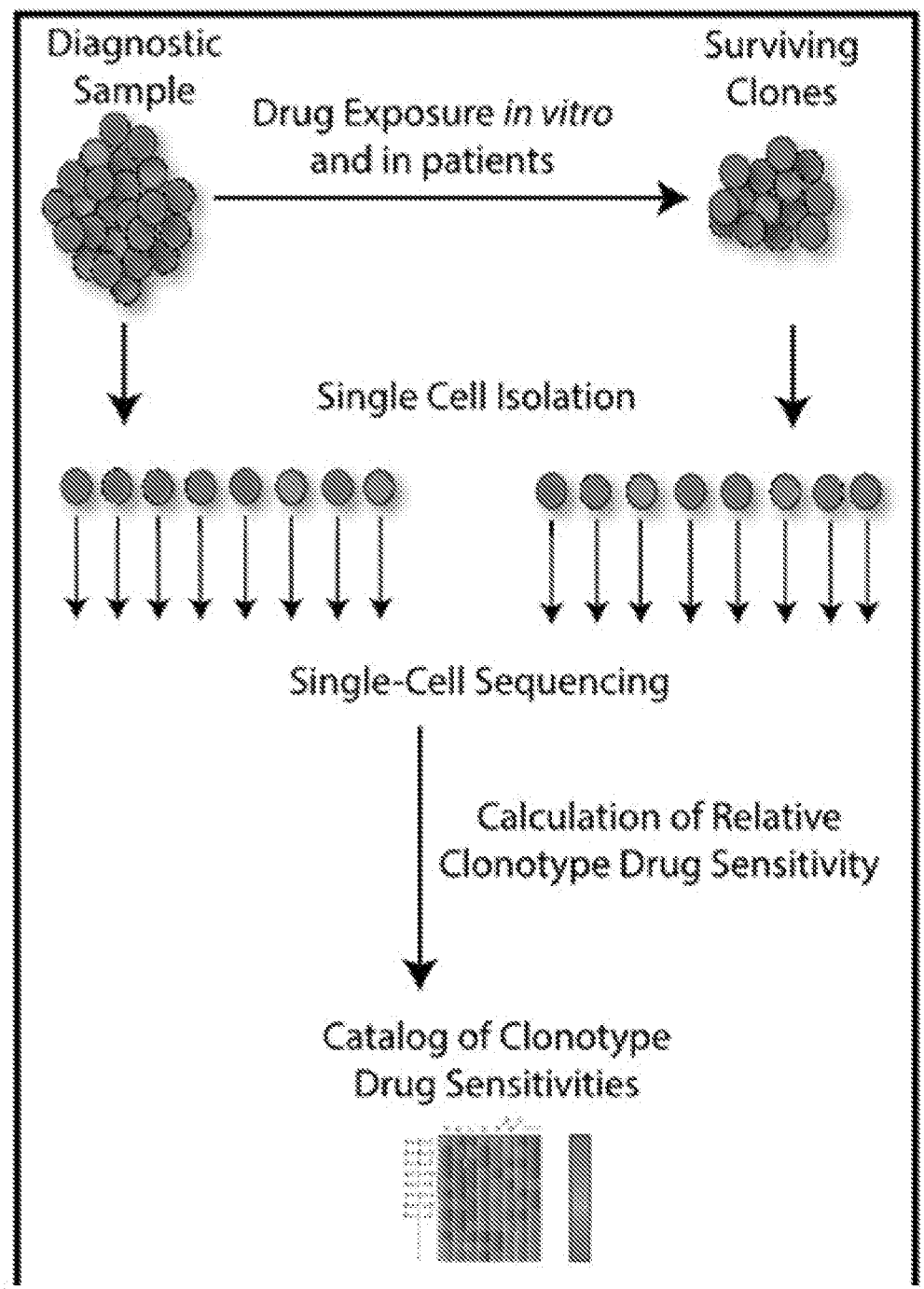
FIG. 8 is an overview of one embodiment of the disclosure, namely the experimental design for quantifying the relative sensitivities of clones with specific genotypes to specific drugs.

As shown in FIG. 8, to make a catalog of ALL clonotype drug sensitivities, an aliquot of the diagnostic sample is taken and single-cell sequencing of 10,000 cells is performed to determine the abundance of each clonotype. In parallel, the diagnostic leukemic cells are exposed to standard ALL drugs (vincristine, daunorubicin, mercaptopurine, prednisolone, and asparaginase), as well as to a group of targeted drugs (ibrutinib, dasatanib, and ruxolitinib) in vitro. Live cells are selected and single-cell DNA sequencing on at least 2500 cells per drug exposure will be performed. Finally, bone marrow samples from the same patients after they have completed 6 weeks of treatment are sorted for live residual preleukemia and leukemia, using established protocols for the bulk-sequencing studies. PTA is then used to perform single-cell DNA sequencing of tens of thousands of cells in a scalable, efficient, and cost-effective manner, which achieves the following goals.

From Clonotypes to a Drug Sensitivity Catalog of Drug Sensitivities

Once sequencing data are acquired, the clonotypes of each cell are established. To accomplish this, variants are called and clonotypes are determined. By utilizing PTA, the allelic dropout and coverage bias introduced during currently used WGA methods is limited. A systematic comparison of tools for calling variants from single cells that underwent MDA has been performed, and it was found that the recently developed tool Monovar has the highest sensitivity and specificity (Zafar et al., Nature Methods, 2016, 13:505-507). Once the variant calls have been made, it is determined if two cells have the same clonotype, despite some variant calls missing due to allelic dropout. To accomplish this, a mixture model of multivariate Bernoulli distributions may be used (Gawad et al., Proc. Natl. Acad. Sci. USA, 2014, 111(50):17947-52). After establishing that cells have the same clonotype, it is determined which variants to include in the catalog. Genes that meet any of the following criteria are included: 1) they are nonsynonymous variants detected in any of the mutational hotspots or loss-of-function variants (frameshift, nonsense, splicing) that occur in a known tumor-suppressor gene identified in the large pediatric cancer genome sequencing projects; 2) they are variants that are recurrently detected in relapsed cancer samples; and 3) they are recurrent variants that undergo positive selection in the current bulk-sequencing studies of residual disease as ALL patients undergo 6 weeks of treatment. If clones do not have at least two variants meeting these criteria, they are not included in the catalog. As more genes associated with treatment resistance or disease recurrence are identified, clones may be "rescued" and included in the catalog. To determine whether a clonotype underwent positive or negative selection between control and drug treatment, Fisher's exact test is used to identify clones that are significantly different from the control. Clones will only be added to the catalog when at least two concordant combinations of mutations are shown to have the same correlation with exposure to a specific drug. Known activating mutations in oncogenes or loss-of-function mutations in tumor suppressors in the same gene will be considered equivalent between clones. If clonotypes are not exactly concordant, the mutations in common will be entered into the catalog. For example, if clonotype 1 is A+B+C and clonotype 2 is B+C+D, the B+C clonotype will be entered into the catalog. If genes that are recurrently mutated in resistant cells with a limited number of co-occurring mutations are identified, those clones may be collapsed into functionally equivalent clonotypes.

Example 6: PTA Method

The PTA method is performed using the general methods of Example 1, with modification. In one embodiment, terminators are replaced with standard dNTPs, and additives are used to slow extension during amplification. In another embodiment, terminators are replaced with standard dNTPs, and the strand displacement polymerase is modified to slow its extension rate. In another embodiment, terminators are replaced with dNTPs which incorporate more slowly during extension than standard nucleotides, or which result in a slower extension reaction after incorporation than from a template comprising standard nucleotides. Such slow-incorporation dNTPs in some instances are nuclease resistant.

Example 7: Hairpin or Loop Method with Terminators

A sample is optionally lysed (such as a single cell), and sample template ("target nucleic acid molecule) DNA is subjected to quasi-random priming and linear amplification. A mixture of terminators and dNTPs are used during quasi-random priming step. Primers are designed to generate hairpin or looping structures, which are less efficient templates for further amplification than the original sample template DNA. This results in a higher proportion of amplicons originating from the original sample template. Next, the library of amplicons is further amplified with an exponential amplification step to generate a library for sequencing. In some instances, lysis, linear amplification, and exponential amplification occur in the same container. Alternately or in combination, terminators are used in the exponential amplification step. In some instances, standard dNTPs are used during linear amplification, and terminators are used during exponential amplification steps. Use of terminators results in a decrease in non-original template amplification when compared with non-terminator nucleotides.

Example 8: Recombinase Polymerase Amplification (RPA) with Terminators

A sample is optionally lysed (such as a single cell), and sample template DNA is subjected to an RPA reaction mixture (for an exemplary procedure, Daher et al., Clin. Chem. 2016, 62(7), 947-958) comprising a recombinase, a single-strand DNA binding protein, primers, a polymerase, and a mixture of terminators and dNTPs. For example, the recombinase is RecA, and the single stranded DNA binding protein is SSB. In some instances the recombinase is T4 UvsX, and the single stranded DNA binding protein is T4 gp32. Various polymerases include but are not limited to Sau polymerase or Bsu polymerase. In some instances, additional agents such as polyethylene glycol or Carbowax20M are added to the reaction mixture. In some instances, a reverse transcriptase is added to amplify RNA sample templates. In some instances, fully or partially randomized primers are used. Amplicons generated by RPA are optionally subjected to additional steps, such as ligation to adapters, exponential amplification, sequencing, or any combination thereof. Use of terminators results in a decrease in non-original template amplification when compared with non-terminator nucleotides.

Example 9: Helicase-Dependent Amplification (HDA) with Terminators

A sample is optionally lysed (such as a single cell), and sample template DNA is subjected to an HDA reaction mixture (for an exemplary procedure, Yang et al., Chembiochem 2015, 16(9), 1365-1370) comprising a helicase, a polymerase, and a mixture of terminators and dNTPs. For example, the polymerase is Bst2.0, GspM, GspM2.0, GspSSD, or other polymerase) and the helicase is a thermophilic helicase, Tte-UvrD, or other helicase. In some instances, an additional single stranded DNA binding protein is added. In some instances, a reverse transcriptase is added to amplify RNA sample templates. In some instances, fully or partially randomized primers are used. Amplicons generated by HDA are optionally subjected to additional steps, such as ligation to adapters, exponential amplification, sequencing, or any combination thereof. Use of terminators results in a decrease in non-original template amplification when compared with non-terminator nucleotides.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of amplifying at least one target nucleic acid molecule, the method comprising:
   a. contacting a sample comprising the at least one target nucleic acid molecule, at least one amplification primer, at least one nucleic acid polymerase comprising 3'-5' exonuclease activity, and a mixture of nucleotides, wherein the mixture of nucleotides comprises at least one terminator nucleotide which terminates nucleic acid replication by the polymerase, wherein the terminator nucleotide is an irreversible terminator which inhibits 3'-5' exonuclease activity of the polymerase, and is selected from nucleotides with modification to the alpha group, C3 spacer nucleotides, locked nucleic acids (LNA), inverted nucleic acids, 2' fluoro nucleotides, 3' phosphorylated nucleotides, 2'-O-Methyl modified nucleotides, and trans nucleic acids, and
   b. amplifying the at least one target nucleic acid molecule to generate a plurality of terminated amplification products, wherein the terminator nucleotide is attached to the 3' terminus of the terminated amplification products, and wherein the replication proceeds by strand displacement replication.

2. The method of claim 1, wherein the nucleic acid polymerase is bacteriophage phi29 (129) polymerase, genetically modified phi29 (Φ29) DNA polymerase, phage M2 DNA polymerase, phage phiPRD1 DNA polymerase, Bsu DNA polymerase, a polymerase, a polymerase, DNA polymerase I, T5 DNA polymerase, T7 DNA polymerase, T4 DNA polymerase or thermophilic DNA polymerases.

3. The method of claim 1, wherein the amplification primers are 4 to 70 nucleotides in length and the at least one amplification primer comprises a randomized region.

4. The method of claim 1, wherein the amplification is performed under conditions wherein the temperature varies by no more than 10 degrees C.

5. The method of claim 1, wherein at least 3% of the terminated amplification products are direct copies of the at least one target nucleic acid molecule.

6. The method of claim 1, wherein the ratio of terminated amplification products which are direct copy amplicons to target nucleic acid molecules is at least a 10:1.

7. The method of claim 1, wherein the least one terminator nucleotide comprises modifications of the r group of the 3' carbon of the deoxyribose.

8. The method of claim 1, wherein the at least one terminator nucleotide comprises modification to the alpha group.

9. The method of claim 8, wherein the nucleotides with modification to the alpha group are alpha-thio dideoxynucleotides.

10. The method of claim 1, wherein the terminator nucleotides do not comprise a detectable moiety or tag.

11. The method of claim 1 wherein the terminator nucleotides reduce exonuclease proofreading activity of the at least one nucleic acid polymerase on the terminated amplification products by at least 85%.

12. The method of claim 1, wherein the mixture of nucleotides further comprises a mixture of nucleotides which are not attached to the polynucleotides, wherein the mixture comprises deoxynucleoside triphosphates and terminator nucleotides in a 1:1 to 1000:1 ratio.

13. The method of claim 1, wherein the amplification products are between about 50 and about 2000 nucleotides in length.

14. The method of claim 13, wherein the amplification products are between about 200 and about 1000 nucleotides in length.

15. The method of claim 1, wherein the method further comprises an additional amplification step using PCR.

16. The method of claim 15, wherein the method further comprises sequencing.

17. The method of claim 1, wherein the at least one amplification primer comprise a barcode.

18. The method of claim 17, wherein the barcode comprises a cell barcode or a sample barcode.

19. The method of claim 1, wherein the at least one target nucleic acid is obtained from a single cell.

20. The method of claim 1, wherein the at least one target nucleic acid is obtained from human genomic DNA.

* * * * *